(12) United States Patent
Fang et al.

(10) Patent No.: US 8,168,586 B1
(45) Date of Patent: May 1, 2012

(54) CANCER TARGETS AND USES THEREOF

(75) Inventors: Dong Fang, San Diego, CA (US); Paul Moore, North Bethesda, MD (US); Steve Ruben, Brookville, MD (US); Sudeepta Aggarwal, North Potomac, MD (US)

(73) Assignee: Celera Corporation, Alameda, CA (US)

( * ) Notice: Subject to any disclaimer, the term of this patent is extended or adjusted under 35 U.S.C. 154(b) by 473 days.

(21) Appl. No.: 12/275,779

(22) Filed: Nov. 21, 2008

Related U.S. Application Data

(60) Provisional application No. 61/003,930, filed on Nov. 21, 2007.

(51) Int. Cl.
*A61K 38/00* (2006.01)
*G01N 33/574* (2006.01)
*C12Q 1/68* (2006.01)
*A61K 51/10* (2006.01)
*A61K 39/00* (2006.01)

(52) U.S. Cl. ...... 514/1.2; 435/7.23; 435/6.17; 424/1.49; 424/181.1; 530/387.1

(58) Field of Classification Search .................. None
See application file for complete search history.

(56) References Cited

FOREIGN PATENT DOCUMENTS
WO 2004028479 A2 4/2004

OTHER PUBLICATIONS

Newell, DR; Eur. J. Canc. 41 (2005) 676-682.*
U.S. Appl. No. 12/077,323, Issue Date Mar. 17, 2008, Celera Corporation Non-Published Application.

* cited by examiner

*Primary Examiner* — Doug Schultz
(74) *Attorney, Agent, or Firm* — Celera Corporation

(57) ABSTRACT

Methods and compositions are provided for assessing, treating, and preventing diseases, especially cancer, using cancer-associated targets ("CAT"). Methods and compositions are also provided for determining or predicting the effectiveness of a treatment for these diseases or for selecting a treatment, using CAT. Methods and compositions are further provided for modulating cell function using CAT. Also provided are compositions that modulate CAT (e.g., antagonists or agonists), such as antibodies, proteins, small molecule compounds, and nucleic acid agents (e.g., RNAi and antisense agents), as well as pharmaceutical compositions thereof. Further provided are methods of screening for agents that modulate CAT, and agents identified by these screening methods.

4 Claims, 4 Drawing Sheets

Angiopoietin-Like 4 (ANGPTL4)

Tweety Homolog 3 (TTYH3)

Protein FLJ11273

CANCER TARGETS AND USES THEREOF

FIELD OF THE INVENTION

This invention relates to the field of disease assessment and therapy. The invention provides compositions and methods for assessing and treating diseases, especially cancer.

BACKGROUND OF THE INVENTION

Cancer

Cancer is one of the leading causes of death worldwide, and cancer is difficult to diagnose and treat effectively. Accordingly, there is a need in the art for new compositions and methods for assessing and treating various cancers.

Cancer Stem Cells (CSCs)

Cancer stem cells (CSCs), which may also be referred to as tumor stem cells, are cancer cells that are operationally similar to normal stem cells and that typically have the ability to grow (or re-grow) a tumor. For example, like normal stem cells, CSCs typically possess the properties of self-renewal ability, extensive proliferation potential, and the potential to differentiate into multiple phenotypically different cell types. CSCs can potentially arise from, for example, mutation of a normal adult stem cell or from mutations that impart stem cell-like properties to another type of cell. Therefore, CSCs may or may not originate from their normal stem cell counterpart. However, regardless of whether or not the cell of origin of a CSC is in fact a true stem cell, the term CSC is used in the art on the basis of the cancer cell having properties that are similar to normal stem cells.

For example, recent studies have demonstrated that in many types of cancer, only a small subset of cancer cells within a tumor have the ability to proliferate extensively, to initiate the growth of new tumors (including metastatic growth), and to differentiate into the various different cell types that make up a typical, complex heterogeneous tumor. These cells are the CSCs, and these properties are typical of CSCs. Some CSCs have previously been isolated (e.g., from leukemia, as well as brain, breast, and lung cancers) and, when transplanted into an animal model (or even serially passaged into multiple animals), have been shown to be necessary and sufficient to initiate the growth of new tumors, whereas the vast majority of other cells within a tumor do not have the capability to initiate the growth of new tumors.

However, current cancer therapies (including, for example, chemotherapy and radiation therapy) generally attempt to non-discriminately kill proliferating cells, and potential therapeutic agents are commonly selected based on their ability to reduce tumor size. Furthermore, clinical trials of anti-cancer agents are commonly designed with the objective of demonstrating a reduction in tumor size. However, because cancer stem cells typically make up only a small proportion of a tumor, reduction in tumor size may not be indicative of any reduction in cancer stem cell populations, and therefore reduction in tumor size may not accurately reflect longer-term cancer prognosis. Because CSCs typically represent only a minor portion of a tumor and can be quiescent (non-proliferating), cancer therapies may primarily kill other cells that make up the majority of the tumor, thereby often leading to tumor shrinkage and possibly temporary cancer remission or other clinical improvement. However, because the CSCs have not been directly targeted and killed, CSCs may survive the cancer therapy and eventually initiate re-growth of the cancer. Thus, to permanently eradicate a cancer and to prevent metastasis, it would be desirable to specifically kill the CSCs. Similarly, to gain a more comprehensive diagnosis of a cancer, such as in predicting the reoccurrence of a cancer following treatment or the threat of metastasis, it would be desirable to specifically assess the CSCs.

Therefore, there is a need in the art to identify cancer stem cell markers (e.g., proteins expressed by cancer stem cells, and the encoding nucleic acid molecules), as well as agents (e.g., antibodies) that target these cancer stem cell markers, so that more effective cancer therapies and diagnostics can be implemented that specifically target the small population of tumor cells within a tumor that are cancer stem cells and which can be most harmful to a patient with regards to tumor growth, metastasis and initiation of new tumors, and re-growth of tumors following treatment.

For a further review of CSCs, see the following (each of these references is incorporated herein by reference): Fang et al., "A tumorigenic subpopulation with stem cell properties in melanomas", Cancer Res. 2005 Oct. 15; 65(20):9328-37; Lee et al., "Tumor stem cells derived from glioblastomas cultured in bFGF and EGF more closely mirror the phenotype and genotype of primary tumors than do serum-cultured cell lines", Cancer Cell. 2006 May; 9(5):391-403; Nishizuka, "Profiling cancer stem cells using protein array technology", Eur J Cancer. 2006 June; 42(9):1273-1282; Reya et al., "Stem cells, cancer, and cancer stem cells", Nature 2001 Nov. 1; 414(6859):105-11; Huff et al., "The paradox of response and survival in cancer therapeutics", Blood 2006 Jan. 15; 107(2):431-4; Feinberg et al., "The epigenetic progenitor origin of human cancer", Nat Rev Genet 2006 January; 7(1): 21-33; Al-Hajj et al., "Therapeutic implications of cancer stem cells", Curr Opin Genet Dev. 2004 February; 14(1):43-7; Soltysova et al., "Cancer stem cells", Neoplasma 2005; 52(6):435-40; Wang et al., "Cancer stem cells: lessons from leukemia", Trends Cell Biol. 2005 September; 15(9):494-501; Jordan, "Cancer stem cell biology: from leukemia to solid tumors", Curr Opin Cell Biol. 2004 December; 16(6): 708-12; Liu et al., "Adult stem cells and cancer stem cells: tie in or tear apart?", J Cancer Res Clin Oncol. 2005 October; 131(10):631-8; Bjerkvig et al., "Opinion: the origin of the cancer stem cell: current controversies and new insights", Nat Rev Cancer 2005 November; 5(11):899-904; Brabletz et al., "Opinion: migrating cancer stem cells—an integrated concept of malignant tumour progression", Nat Rev Cancer 2005 September; 5(9):744-9; Jones et al., "Cancer stem cells: are we missing the target?", J Natl Cancer Inst. 2004 Apr. 21; 96(8):583-5; Al-Hajj et al., "Self-renewal and solid tumor stem cells", Oncogene 2004 Sep. 20; 23(43):7274-82; Kopper et al., "Tumor stem cells", Pathol Oncol Res. 2004; 10(2): 69-73; Cheng, "Cell cycle inhibitors in normal and tumor stem cells", Oncogene 2004 Sep. 20; 23(43):7256-66; and U.S. Pat. No. 6,984,522 ("Isolation and Use of Solid Tumor Stem Cells").

Description of the Files Contained on the CD-R Named CL001733CDR

The CD-R named CL001733CDR contains the following three text (ASCII) files:

1) File SEQLIST_1733ORD.txt provides the Sequence Listing. The Sequence Listing provides exemplary protein sequences (SEQ ID NOS:1-722, 1975, and 1977), transcript sequences (SEQ ID NOS:723-1281, 1976, and 1978), and peptide sequences (SEQ ID NOS:1282-1974) as shown in Table 1. File SEQLIST_1733ORD.txt is 5,905 KB in size and was created on Nov. 20, 2008.

2) File TABLE1_1733.txt provides Table 1, which is 1,018 KB in size and was created on Nov. 20, 2007.

3) File TABLE2_1733.txt provides Table 2, which is 14 KB in size and was created on Nov. 20, 2007.

The material contained on the CD-R named CL001733CDR is hereby incorporated by reference pursuant to 37 CFR 1.77(b)(4).

LENGTHY TABLES

The patent contains a lengthy table section. A copy of the table is available in electronic form from the USPTO web site (http://seqdata.uspto.gov/?pageRequest=docDetail&DocID=US08168586B1). An electronic copy of the table will also be available from the USPTO upon request and payment of the fee set forth in 37 CFR 1.19(b)(3).

Description of Table 1

Table 1 (provided on the CD-R) discloses cancer-associated target ("CAT") proteins, transcripts, and peptides (each protein, transcript, and peptide is represented by a SEQ ID NO in Table 1, and the corresponding sequence is provided in the Sequence Listing; the range of numbers in parentheses following each peptide SEQ ID NO represents the amino acid residues of the location of the peptide within its corresponding protein), the disease (e.g., cancer) cell lines or tissues, the expression ratio ("ratio") of the peptide in the disease sample compared to a control sample, and the type of cancer (or, if "adipose" is indicated, adipose disease such as diabetes or obesity) in which differential expression of the target was observed ("disease").

The expression ratio is based on measuring the expression level of the peptides, which are fragments of each full-length protein. Thus, the expression level of the peptides is indicative of the expression level of the corresponding protein of which the peptide is a fragment. Numerical representation of over-expression is indicated by 2.0 or more, whereas numerical representation of under-expression is indicated by 0.5 or less. Over-expressed singleton indicates that a peptide peak was detected in a disease (e.g., cancer) sample but no peak was detected in a control sample. Under-expressed singleton indicates that a peptide peak was detected in a control sample but no peak was detected in a disease sample.

The protein/gene/transcript information provided for each target includes any or all of the information selected from the following:
- a protein SEQ ID NO
- an internal identification number for the protein (hCP and/or UID)
- a public protein accession number (Genbank, e.g., RefSeq NP number, Swiss-prot, or Derwent) for the protein
- a protein name recognized in the art
- an internal identification number for the gene (hCG and/or UID)
- an art-recognized gene symbol
- OMIM ("Online Mendelian Inheritance in Man" database; Johns Hopkins University/NCBI) gene/protein name(s) and/or symbol(s)
- a transcript SEQ ID NO
- an internal identification number for the transcript (hCT and/or UID)
- a public transcript accession number (Genbank, e.g., RefSeq NM number, or Derwent)

Description of Table 2

Table 2 discloses tumor staging information for tumor tissue samples listed in Table 1, as follows (all tumor staging designations in Table 2 are conventional in the art):

Sample ID Number (corresponding to a tumor tissue sample listed in Table 1), sample type (labeled "Sample"), cancer type (labeled "Type"), Lymph Nodes (the "N" in the TNM staging system, for Node, which designates the spread of a tumor to the lymph nodes), Distant Metastasis (the "M" in the TNM staging system, for Metastasis, which designates the extent of tumor metastasis), Extent of Invasion (the "T" in the TNM staging system, for Tumor, which designates the size and location of a primary tumor), and AJCC Stage (which is assigned based on a combination of the T, N, and M classifications).

Description of Table 3

Table 3 summarizes results of expression and functional validation analyses for the cancer-associated targets ("CAT") provided herein.

The column labeled "Target Symbol" provides the target symbol identifying the target, which can be used to cross-reference targets between Table 3 and Table 1.

The column labeled "IHC" provides results of immunohistochemistry analysis of target protein expression in tumor tissue samples. For IHC studies, the expression of each target was typically evaluated in 10 tumor specimen for 10-14 cancer indications and 2 normal specimens of the same tissue type. A pathology score was given to each specimen by a certified pathologist. The pathology scores were based on: (i) staining intensity that ranged from 0-4, 0 being the weakest and 4 being the strongest staining, and (ii) the number of cells staining positive; for a specimen to be considered positively stained, >25% percent of cells needed to have a staining score of 1 or above. Once the scores are assigned for each specimen, the percent of tumors that have 2 or more pathology scores above the highest normal is calculated. These percentages are listed in Table 3 (in the column labeled "IHC").

The columns labeled "Apoptosis" and "Proliferation" provide results of apoptosis and cell proliferation functional assays, respectively, in cancer cell lines in which each target was knocked down by RNAi. In the proliferation or apoptosis columns, a "+" indicates that the target has been functionally validated based on an RNAi screen. Experimentally, a pool of four RNAi duplexes against a target was transfected in one or more cell lines for each indication. If the transfection results in >35% decrease in proliferation or >2-fold increase in apoptosis in a cell line, the results were considered significant and the target was assigned a "+" notation (which is indicated in Table 3).

Once a cell line has passed a screen, further validation steps were undertaken. First, the screen positive cell line is transfected with maximum concentration (100 nM) of each of four individual duplexes that were included in the pool in the above description. Typically, 1-2 duplexes out of the pool of 4 will show similar effects on proliferation and/or apoptosis as the pool transfection. Effect of mRNA knockdown by individual duplexes was also measured at this stage. Next, decreasing concentrations of the selected duplex (100 nM down to 1 nM) were transfected into the cell line to confirm specificity of the selected duplex. If decreasing the duplex concentration resulted in decreased effect on proliferation and apoptosis of the cell line, the target was considered to be functionally validated and was therefore assigned a "++" notation (which is indicated in Table 3).

For selected targets, if an antibody is commercially available or has been custom generated, the effect of inhibition of the cell line proliferation was measured in the presence of different concentrations of the antibody and its isotype control. If the presence of an antibody against a target showed inhibition of proliferation in one or more cell lines, the target was considered functionally validated using an antibody and was therefore assigned a "+++" notation (which is indicated in Table 3) (a target with a "+++" notation was not necessarily also "++" validated).

The column labeled "Matrix" refers to the experiments where the comparisons were made between "case" and "control" to identify the over-expressed protein/peptides. Each matrix entry is identified by a prefix that defines the cell line and a suffix that defines the comparison or culture condition used to generate the cell line. As examples, 1. H1299_Stemcell_Cys_only:

Spheroids (stem cells) generated from lung H1299 cell line were compared to adherent cells obtained either from (i) primary culture or (ii) spheroid population; only cystine containing peptides were analyzed in this experiment.

2. H1299_Stemcell_Glyco:

Spheroids (stem cells) generated from lung H1299 cell line were compared to adherent cells obtained either from (i) primary culture or (ii) spheroid population; only peptides captured based on glycosylated residues were analyzed in this experiment.

3. CBT026_HES_Primary

Spheroids (stem cells) generated from colon tumor tissue CBT026T were compared to the primary processed tumor tissue.

4. HT29_Stemcell:

Spheroids (stem cells) generated from colorectal cell line HT29 were compared to adherent cells obtained from primary culture.

5. CBT026_T:

Spheroids (stem cells) generated from colon tumor tissue CBT026T were compared to the adherent cells in culture obtained from the same tumor tissue.

6. CBT026_N:

Spheroids (stem cells) generated from normal colon tissue CBT026N were compared to the adherent cells in culture obtained from the same tissue.

7. RKO Sphere:

Spheroids (stem cells) generated from colorectal cell line RKO were compared to adherent cells obtained from primary culture.

8. Melanoma Stemcell_EGT003D:

Spheroids (stem cells) generated from melanoma tumor tissue EGT003D were compared to the adherent cells in culture obtained from the same tissue.

9. LS123_Stemcell:

Spheroids (stem cells) generated from colorectal cell line LS123 were compared to adherent cells obtained from primary culture.

10. CBT026__12Maps:

Spheroids (stem cells) generated from colon tumor tissue CBT026T and normal tissue CBT026N were compared with adherent cells obtained from culturing these tissues.

11. CBT026_five sets with N Primary:

Spheroids (stem cells) generated from colon tumor tissue CBT026T or adherent cells were compared to spheroids and adherent cells from normal tissue.

Further information about cell lines:

Lung metastatic non-small cell lung cancer cell line H1299 (catalog no. CRL-5803) was purchased through ATCC and cultured according to the vendor recommendations.

Colorectal cancer cell lines HT-29 (Catalog no. HTB-39), LS123 (catalog number: CCL-255), and RKO (catalog no. CRL-2577) were also obtained from ATCC and cultured according to the vendor recommendations.

Spheroid cells (stem cells) were generated from colorectal tumor tissue CBT026T (from 62 yr old male; grade: G2; stage: IIIC; TNM Status: T4N2MX) and its adjacent normal colorectal tissue CBT026N. The spheroid cell line generated from colorectal tumor tissue CBT026T (which was used in comparisons that are designated in the "Matrix" column of Table 3 as "CBT026_T" and "CBT026_HES_Primary") has been deposited with the American Type Culture Collection (ATCC), 10801 University Boulevard, Manassas, Va. 20110-2209, USA, under the terms of the Budapest Treaty on the International Recognition of the Deposit of Microorganisms for the Purpose of Patent Procedure on Jul. 21, 2006 and bears the ATCC accession number PTA-7742.

Spheroid cells (stem cells) were generated from melanoma tumor tissue EGT003D (identified in the "Matrix" column of Table 3 as "Melanoma StemCell_EGT003D").

The column labeled "Subcellular Location" indicates the cellular location of the target (either cell surface or secreted).

Figure 1:
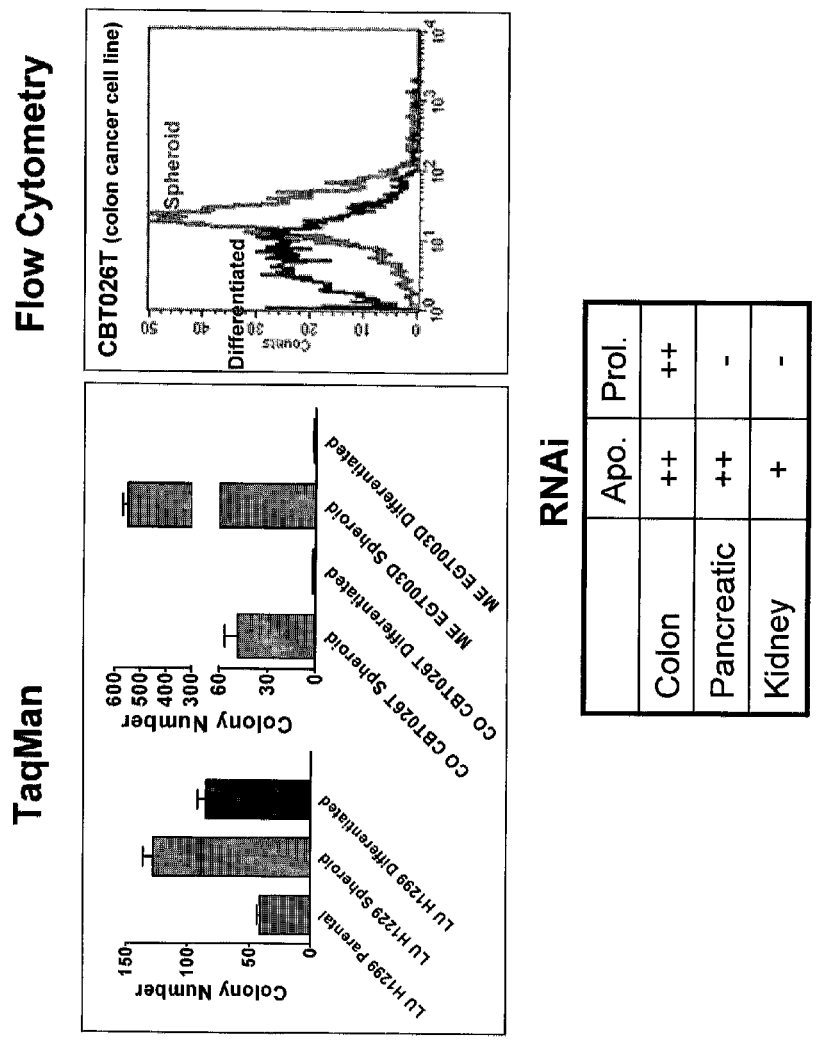
FIGS. 1-4. Results of experimental validation (TaqMan, RNAi, and, for ANGPTL4, Flow Cytometry) for Angiopoietin-like 4 protein (ANGPTL4) (FIG. 1), Tweety Homolog 3 (TTYH3) (FIG. 2), CEACAM6 (FIG. 3), and Protein FLJ11273 (FIG. 4).

In the figures, with respect to RNAi validation results, "Apo." refers to an apoptosis assay, and "Prol." refers to a cell proliferation assay. "+", "++", and "−" indicate relative degree of RNAi-mediated effect observed in the assay (either inducement of apoptosis or inhibition of cell proliferation) in various cancer cell lines (as indicated), with "+" indicating that an RNAi-mediated effect was observed, "++" indicating that a strong RNAi-mediated effect was observed, and "−" indicating that an RNAi-mediated effect was not observed.

H1299 is a lung cancer cell line, CBT026T is a colon cancer cell line, and EGT003D is a melanoma cell line.

Cell lines labeled "DMEM" refer to differentiated (adherent) cell lines (DMEM indicates a type of culture medium suitable for the growth of differentiated cells). Cell lines labeled "HES" and "HES-S" refer to cancer stem cell lines (HES and HES-S, which are used herein interchangeably, indicate a type of culture media suitable for the growth of human embryonic stem, or "HES", cells and cancer stem cells). Cell lines labeled "H/D" refer to differentiated cell populations derived from cancer stem cells. Cell lines labeled "MBM4" refer to adherent melanoma cells generated in vitro from a primary tumor by culturing in serum-containing melanoma cell-derived MBM4 medium.

DETAILED DESCRIPTION OF EXEMPLARY EMBODIMENTS OF THE INVENTION

The invention will best be understood by reference to the following detailed description of the exemplary embodiments, taken in conjunction with the accompanying table(s) and/or figure(s). The discussion below is exemplary and is not to be taken as limiting the scope defined by the claims.

The invention generally relates to molecules that have been identified using proteomic analysis techniques such as MALDI-TOF/TOF LC/MS-based protein expression analysis to determine the expression levels of proteins in disease tissues and/or disease cell lines (tissues and cell lines may be collectively referred to as "samples") and in normal tissues and/or normal cell lines, such that proteins that are differentially expressed (e.g., over- or under-expressed) in disease samples compared with normal samples are identified.

Exemplary embodiments of the invention provide the targets shown in Tables 1 and 3 and methods of using these targets. Four of these targets (ANGPTL4, TTYH3, CEACAM6, and Protein FLJ11273) are also shown in the figures and described in section 13 of the Examples section (which is entitled "Specific Examples of Results from Experimental Validation"). All of these targets (i.e., the targets provided in Table 1, Table 3, and/or the figures) are collectively referred to herein as "CAT" ("cancer-associated targets"). In particular, exemplary embodiments of the invention provide methods of using these targets for assessing (e.g., diagnosing, prognosing, or determining future susceptibility), treating, and preventing cancer. Each of these targets is associated with specific types of cancers in particular, as shown in Tables 1 and 3, the figures, and/or described in section 13 of the Examples section. These targets also are expressed by cancer stem cells and therefore these targets have utilities with respect to cancer stem cells, in addition to their other cancer-related uses, such as for specifically targeting cancer stems cells (e.g., for therapeutic or diagnostic purposes) or for detecting, isolating, and/or labeling cancer stem cells.

Based on, for example, the finding that certain proteins, referred to herein as cancer-associated target ("CAT") proteins, are differentially expressed in cancer samples in comparison with normal samples, exemplary embodiments of the invention provide methods and compositions for assessing, treating, and preventing diseases, especially cancer, particularly the cancers identified in Table 1 (as indicated for each peptide) and/or Table 3, using CAT. Furthermore, the compositions and methods of the invention may be suitable for other types of cancer, particularly other epithelial cell-related cancers and solid tumors.

Cancer-associated target ("CAT") proteins and fragments thereof (e.g., CAT peptides), and CAT nucleic acid molecules and fragments thereof encoding CAT proteins and peptides, are collectively referred to as CAT or "targets" (which may be interchangeably referred to as "markers" or "biomarkers"). Exemplary CAT proteins are provided as SEQ ID NOS:1-722, 1975, and 1977, exemplary fragments of these CAT proteins are provided as the peptide sequences of SEQ ID NOS:1282-1974, and exemplary CAT transcript sequences (which encode the CAT proteins of SEQ ID NOS:1-722, 1975, and 1977) are provided as SEQ ID NOS:723-1281, 1976, and 1978. These targets can be, for example, cell surface proteins, cytosolic proteins, or secreted proteins, as well as nucleic acid molecules that encode these proteins.

The terms "protein" and "polypeptide" are used herein interchangeably. Exemplary CAT proteins/polypeptides are provided as SEQ ID NOS:1-722, 1975, and 1977. A "peptide" typically refers to a fragment of a protein/polypeptide. Thus, peptides are interchangeably referred to as fragments. Exemplary CAT peptides are provided as SEQ ID NOS:1282-1974. SEQ ID NOS:1282-1974 are fragments of SEQ ID NOS:1-722, 1975, and 1977 (in Table 1, the range of numbers in parentheses following each peptide SEQ ID NO represents the amino acid residues of the location of the peptide within its corresponding protein).

References herein to proteins, peptides, nucleic acid molecules, and antibodies typically are not limited to the full-size or full-length molecule, but also can encompass fragments of these molecules (unless a particular sequence or structure is explicitly stated).

Exemplary embodiments of the invention, which are discussed in greater detail below, provide antibodies, proteins, immunogenic peptides (e.g., peptides which induce a T-cell response), or other biomolecules, as well as small molecules, nucleic acid agents (e.g., RNAi and antisense nucleic acid agents), and other compositions that modulate the targets (e.g., agonists and antagonists), such as by binding to or otherwise interacting with or affecting the targets. These compositions can be used for assessing, treating, and preventing diseases, especially cancer, particularly the cancers identified in Table 1 (as indicated for each peptide) and/or Table 3, as well as other uses. Moreover, the invention provides methods for assessing, treating, and preventing diseases such as these based on CAT, such as by using these compositions. Further provided are methods of screening for agents that modulate CAT, such as by affecting the function, activity, and/or expression level ("expression level" may be interchangeably referred to as "abundance level" or "level") of CAT, and agents identified by these screening methods.

Exemplary embodiments of the invention also provide methods of modulating cell function. In particular, the invention provides methods of modulating cell proliferation and/or apoptosis. For example, for cancer/tumor cells, the invention provides methods of inhibiting cell proliferation and/or stimulating apoptosis. Such methods can be applied to the treatment of diseases, especially cancer.

Exemplary embodiments of the invention further provide methods of determining or predicting effectiveness or response to a particular treatment, and methods of selecting a treatment for an individual. For example, targets that are differentially expressed by cells that are more or less responsive or resistant to a particular treatment, such as a cancer treatment, are useful for determining or predicting effectiveness or response to the treatment or for selecting a treatment for an individual. Exemplary embodiments of the invention also provide methods of selecting individuals for a clinical trial of a therapeutic agent. For example, the targets can be used to identify individuals for inclusion in a clinical trial who are more likely to respond to a particular treatment. Alternatively, the targets can be used to exclude individuals from a clinical trial who are less likely to respond to a particular treatment or who are more likely to experience toxic or other undesirable side effects from a particular treatment.

Further exemplary embodiments of the invention are described in greater detail below.

Cancer-Associated Targets (CAT) as Cancer Stem Cell (CSC) Targets

The CAT proteins and encoding nucleic acid molecules provided in Table 1 and/or Table 3 are expressed by cancer stem cells ("CSCs") and therefore are useful as CSC targets (as exemplified in the figures for certain targets). Thus, the cancer-associated targets ("CAT") provided herein may be interchangeably referred to herein as CSC targets. Because the CAT provided herein are expressed by cancer stem cells, the targets provided herein are particularly useful for cancer stem cell-related purposes, such as for specifically targeting cancer stems cells (e.g., for therapeutic or diagnostic purposes) or for detecting, isolating, and/or labeling cancer stem cells. For example, the targets provided herein are particularly useful as therapeutic targets for cancer. A therapeutic agent can specifically target a CAT protein, such as in a heterogenous tumor cell population, in order to more effectively and efficiently (e.g., by enabling the use of a lower dose of a therapeutic agent, thereby minimizing side effects such as toxicity) treat a cancer by targeting a cancer stem cell.

CSCs may be cultured under conditions (e.g., using a serum-free culture medium such as media designated for human embryonic stem cells) in which the CSCs proliferate as non-adherent 3-dimensional ("3D") spheres, closely mimicking in vivo tumor growth. Hence, CSCs may be interchangeably referred to herein as "cancer spheroid cells", "spheroids", or "tumorospheres". These 3D cultures of CSCs, which can be stably maintained in vitro, are useful for therapeutic target discovery and drug testing, among other uses.

Typical cancer cells or heterogeneous populations of cancer cells that are not CSCs (i.e., non-stem cell-like cancer cells) may be interchangeably referred to herein as "differentiated", "adherent", or "parental" cells (although "parental" cells typically more specifically refer to differentiated/adherent cells from which cancer stem cells are derived from), or as "counterparts" to cancer stem cells.

In certain exemplary embodiments of the invention, the CAT proteins or encoding nucleic acid molecules provided in Table 1 and/or Table 3 are used for selectively targeting CSCs (such as in a tumor or other heterogenous population of cancer cells), such as for therapeutic, preventative, diagnostic, or prognostic purposes. For example, by selectively targeting a CSC target provided herein (e.g., with an antibody or small molecule compound that selectively binds to a protein provided herein, or a nucleic acid agent such as an RNAi or antisense molecule that hybridizes to a nucleic acid molecule that encodes a protein provided herein), proliferation or apoptosis of CSCs can be modulated, such as to inhibit proliferation or stimulate apoptosis of CSCs (such as for the purpose of killing CSCs).

Exemplary embodiments of the invention provide agents, such as antibodies, antibody-drug conjugates, detectably labeled antibodies, small molecule compounds, and nucleic acid agents, which selectively target the CSC targets provided herein, as well as methods of using these agents. Exemplary methods of using these agents include, but are not limited to, methods for modulating CSC proliferation or apoptosis (e.g., inhibiting CSC proliferation or stimulating CSC apoptosis), and methods for the treatment, prevention, or diagnosis of cancer (such as may be achieved by selectively targeting CSCs).

The CSC targets provided herein are also useful to screen drug candidates for agents that selectively bind, interact with, or otherwise target CSCs. Accordingly, certain exemplary embodiments of the invention provide screening methods that utilize the CSC targets provided herein, as well as agents identified using these CSC-specific drug screening methods and methods of using these agents.

The CSC targets provided herein are also useful in methods of eliciting a CSC-specific immune response. For example, the CSC targets or fragments thereof can be used in the preparation of immunogens or cancer vaccines that utilize CSC antigens, either for prophylactic or therapeutic purposes. Thus, certain exemplary embodiments of the invention provide immunogens or cancer vaccines that comprise one or more CSC targets provided herein, or fragments thereof, and methods of producing and using such immunogens or cancer vaccines.

With respect to methods of using the CSC targets provided herein, examples of various embodiments of the invention include, but are not limited to, methods for distinguishing functionally different populations of cancer cells; methods for diagnosing an individual with cancer; methods for predicting an individual's likelihood of developing cancer in the future; methods for determining the severity of cancer or predicting cancer progression (e.g., likelihood and extent of metastasis, or rapidity and extent of tumor growth); methods for determining the effects of therapeutic agents (e.g., antibodies, small molecules, proteins, nucleic acid compositions such as antisense or RNAi nucleic acids, etc.) on tumors or the interaction of these agents with CSCs; methods for selecting a therapeutic strategy (e.g., based on predicted response of the cancer to a particular therapeutic agent); methods for screening, identifying, and testing therapeutic agents that target cancer stem cells; etc.

Thus, the CSC targets are useful in the diagnosis, prognosis, treatment, or prevention of cancer, particularly by selectively targeting CSCs, or for screening for therapeutic or diagnostic agents for cancer (e.g., small molecule compounds or antibodies that selectively bind to the CSC targets), particularly therapeutic or diagnostic agents that target CSCs. Agents that target CSC targets, such as antibodies, antibody-drug conjugates, and small molecule compounds, can be used to inhibit proliferation or stimulate apoptosis of CSCs. Accordingly, agents such as these that target CSC targets can be used to treat cancer. Furthermore, agents that target (e.g., selectively bind to) CSC targets can be used for such purposes as, for example, diagnostic or prognostic purposes, for selecting and/or prescribing a therapeutic agent to be administered to an individual or selecting a treatment regimen for an individual, for monitoring or predicting an individual's response to a particular treatment, for monitoring cancer progression or remission, for determining or predicting cancer recurrence, or for determining a specific stage, sub-type, or other classification or characteristic of a cancer. Uses such as these can be achieved, for example, by using an agent (such as an antibody, for example, which may optionally be coupled to a detectable label) that selectively binds to a CSC target provided herein in order to, for example, determine the presence or abundance of CSCs or CSC targets in a tumor or to determine the proportion of CSCs relative to other (non-stem cell-like) cancer cells in a tumor. The CSC targets provided herein are useful for, for example, isolating or differentiating CSCs (e.g., isolating CSCs from tumor tissue samples).

CSCs can typically be isolated or cultured using a serum-free culture medium such as media designated for human embryonic stem cells. For example, CSC populations can be derived from their adherent parental cells by culturing the adherent parental cells in a serum-free culture medium such as that designated for human embryonic stem cells. Furthermore, CSC populations can typically be differentiated back to adherent cells upon exposure of the CSC populations to serum.

CSCs may demonstrate higher tumorigenic capacity or retain tumorigenicity (as assayed by an anchorage-independent assay) compared with their adherent cell counterparts. Furthermore, CSCs may demonstrate increased resistance relative to their adherent counterparts to chemotherapeutic drugs (e.g., irinotecan, a first line treatment for colon cancer), whereas their adherent counterparts undergo apoptosis and/or demonstrate growth inhibition when exposed to the same drug.

1. CAT Proteins

Exemplary embodiments of the invention provide isolated CAT proteins that consist of, consist essentially of, or comprise the amino acid sequences of SEQ ID NOS:1-722, 1975, and 1977 (which are encoded by the nucleotide sequences of SEQ ID NOS:723-1281, 1976, and 1978, respectively), as well as all obvious variants of these proteins and nucleic acid molecules that are within the art to make and use. Examples of such obvious variants include, but are not limited to, naturally-occurring allelic variants, pre-processed or mature processed forms of a protein, non-naturally occurring recombinantly-derived variants, orthologs, and paralogs. Such variants can readily be generated using art-known techniques in the fields of recombinant nucleic acid technology and protein biochemistry.

A protein is said to be "isolated" or "purified" when it is substantially free of cellular material or free of chemical precursors or other chemicals. CAT proteins can be purified to homogeneity or other degrees of purity. The level of purification can be based on the intended use. The primary consideration is that the preparation allows for the desired function of the protein, even if in the presence of considerable amounts of other components.

In some uses, "substantially free of cellular material" includes preparations of a protein having less than about 30% (by dry weight) other proteins (i.e., contaminating protein), less than about 20% other proteins, less than about 10% other proteins, or less than about 5% other proteins. When the protein is recombinantly produced, it can also be substantially free of culture medium, i.e., culture medium represents less than about 20% of the volume of the protein preparation.

The language "substantially free of chemical precursors or other chemicals" includes preparations of a protein in which the protein is separated from chemical precursors or other chemicals that are involved in the protein's synthesis. In one embodiment, the language "substantially free of chemical precursors or other chemicals" includes preparations of a CAT protein having less than about 30% (by dry weight) chemical precursors or other chemicals, less than about 20% chemical precursors or other chemicals, less than about 10% chemical precursors or other chemicals, or less than about 5% chemical precursors or other chemicals.

Isolated CAT proteins can be purified from cells that naturally express it, purified from cells that have been altered to express it (recombinant), or synthesized using known protein synthesis methods (e.g., Sambrook et al., Molecular Cloning: A Laboratory Manual. 3rd. ed., Cold Spring Harbor Laboratory Press, Cold Spring Harbor, N.Y., (2001)). For example, a nucleic acid molecule encoding a CAT protein can be cloned into an expression vector, the expression vector introduced into a host cell, and the protein expressed in the host cell. The protein can then be isolated from the cells by an appropriate purification scheme using standard protein purification techniques.

A CAT protein or fragment thereof can be attached to heterologous sequences to form chimeric or fusion proteins. Such chimeric and fusion proteins comprise a protein operatively linked to a heterologous protein having an amino acid sequence not substantially homologous to the protein. "Operatively linked" indicates that the protein and the heterologous protein are fused in-frame. The heterologous protein can be fused to the N-terminus or C-terminus of the protein.

In some uses, the fusion protein does not affect the activity of the protein per se. For example, the fusion protein can include, but is not limited to, beta-galactosidase fusions, yeast two-hybrid GAL fusions, poly-His fusions, MYC-tagged, HI-tagged, and Ig fusions. Such fusion proteins, particularly poly-His fusions, can facilitate the purification of recombinant CAT proteins. In certain host cells (e.g., mammalian host cells), expression and/or secretion of a protein can be increased by using a heterologous signal sequence.

A chimeric or fusion CAT protein can be produced by standard recombinant DNA techniques. For example, DNA fragments coding for different protein sequences can be ligated together in-frame in accordance with conventional techniques. In another embodiment, a fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (Ausubel et al., Current Protocols in Molecular Biology, 1992-2006). Moreover, many expression vectors are commercially available that already encode a fusion moiety (e.g., a GST protein). A CAT-encoding nucleic acid can be cloned into such an expression vector such that the fusion moiety is linked in-frame to the CAT protein.

To determine the percent identity of two amino acid sequences or two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In an exemplary embodiment, at least 30%, 40%, 50%, 60%, 70%, 80%, or 90% or more of the length of a reference sequence can be aligned for comparison purposes. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps, and the length of each gap, that are introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, N.J., 1994; Sequence Analysis in Molecular Biology, von Heinje, G., Academic Press, 1987; and Sequence Analysis Primer, Gribskov, M. and Devereux, J., eds., Stockton Press, New York, 1991). In an exemplary embodiment, the percent identity between two amino acid sequences is determined using the Needleman and Wunsch (*J. Mol. Biol.* (48):444-453 (1970)) algorithm which has been incorporated into the GAP program in the GCG software package, using either a Blossom 62 matrix or a PAM250 matrix, a gap weight of 16, 14, 12, 10, 8, 6, or 4, and a length weight of 1, 2, 3, 4, 5, or 6. In another exemplary embodiment, the percent identity between two nucleotide sequences can be determined using the GAP program in the GCG software package (Devereux et al., *Nucleic Acids Res.* 12(1):387 (1984)) using a NWSgapdna.CMP matrix and a gap weight of 40, 50, 60, 70, or 80, and a length weight of 1, 2, 3, 4, 5, or 6. In another exemplary embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12, and a gap penalty of 4.

The sequences of the proteins and nucleic acid molecules of the invention can further be used as a "query sequence" to perform a search against sequence databases to, for example, identify other protein family members or related sequences.

Such searches can be performed using the NBLAST and XBLAST programs (version 2.0) of Altschul et al. (*J. Mol. Biol.* 215:403-10 (1990)). BLAST nucleotide searches can be performed with the NBLAST program, score=100, wordlength=12, to obtain nucleotide sequences homologous to the query nucleic acid molecule. BLAST protein searches can be performed with the XBLAST program, score=50, wordlength=3, to obtain amino acid sequences homologous to the query proteins. To obtain gapped alignments for comparison purposes, Gapped BLAST can be utilized as described in Altschul et al. (*Nucleic Acids Res.* 25(17):3389-3402 (1997)). When utilizing BLAST and gapped BLAST programs, the default parameters of the respective programs (e.g., XBLAST and NBLAST) can be used.

As used herein, two proteins (or a region or domain of the proteins) have significant homology/identity (also referred to as substantial homology/identity) when the amino acid sequences are typically at least about 70-80%, 80-90%, 90-95%, 96%, 97%, 98%, or 99% identical A significantly homologous amino acid sequence can be encoded by a nucleic acid molecule that hybridizes to a CAT protein-encoding nucleic acid molecule under stringent conditions, as more fully described below.

Orthologs of a CAT protein typically have some degree of significant sequence homology to at least a portion of a CAT protein and are encoded by a gene from another organism. Preferred orthologs are isolated from mammals, preferably non-human primates, for the development of human therapeutic targets and agents. Such orthologs can be encoded by a nucleic acid molecule that hybridizes to a CAT protein-encoding nucleic acid molecule under moderate to stringent conditions, as more fully described below, depending on the degree of relatedness of the two organisms yielding the proteins.

Non-naturally occurring variants of the CAT proteins can readily be generated using recombinant techniques. Such variants include, but are not limited to, deletions, additions, and substitutions in the amino acid sequence of the CAT protein. For example, one class of substitutions is conserved amino acid substitutions. Such substitutions are those that substitute a given amino acid in a CAT protein by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306-1310 (1990).

Variant CAT proteins can be fully functional or can lack function in one or more activities, e.g., ability to bind substrate, ability to phosphorylate substrate, ability to mediate signaling, etc. Fully functional variants typically contain only conservative variations or variation in non-critical residues or in non-critical regions.

Non-functional variants typically contain one or more non-conservative amino acid substitutions, deletions, insertions, inversions, or truncations, or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081-1085 (1989)). The latter procedure introduces single alanine mutations at every residue in the molecule. The resulting mutant molecules are then tested for biological activity or in assays such as in vitro proliferative activity. Sites that are critical for binding partner/substrate binding can also be determined by structural analysis such as crystallization, nuclear magnetic resonance, or photoaffinity labeling (Smith et al., *J. Mol. Biol.* 224:899-904 (1992); de Vos et al., *Science* 255:306-312 (1992)).

Exemplary embodiments of the invention provide fragments of a CAT, and peptides that comprise and consist of such fragments. An exemplary fragment typically comprises at least about 5, 6, 8, 10, 12, 14, 16, 18, 20 or more contiguous amino acid residues of a CAT protein. Such fragments can be chosen based on the ability to retain one or more of the biological activities of CAT or can be chosen for the ability to perform a function, e.g., bind a substrate or act as an immunogen. Particularly important fragments are biologically active fragments, such as peptides that are, for example, about 8 or more amino acids in length. Such fragments can include a domain or motif of a CAT, e.g., an active site, a transmembrane domain, or a binding domain. Further, possible fragments include, but are not limited to, soluble peptide fragments and fragments containing immunogenic structures. Domains and functional sites can readily be identified, for example, by computer programs well known and readily available to those of skill in the art (e.g., PROSITE analysis).

Proteins can contain amino acids other than the 20 amino acids commonly referred to as the 20 naturally-occurring amino acids. Further, many amino acids, including the terminal amino acids, can be modified by natural processes, such as processing and other post-translational modifications, or by chemical modification techniques well known in the art. Common modifications that occur naturally in proteins are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, tRNA-mediated addition of amino acids to proteins such as arginylation, and ubiquitination.

Such modifications are well known to those of skill in the art and have been described in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins-Structure and Molecular Properties, 2nd Ed., T. E. Creighton, W.H. Freeman and Company, New York (1993). Many detailed reviews are available on this subject, such as by Wold (Post-translational Covalent Modification of Proteins, B. C. Johnson, Ed., Academic Press, New York 1-12 (1983)); Seifter et al. (Meth. Enzymol. 182: 626-646 (1990)); and Rattan et al. (Ann. N.Y. Acad. Sci. 663:48-62 (1992)).

Accordingly, exemplary CAT proteins and fragments thereof of the invention can also encompasses derivatives or analogs in which, for example, a substituted amino acid residue is not one encoded by the genetic code, in which a substituent group is included, in which a mature CAT is fused with another composition, such as a composition to increase the half-life of a CAT (e.g., polyethylene glycol or albumin), or in which additional amino acids are fused to a mature CAT, such as a leader or secretory sequence or a sequence for purification of a mature CAT or a pro-protein sequence.

2. Antibodies to CAT Proteins

Exemplary embodiments of the invention provide antibodies to CAT proteins, including, for example, monoclonal and polyclonal antibodies; chimeric, humanized, and fully human antibodies; and antigen-binding fragments and variants thereof, as well as other embodiments.

Antibodies that selectively bind to a CAT protein can be made using standard procedures known to those of ordinary skills in the art. The term "antibody" is used in the broadest sense, and specifically covers, for example, monoclonal antibodies, polyclonal antibodies, multispecific antibodies (e.g., bispecific antibodies), chimeric antibodies, humanized antibodies, fully human antibodies, and antibody fragments (e.g., Fab, F(ab')$_2$, Fv and Fv-containing binding proteins), so long as they exhibit the desired biological activity. Antibodies (Ab's) and immunoglobulins (Ig's) are glycoproteins typically having the same structural characteristics. While antibodies exhibit binding specificity to a specific antigen, immunoglobulins include both antibodies and other antibody-like molecules that lack antigen specificity. Antibodies can be of the IgG, IgE, IgM, IgD, and IgA class or subclass thereof (e.g., IgG1, IgG2, IgG3, IgG4, IgA1 and IgA2). Antibodies may be interchangeably referred to as "antigen-binding molecules".

The term "monoclonal antibody", as used herein, refers to an antibody obtained from a population of substantially homogeneous antibodies, i.e., the individual antibodies comprising the population are substantially identical except for possible naturally occurring mutations that may be present in minor amounts. Monoclonal antibodies are highly specific and are typically directed against a single antigenic site. Furthermore, in contrast to polyclonal antibody preparations, which typically include different antibodies directed against different determinants (epitopes), each monoclonal antibody is typically directed against a single determinant on an antigen. In addition to their specificity, monoclonal antibodies are advantageous in that substantially homogenous antibodies can be produced by a hybridoma culture which is uncontaminated by other immunoglobulins or antibodies. The modifier "monoclonal" antibody indicates the character of the antibody as being obtained from a substantially homogeneous population of antibodies, and is not to be construed as requiring production of the antibody by any particular method. For example, monoclonal antibodies can be made by hybridoma methods such as described by Kohler and Milstein, Nature 256: 495-497 (1975), by recombinant methods (e.g., as described in U.S. Pat. No. 4,816,567), or can be isolated from phage antibody libraries such as by using the techniques described in Clackson et al., Nature 352: 624-628 (1991) or Marks et al., J. Mol. Biol. 222: 581-597 (1991).

"Humanized" forms of non-human (e.g., murine or rabbit) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Typically, humanized antibodies are human immunoglobulins (a recipient antibody) in which residues from a complementarity determining regions ("CDR") of the recipient are replaced by residues from a CDR of a non-human species (a donor antibody) such as mouse, rat, or rabbit having the desired specificity, affinity, and capacity. In some instances, Fv framework residues of the human immunoglobulin are replaced by corresponding non-human residues. Furthermore, a humanized antibody may comprise residues which are found neither in the recipient antibody nor in the imported CDR or framework region (FR) sequences. These modifications can be made to further refine and optimize antibody performance. In general, a humanized antibody can comprise substantially all of at least one, and typically two, variable domains, in which all or substantially all of the CDRs correspond to those of a non-human immunoglobulin and all or substantially all of the FRs are those of a human immunoglobulin consensus sequence. A humanized antibody can also comprise at least a portion of an immunoglobulin constant region (Fc), typically that of a human immunoglobulin. For further details concerning humanized antibodies, see: Jones et al., Nature 321:522-525 (1986); Reichmann et al., Nature 332:323-327 (1988); Presta, Curr. Op. Struct. Biol. 2:593-596 (1992); Queen et al., U.S. Pat. Nos. 5,530,101; 5,585,089; 5,693,762; and 6,180,370; and Winter, U.S. Pat. No. 5,225,539.

Antibodies, as used herein, include antibody fragments, particularly antigen-binding fragments, as well as other modified antibody structures and antigen-binding scaffolds (such as modified antibody structures that are smaller or have less than all domains or chains compared with a typical naturally occurring, full-size human antibody). Examples of antibody fragments and other modified antibody structures and antigen-binding scaffolds are known in the art by such terms as minibodies (e.g., U.S. Pat. No. 5,837,821), Nanobodies (llama heavy chain antibodies; Ablynx, Ghent, Belgium), Adnectins (fibronectin domains; Adnexus Therapeutics, Waltham, Mass.), Affibodies (protein-binding domain of *Staphylococcus aureus* protein A; Affibody, Stockholm, Sweden), peptide aptamers (synthetic peptides; Aptanomics, Lyon, France), Avimers (A-domains derived from cell surface receptors; Avidia, Mountain View, Calif. (acquired by Amgen)), Transbodies (transferrin; BioRexis Pharmaceuticals, King of Prussia, Pa. (acquired by Pfizer)), trimerized tetranectin domains (Borean Pharma, Aarhus, Denmark), Domain antibodies (heavy or light chain antibodies; Domantis, Cambridge, UK (acquired by GlaxoSmithKline)), Evibodies (derived from V-like domains of T-cell receptors CTLA-4, CD28 and inducible T-cell costimulator; EvoGenix Therapeutics, Sydney, Australia), scFV fragments (stable single chain antibody fragments; ESBATech, Zurich, Switzerland), Unibodies (monovalent IgG4 mAbs fragments; Genmab, Copenhagen, Denmark), BiTEs (bispecific, T-cell activating single-chain antibody fragments; Micromet, Munich, Germany), DARPins (designed ankyrin repeat proteins; Molecular Partners, Zurich, Switzerland), Anticalins (derived from lipocalins; Pieris, Freising-Weihenstephan, Germany), Affilins (derived from human lens protein gamma crystalline; Scil Proteins, Halle, Germany), and SMIPs (small modular immunopharmaceuticals; Trubion Pharmaceuticals, Seattle, Wash.) (Sheridan, *Nature Biotechnology*, 2007 April; 25(4):365-6).

An "isolated" or "purified" antibody is one that has been identified and separated and/or recovered from a component of the environment in which it is produced. Contaminant components of its production environment are materials that would interfere with diagnostic or therapeutic uses for the antibody, and may include enzymes, hormones, and other proteinaceous or nonproteinaceous solutes. In exemplary embodiments, the antibody can be purified as measurable by any of at least three different methods: 1) to greater than 95% by weight of antibody as determined by the Lowry method, preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or silver stain. Isolated antibody can include an antibody in situ within recombinant cells since at least one component of the antibody's natural environment will not be present. Ordinarily, however, an isolated antibody can be prepared by at least one purification step.

An "antigenic region", "antigenic determinant", or "epitope" includes any protein determinant capable of specific binding to an antibody. This is the site on an antigen to which each distinct antibody molecule binds. Epitopic determinants can be active surface groupings of molecules such as amino acids or sugar side chains and may have specific three-dimensional structural characteristics or charge characteristics.

"Antibody specificity" refers to an antibody that has a stronger binding affinity for an antigen from a first subject species than it has for a homologue of that antigen from a second subject species. Typically, an antibody "binds specifically" to a human antigen (e.g., has a binding affinity (Kd) value of no more than about $1 \times 10^{-7}$ M, preferably no more than about $1 \times 10^{-8}$ M, and most preferably no more than about $1 \times 10^{-9}$ M) but has a binding affinity for a homologue of the antigen from a second subject species which is at least about 50-fold, or at least about 500-fold, or at least about 1000-fold, weaker than its binding affinity for the human antigen. The antibodies can be of any of the various types of antibodies as described herein, such as humanized or fully human antibodies.

An antibody "selectively" or "specifically" binds a target protein when the antibody binds the target protein and does not significantly bind to unrelated proteins. An antibody can still be considered to selectively or specifically bind a target protein even if it also binds to other proteins that are not substantially homologous with the target protein as long as such proteins share homology with a fragment or domain of the target protein. In this case, it would be understood that antibody binding to the target protein is still selective despite some degree of cross-reactivity.

Exemplary embodiments of the invention provide an "antibody variant", which refers to an amino acid sequence variant of an antibody wherein one or more of the amino acid residues have been modified. Such variants necessarily have less than 100% sequence identity with the amino acid sequence of the antibody, and have at least 75%, 80%, 85%, 90%, 95%, 96%, 97%, 98%, or 99% amino acid sequence identity with the amino acid sequence of either the heavy or light chain variable domain of the antibody.

The term "antibody fragment" refers to a portion of a full-length antibody, including the antigen binding or variable region or the antigen-binding portion thereof. Examples of antibody fragments include Fab, Fab', F(ab')$_2$ and Fv fragments. Papain digestion of antibodies typically produces two identical antigen binding fragments, called the Fab fragment, each with a single antigen binding site, and a residual "Fc" fragment. Pepsin treatment typically yields an F(ab')$_2$ fragment that has two antigen binding fragments which are capable of crosslinking antigen, and a residual other fragment (which is termed pFc'). Examples of additional antigen-binding fragments can include diabodies, triabodies, tetrabodies, single-chain Fv, single-chain Fv-Fc, SMIPs, and multispecific antibodies formed from antibody fragments. A "functional fragment", with respect to antibodies, typically refers to an Fv, F(ab), F(ab')$_2$ or other antigen-binding fragments comprising one or more CDRs that has substantially the same antigen-binding specificity as an antibody.

An "Fv" fragment is an example of an antibody fragment that contains a complete antigen recognition and binding site. This region typically consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen.

An "Fab" fragment (also designated as "F(ab)") also contains the constant domain of the light chain and the first constant domain (CH1) of the heavy chain. Fab' fragments differ from Fab fragments by the addition of a few residues at the carboxyl terminus of the heavy chain CH1 domain, including one or more cysteines from the antibody hinge region. Fab'-SH is the designation for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

A "single-chain Fv" or "scFv" antibody fragment contains $V_H$ and $V_L$ domains, wherein these domains are present in a single polypeptide chain. Typically, the Fv polypeptide further comprises a polypeptide linker between the $V_H$ and $V_L$ domains that enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994). A single chain Fv-Fc is an scFv linked to a Fc region.

A "diabody" is a small antibody fragment with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., *Proc. Natl. Acad. Sci. USA* 90:6444-6448 (1993). Triabodies, tetrabodies and other antigen-binding antibody fragments have been described by Hollinger and Hudson, 2005, *Nature Biotechnology* 23:1126.

A "small modular immunopharmaceutical" (or "SMIP") is a single-chain polypeptide including a binding domain (e.g., an scFv or an antigen binding portion of an antibody), a hinge region, and an effector domain (e.g., an antibody Fc region or a portion thereof). SMIPs are described in published U.S. Patent Application No. 20050238646.

Many methods are known for generating and/or identifying antibodies to a given target protein. Several such methods are described by Kohler et al., 1975, *Nature* 256: 495-497; Lane, 1985, *J. Immunol. Meth.* 81:223-228; Harlow et al., 1988, Antibodies: A Laboratory Manual. Cold Spring Harbor Laboratory Press; Harlow et al., 1998, Using Antibodies, Cold Spring Harbor Press; Zhong et al., 1997, *J. Indust. Microbiol. Biotech.* 19(1):71-76; and Berry et al., 2003, Hybridoma and Hybridomics 22(1): 23-31.

Polyclonal antibodies can be prepared by any known method or modifications of these methods, including obtaining antibodies from patients. In certain exemplary methods for generating antibodies such as polyclonal antibodies, an isolated protein can be used as an immunogen which is administered to a mammalian organism, such as a rat, rabbit, or mouse. For example, a complex of an immunogen such as a CAT protein (or fragment thereof) and a carrier protein can be prepared and an animal immunized by the complex. Serum or plasma containing antibodies against the protein can be recovered from the immunized animal and the antibodies separated and purified (in the same manner as for monoclonal antibodies, for example). The gamma globulin fraction or the IgG antibodies can be obtained, for example, by use of saturated ammonium sulfate or DEAE SEPHADEX, or other techniques known to those skilled in the art. The antibody titer in the antiserum can be measured in the same manner as in the supernatant of a hybridoma culture.

A full-length CAT protein, an antigenic peptide fragment, or a fusion protein thereof, can be used as an immunogen. A protein used as an immunogen is not limited to any particular type of immunogen. In one aspect, antibodies can be prepared from regions or discrete fragments (e.g., functional domains, extracellular domains, or portions thereof) of a CAT protein. Antibodies can be prepared from any region of a protein as described herein. In particular, the proteins can be selected from the group consisting of SEQ ID NOS:1-722, 1975, and 1977 and fragments thereof. An antigenic fragment can typically comprise at least 8, 10, 12, 14, 16, or more contiguous amino acid residues, for example. Such fragments can be selected based on a physical property, such as fragments that correspond to regions located on the surface of a protein (e.g., hydrophilic regions) or can be selected based on sequence uniqueness.

Antibodies can also be produced by inducing production in a lymphocyte population or by screening antibody libraries or panels of highly specific binding reagents, such as disclosed in Orlandi et al. (*Proc. Natl. Acad. Sci.* 86:3833-3837 (1989)) or Winter et al. (*Nature* 349:293-299 (1991)). A protein can be used in screening assays of phagemid or B-lymphocyte immunoglobulin libraries to identify antibodies having a desired specificity. Numerous protocols for competitive binding or immunoassays using either polyclonal or monoclonal antibodies with established specificities are well known in the art (e.g., Smith, *Curr. Opin. Biotechnol.* 2: 668-673 (1991)).

Antibodies can also be generated using various phage display methods known in the art. In representative phage display methods, functional antibody domains are displayed on the surface of phage particles which carry nucleic acid molecules that encode the antibody domains. In particular, such phage can be utilized to display antigen-binding domains expressed from a repertoire or combinatorial antibody library (e.g., human or murine). Phage expressing an antigen binding domain that binds an antigen of interest can be selected or identified with the antigen, e.g., using labeled antigen or antigen bound or captured to a solid surface or bead. Phage used in methods such as these can typically be filamentous phage including fd and M13 binding domains expressed from phage with Fab, Fv, or disulfide stabilized Fv antibody domains recombinantly fused to either the phage gene III or gene VIII protein. Examples of phage display methods that can be used to make antibodies include methods described in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Antibodies, antigen binding fragments, and/or antibody variants can be produced by recombinant and genetic engineering methods well known in the art. For example, methods of expressing heavy and light chain genes in *E. coli* are described in PCT publication numbers WO901443, WO901443, and WO9014424, and in Huse et al., 1989 *Science* 246:1275-1281. When using recombinant techniques, such as to produce an antibody variant, the antibody variant can be produced intracellularly, in the periplasmic space, or directly secreted into the medium. If an antibody variant is produced intracellularly, as a first step, the particulate debris, either host cells or lysed fragments, can be removed, for example, by centrifugation or ultrafiltration. Carter et al. (*Bio/Technology* 10: 163-167 (1992)) describe a procedure for isolating antibodies that are secreted to the periplasmic space of *E. coli*. Briefly, cell paste can be thawed in the presence of sodium acetate (pH 3.5), EDTA, and phenylmethylsulfonylfluoride (PMSF) over about 30 minutes. Cell debris can be removed by centrifugation. Where an antibody variant is secreted into the medium, supernatants from such expression systems can first be concentrated using a commercially available protein concentration filter (e.g., an Amicon or Millipore PELLICON ultrafiltration unit). A protease inhibitor such as PMSF can be included in any of the foregoing steps to inhibit proteolysis, and antibiotics can be included to prevent the growth of contaminating microorganisms.

An antibody composition prepared from cells can be purified using, for example, affinity chromatography, hydroxylapatite chromatography, gel electrophoresis, and/or dialysis. The suitability of protein A as an affinity ligand typically depends on the species and isotype of the immunoglobulin Fc domain of an antibody. Protein A can be used to purify antibodies that are based on human delta1, delta2, or delta4 heavy chains (Lindmark et al., *J. Immunol Meth.* 62: 1-13 (1983)). Protein G can be used for all mouse isotypes and for human delta3 (Guss et al., *EMBO J.* 5: 1567-1575 (1986)). The matrix to which the affinity ligand is attached can be, for example, agarose or mechanically stable matrices such as controlled pore glass or poly(styrenedivinyl)benzene. Where the antibody comprises a CH3 domain, the BAKERBOND ABX™ resin (J. T. Baker, Phillipsburg, N.J.) can be used for purification. Other exemplary techniques for antibody purification include, but are not limited to, fractionation on an ion-exchange column, ethanol precipitation, reverse phase HPLC, chromatography on silica, chromatography on heparin hepharos, chromatography on an anion or cation exchange resin (such as a polyaspartic acid column), chromatofocusing, SDS-PAGE, and ammonium sulfate precipitation.

Following any preliminary purification step(s), contaminants in a mixture containing an antibody of interest can be removed by low pH hydrophobic interaction chromatography using an elution buffer at a pH between about 2.5-4.5, preferably performed at low salt concentrations (e.g., from about 0-0.25M salt).

Full-length antibodies, as well as antibody fragments, can also be expressed and isolated from bacteria such as *E. coli*, such as described in Mazor et al., "Isolation of engineered, full-length antibodies from libraries expressed in *Escherichia coli*", *Nat Biotechnol.* 2007 May; 25(5):563-5 and Sidhu, "Full-length antibodies on display", *Nat Biotechnol.* 2007 May; 25(5):537-8.

Further details regarding antibodies are set forth in the following U.S. Pat. Nos. 6,248,516 (Winter et al.); 6,291,158 (Winter et al.); 5,885,793 (Griffiths et al.); 5,969,108 (McCafferty et al.); 5,939,598 (Kucherlapati et al.); 4,816,397 (Boss et al.); 4,816,567 (Cabilly et al.); 6,331,415 (Cabilly et al.); 5,770,429 (Lonberg et al.); 5,639,947 (Hiatt et al.); and 5,260,203 (Ladner et al.), each of which is incorporated herein by reference, and in the following published U.S.

patent applications: US20040132101 (Lazar et al.), US20050064514 (Stavenhagen et al.), US20040261148 (Dickey et al.), and US20050014934 (Hinton et al.), each of which is incorporated herein by reference. Antibody engineering is further described in Jain et al., "Engineering antibodies for clinical applications", *Trends Biotechnol.* 2007 July; 25(7):307-16.

3. Antibody-Drug Conjugates to CAT Proteins

An antibody against CAT can be coupled (e.g., covalently bonded) to a suitable therapeutic agent (as further discussed herein) either directly or indirectly (e.g., via a linker group). A direct reaction between an antibody and a therapeutic agent is possible when each possesses a substituent capable of reacting with the other. For example, a nucleophilic group, such as an amino or sulfhydryl group, on one molecule may be capable of reacting with a carbonyl-containing group, such as an anhydride or an acid halide, or with an alkyl group containing a good leaving group (e.g., a halide) on the other molecule.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

A variety of bifunctional or polyfunctional reagents, both homo- and hetero-functional (such as those described in the catalog of the Pierce Chemical Co., Rockford, Ill.), can be employed as the linker group. Coupling can be effected, for example, through amino groups, carboxyl groups, sulfhydryl groups, or oxidized carbohydrate residues (e.g., U.S. Pat. No. 4,671,958).

Where a therapeutic agent is more potent when free from the antibody portion of an immunoconjugate, it may be desirable to use a linker group that is cleavable during or upon internalization into a cell. A number of different cleavable linker groups have been described. Mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), by protease cleavable linker (e.g., U.S. Pat. No. 6,214,345), and by acid-catalyzed hydrolysis (e.g., U.S. Pat. No. 4,569,789).

It may be desirable to couple more than one agent to an antibody. Multiple molecules of an agent can be coupled to one antibody molecule, and more than one type of agent can be coupled to the same antibody. For example, about 1, 2, 4, 6, 8, 10, 12, 14, 16, 18, 20, or 22 (or any other number in-between) molecules of therapeutic agents can be coupled to an antibody. The average number or quantitative distribution of therapeutic agent molecules per antibody molecule in a preparation of conjugation reactions can be determined by conventional means such as mass spectroscopy, ELISA, or HPLC. Separation, purification, and characterization of homogeneous antibody-drug conjugates having a certain number of therapeutic agents conjugated thereto can be achieved by means such as reverse phase HPLC or electrophoresis (see, e.g., Hamblett et al., *Clinical Cancer Res.* 10:7063-70 (2004).

Examples of suitable therapeutic agents that can be conjugated to an antibody include, but are not limited to, chemotherapeutic agents (e.g., cytotoxic or cytostatic agents or immunomodulatory agents), radiotherapeutic agents, therapeutic antibodies, small molecule drugs, peptide drugs, immunomodulatory agents, differentiation inducers, and toxins.

Examples of useful classes of cytotoxic or immunomodulatory agents include, but are not limited to, antitubulin agents, auristatins, DNA minor groove binders, DNA replication inhibitors, alkylating agents (e.g., platinum complexes such as cis-platin, mono(platinum), bis(platinum) and trinuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Examples of individual cytotoxic or immunomodulatory agents include, but are not limited to, androgen, anthramycin (AMC), asparaginase, 5-azacytidine, azathioprine, bleomycin, busulfan, buthionine sulfoximine, calicheamicin or calicheamicin derivatives, camptothecin or camptothecins derivatives, carboplatin, carmustine (BSNU), CC-1065, chlorambucil, cisplatin, colchicine, cyclophosphamide, cytidine arabinoside (cytarabine), cytochalasin B, dacarbazine, dactinomycin (formerly actinomycin), daunorubicin, decarbazine, docetaxel, doxorubicin, etoposide, estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16, and VM-26.

Examples of other suitable cytotoxic agents include, but are not limited to, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, a maytansinoid, discodermolide, eleutherobin, and mitoxantrone.

Examples of other suitable agents include, but are not limited to, radionuclides, differentiation inducers, drugs, toxins, and derivatives thereof. Exemplary radionuclides include $^{90}$Y, $^{123}$I, $^{125}$I, $^{131}$I, $^{186}$Re, $^{188}$Re, $^{211}$At and $^{212}$Bi. Exemplary drugs include methotrexate, and pyrimidine and purine analogs. Exemplary differentiation inducers include phorbol esters and butyric acid. Exemplary toxins include ricin, abrin, diptheria toxin, cholera toxin, gelonin, *Pseudomonas* exotoxin, *Shigella* toxin, and pokeweed antiviral protein.

In some embodiments, the therapeutic agent used in an antibody-drug conjugate is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophysins, cemadotin, maytansinoid, combretastatins, discodermolide, and eleutherobin.

In certain embodiments, the cytotoxic agent is a maytansinoid, another group of anti-tubulin agents. For example, in specific embodiments, the maytansinoid is maytansine, DM-1 (ImmunoGen, Inc.; see also Chari et al., *Cancer Res.*

52:127-131 (1992)) or DM-4. In some embodiments, the therapeutic agent is an auristatin, such as auristatin E (also known in the art as dolastatin-10) or a derivative thereof. Typically, an auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; PCT Publication Nos WO 04/010957 and WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

4. CAT Nucleic Acid Molecules

Exemplary isolated CAT nucleic acid molecules of the invention consist of, consist essentially of, or comprise a nucleotide sequence that encodes a CAT protein of the invention, an allelic variant thereof, or an ortholog or paralog thereof, for example. As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 kilobases (KB), 4 KB, 3 KB, 2 KB, or 1 KB or less, particularly contiguous protein-encoding sequences and protein-encoding sequences within the same gene but separated by introns in the genomic sequence, and flanking nucleotide sequences that contain regulatory elements. The primary consideration is that the nucleic acid is isolated from remote and unimportant flanking sequences such that it can be subjected to the specific manipulations described herein such as recombinant expression, preparation of probes and primers, and other uses specific to the nucleic acid molecules. Moreover, an "isolated" nucleic acid molecule, such as a transcript/cDNA molecule, can be substantially free of other cellular material, or culture medium when produced by recombinant techniques, or chemical precursors or other chemicals when chemically synthesized.

A nucleic acid molecule can be fused to other coding or regulatory sequences and still be considered isolated. Isolated nucleic acid molecules can include heterologous nucleotide sequences, such as heterologous nucleotide sequences that are fused to a nucleic acid molecule by recombinant techniques. For example, recombinant DNA molecules contained in a vector are considered isolated. Further examples of isolated DNA molecules include recombinant DNA molecules maintained in heterologous host cells, or purified (partially or substantially) DNA molecules in solution. Isolated RNA molecules include in vivo or in vitro RNA transcripts of isolated DNA molecules. Isolated nucleic acid molecules further include such molecules produced synthetically.

Isolated nucleic acid molecules can encode a mature protein plus additional amino or carboxyl-terminal amino acids, or amino acids interior to the mature protein (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, additional amino acids may be processed away from the mature protein by cellular enzymes.

Isolated nucleic acid molecules include, but are not limited to, sequences encoding a CAT protein alone, sequences encoding a mature protein with additional coding sequences (such as a leader or secretory sequence (e.g., a pre-pro or pro-protein sequence)), and sequences encoding a mature protein (with or without additional coding sequences) plus additional non-coding sequences (e.g., introns and non-coding 5' and 3' sequences such as transcribed but non-translated sequences that play a role in transcription, mRNA processing (including splicing and polyadenylation signals), ribosome binding, and/or stability of mRNA). In addition, nucleic acid molecules can be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. Nucleic acid molecules, especially DNA, can be double-stranded or single-stranded. Single-stranded nucleic acid can be the coding strand (sense strand) or the non-coding strand (anti-sense strand).

Exemplary embodiments of the invention further provide isolated nucleic acid molecules that encode fragments of a CAT protein as well as nucleic acid molecules that encode obvious variants of a CAT protein. Such nucleic acid molecules may be naturally occurring, such as allelic variants (same locus), paralogs (different locus), and orthologs (different organism), or can be constructed by recombinant DNA methods or by chemical synthesis. Such non-naturally occurring variants can be made by mutagenesis techniques, including those applied to nucleic acid molecules, cells, or organisms. Accordingly, nucleic acid molecule variants can contain nucleotide substitutions, deletions, inversions, and/or insertions. Variations can occur in either or both the coding and non-coding regions, and variations can produce conservative and/or non-conservative amino acid substitutions.

A fragment of a nucleic acid molecule typically comprises a contiguous nucleotide sequence at least 8, 10, 12, 15, 16, 18, 20, 22, 25, 30, 40, 50, 100, 150, 200, 250, 500 (or any other number in-between) or more nucleotides in length. The length of a fragment can be based on its intended use. For example, a fragment can encode epitope bearing regions of a protein, or can be used as DNA probes and primers. Isolated fragments can be produced by synthesizing an oligonucleotide probe using known techniques, for example, and can optionally be labeled and used to screen a cDNA library, genomic DNA, or mRNA, for example. Primers can be used in PCR reactions to clone specific regions of a gene.

A probe/primer typically comprises substantially a purified oligonucleotide or oligonucleotide pair. An oligonucleotide typically comprises a nucleotide sequence that hybridizes under stringent conditions to at least about 8, 10, 12, 14, 15, 16, 17, 18, 19, 20, 21, 22, 23, 24, 25, 30, 40, 50 (or any other number in-between) or more contiguous nucleotides.

Allelic variants, orthologs, and homologs can be identified using methods well known in the art. These variants can comprise a nucleotide sequence encoding a protein that is typically 60-70%, 70-80%, 80-90%, 90-95%, 96%, 97%, 98%, or 99% homologous to the nucleotide sequence. Such nucleic acid molecules can readily be identified as being able to hybridize under moderate to stringent conditions, to a nucleotide sequence shown in the Sequence Listing or a fragment thereof.

As used herein, the term "hybridizes under stringent conditions" is intended to describe conditions for hybridization and washing under which nucleotide sequences encoding a protein at least 60-70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in, for example, Current Protocols in Molecular Biology, John Wiley & Sons, N.Y. (1989-2006), 6.3.1-6.3.6. One example of stringent hybridization conditions is hybridization in 6× sodium chloride/sodium citrate (SSC) at about 45° C., followed by one or more washes in 0.2×SSC, 0.1% SDS at 50-65° C. Examples of moderate to low stringency hybridization conditions are well known in the art.

Exemplary embodiments of the invention also include kits for detecting the presence of CAT nucleic acid (e.g., DNA or mRNA) in a biological sample. For example, a kit can comprise reagents such as a labeled or labelable nucleic acid and/or other agents capable of detecting CAT nucleic acid in a biological sample; means for determining the amount of CAT nucleic acid in the sample; and means for comparing the amount of CAT nucleic acid in the sample with a standard. The nucleic acid and/or other agent can be packaged in one or more suitable containers. The kit can further comprise instructions for using the kit to detect CAT nucleic acid.

5. Vectors and Host Cells

Exemplary embodiments of the invention also provide vectors containing CAT nucleic acid molecules. The term "vector" refers to a vehicle, such as a nucleic acid molecule, which can transport the CAT nucleic acid molecules. When the vector is a nucleic acid molecule, the CAT nucleic acid molecules are covalently linked to the vector nucleic acid. A vector can be, for example, a plasmid, single or double stranded phage, a single or double stranded RNA or DNA viral vector, or artificial chromosome, such as a BAC, PAC, YAC, OR MAC.

A vector can be maintained in a host cell as an extrachromosomal element where it replicates and produces additional copies of the CAT nucleic acid molecules. Alternatively, a vector can integrate into a host cell genome and produce additional copies of the CAT nucleic acid molecules when the host cell replicates.

Exemplary embodiments of the invention provide vectors for maintenance (cloning vectors) and vectors for expression (expression vectors) of the nucleic acid molecules, for example. Expression vectors can express a portion of, or all of, a protein sequence. Vectors can function in prokaryotic or eukaryotic cells or in both (shuttle vectors). Vectors also include insertion vectors, which integrate a nucleic acid molecule into another nucleic acid molecule, such as into the cellular genome (such as to alter in situ expression of a gene and/or gene product). For example, an endogenous protein-coding sequence can be entirely or partially replaced via homologous recombination with a protein-coding sequence containing one or more specifically introduced mutations.

Expression vectors can contain cis-acting regulatory regions that are operably-linked in the vector to the nucleic acid molecules such that transcription of the nucleic acid molecules is allowed in a host cell. The nucleic acid molecules can be introduced into the host cell with a separate nucleic acid molecule capable of affecting transcription. The separate nucleic acid molecule may provide, for example, a trans-acting factor interacting with the cis-regulatory control region to allow transcription of the nucleic acid molecules from the vector. Alternatively, a trans-acting factor may be supplied by a host cell. Additionally, a trans-acting factor can be produced from a vector itself. It is understood, however, that transcription and/or translation of nucleic acid molecules can occur in cell-free systems.

Regulatory sequences to which CAT nucleic acid molecules can be operably linked include, for example, promoters for directing mRNA transcription. These include, but are not limited to, the left promoter from bacteriophage, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors can also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region, a ribosome binding site for translation. Other regulatory control elements for expression include initiation and termination codons as well as polyadenylation signals. Numerous regulatory sequences useful in expression vectors are well known in the art (e.g., Sambrook et al., Molecular Cloning: A Laboratory Manual. 3rd. ed., Cold Spring Harbor Laboratory Press, Cold Spring Harbor, N.Y. (2001)).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., Molecular Cloning: A Laboratory Manual. 3rd. ed., Cold Spring Harbor Laboratory Press, Cold Spring Harbor, N.Y. (2001).

A regulatory sequence can provide constitutive expression in one or more host cells (e.g., tissue specific) or can provide for inducible expression in one or more cell types such as by temperature, nutrient additive, or exogenous factors such as a hormone or other ligand. A variety of vectors providing for constitutive and inducible expression in prokaryotic and eukaryotic hosts are well known in the art.

Nucleic acid molecules can be inserted into vector nucleic acid by well-known methodology. For example, the DNA sequence that will ultimately be expressed can be joined to an expression vector by cleaving the DNA sequence and the expression vector with one or more restriction enzymes and then ligating the fragments together. Procedures for restriction enzyme digestion and ligation are well known in the art.

A vector containing a nucleic acid molecule of interest can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells (e.g., DG44 or CHO-s), and plant cells.

As described herein, it may be desirable to express a protein as a fusion protein. Accordingly, exemplary embodiments of the invention provide fusion vectors that allow for the production of fusion proteins. Fusion vectors can, for example, increase the expression of a recombinant protein; increase the solubility of a recombinant protein, and/or aid in the purification of a protein such as by acting as a ligand for affinity purification. A proteolytic cleavage site can be introduced at the junction of the fusion moiety so that the desired protein can ultimately be separated from the fusion moiety. Proteolytic enzymes include, but are not limited to, factor Xa, thrombin, and enteroenzyme. Typical fusion expression vectors include pGEX (Smith et al., Gene 67:31-40 (1988)), pMAL (New England Biolabs, Beverly, Mass.) and pRIT5 (Pharmacia, Piscataway, N.J.), which fuse glutathione S-transferase (GST), maltose E binding protein, or protein A, respectively, to a target recombinant protein. Examples of suitable inducible non-fusion *E. coli* expression vectors include pTrc (Amann et al., Gene 69:301-315 (1988)) and pET 11d (Studier et al., Gene Expression Technology: Methods in Enzymology 185:60-89 (1990)).

Recombinant protein expression can be maximized in host bacteria by providing a genetic background wherein the host cell has an impaired capacity to proteolytically cleave the recombinant protein (Gottesman, S., Gene Expression Technology: Methods in Enzymology 185, Academic Press, San Diego, Calif. (1990), pp. 119-128). Alternatively, the sequence of a nucleic acid molecule of interest can be altered to provide preferential codon usage for a specific host cell, such as *E. coli* (Wada et al., *Nucleic Acids Res.* 20:2111-2118 (1992)).

CAT nucleic acid molecules can, for example, be expressed by expression vectors in a yeast host. Examples of vectors for expression in yeast (e.g., *S. cerevisiae*) include pYepSec1 (Baldari, et al., *EMBO J.* 6:229-234 (1987)), pMFa (Kurjan et al., *Cell* 30:933-943 (1982)), pJRY88 (Schultz et al., *Gene* 54:113-123 (1987)), and pYES2 (Invitrogen Corporation, San Diego, Calif.). Nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156-2165 (1983)) and the pVL series (Lucklow et al., *Virology* 170:31-39 (1989)). Nucleic acid molecules can also be expressed in mammalian cells using mammalian expression vectors. Examples of mammalian expression vectors include pCDM8 (Seed, B. *Nature* 329:840 (1987)), pMT2PC (Kaufman et al., *EMBO J.* 6:187-195 (1987)), and CHEF (U.S. Pat. No. 5,888,809).

The expression vectors listed herein are provided by way of example only of well-known vectors available to those of ordinary skill in the art that would be useful to express CAT nucleic acid molecules. The person of ordinary skill in the art would be aware of other vectors suitable for maintenance, propagation, and/or expression of CAT nucleic acid molecules (e.g., Sambrook et al. Molecular Cloning: A Laboratory Manual. 3rd. ed., Cold Spring Harbor Laboratory Press, Cold Spring Harbor, N.Y. (2001).

Exemplary embodiments of the invention also encompasses vectors in which CAT nucleic acid molecules are cloned into a vector in reverse orientation, but operably linked to a regulatory sequence that permits transcription of antisense RNA. Thus, an antisense transcript can be produced to all, or to a portion, of a CAT nucleic acid molecule, including coding and non-coding regions. Expression of this antisense RNA may be subject to each of the parameters described above in relation to expression of the sense RNA (e.g., regulatory sequences, constitutive or inducible expression, tissue-specific expression).

Exemplary embodiments of the invention provide recombinant host cells containing the vectors described herein. Host cells include, for example, prokaryotic cells, lower eukaryotic cells such as yeast, other eukaryotic cells such as insect cells, and higher eukaryotic cells such as mammalian cells.

Recombinant host cells can be prepared by introducing vector constructs, such as described herein, into cells by techniques readily available to a person of ordinary skill in the art. These techniques include, but are not limited to, calcium phosphate transfection, DEAE-dextran-mediated transfection, cationic lipid-mediated transfection, electroporation, transduction, infection, lipofection, microinjection, and other techniques such as those found in Sambrook, et al. (Molecular Cloning: A Laboratory Manual. 3rd. ed., Cold Spring Harbor Laboratory Press, Cold Spring Harbor, N.Y. (2001).

For example, using techniques such as these, a retroviral or other viral vector can be introduced into mammalian cells. Examples of mammalian cells into which a retroviral vector can be introduced include, but are not limited to, primary mammalian cultures or continuous mammalian cultures, COS cells, NIH3T3, 293 cells (ATCC #CRL 1573), and dendritic cells.

Host cells can contain more than one vector. Thus, different nucleotide sequences can be introduced on different vectors of the same cell. Similarly, nucleic acid molecules of interest can be introduced either alone or with other unrelated nucleic acid molecules such as those providing trans-acting factors for expression vectors. When more than one vector is introduced into a cell, the vectors can be introduced independently, co-introduced, or joined to the nucleic acid molecule vector.

Bacteriophage and viral vectors can be introduced into cells as packaged or encapsulated virus by standard procedures for infection and transduction. Viral vectors can be replication-competent or replication-defective. If viral replication is defective, replication can occur in host cells that provide functions that complement the defects.

Vectors can include selectable markers that enable the selection of a subpopulation of cells that contain the recombinant vector constructs. Markers can be contained in the same vector that contains the nucleic acid molecules of interest or can be on a separate vector. Exemplary markers include tetracycline or ampicillin-resistance genes for prokaryotic host cells, and dihydrofolate reductase or neomycin resistance for eukaryotic host cells. However, any marker that provides selection for a phenotypic trait can be used.

While mature proteins can be produced in bacteria, yeast, mammalian cells, and other cells under the control of appropriate regulatory sequences, cell-free transcription and translation systems can also be used to produce these proteins using RNA derived from the DNA constructs described herein.

If secretion of a protein is desired, appropriate secretion signals can be incorporated into a vector. The signal sequence can be endogenous or heterologous to the protein.

If a protein is not secreted into a medium, the protein can be isolated from a host cell by standard disruption procedures, including freeze/thaw, sonication, mechanical disruption, use of lysing agents, and the like. A protein can then be recovered and purified by well-known purification methods including, for example, ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that, depending upon the host cell used in recombinant production of a protein, proteins can have various glycosylation patterns or can be non-glycosylated, such as when produced in bacteria. In addition, proteins can include an initial modified methionine in some instances as a result of a host-mediated process.

Recombinant host cells that express a CAT protein have a variety of uses. For example, such host cells are useful for producing CAT proteins, which can be further purified to produce desired amounts of the protein or fragments thereof. Thus, host cells containing expression vectors are useful for protein production.

Host cells are also useful for conducting cell-based assays involving a CAT protein or fragments thereof. For example, a recombinant host cell expressing a CAT protein can be used to assay compounds that stimulate or inhibit the protein's function.

Host cells are also useful for identifying mutant CAT proteins in which the protein's function is affected. Host cells expressing mutant proteins are useful for assaying compounds that have a desired effect on the mutant proteins (e.g., stimulating or inhibiting function), particularly if the mutant proteins naturally occur and give rise to a pathology.

6. Diagnosis and Treatment in General

The following terms, as used in the present specification and claims, are intended to have the meaning as defined below, unless indicated otherwise.

As used herein, a "biological sample" (or just "sample") can comprise, for example, tissue, blood, sera, cells, cell lines, or biological fluids such as plasma, interstitial fluid, urine, cerebrospinal fluid, and the like. A biological sample is typically, although not necessarily, obtained from an individual by a medical practitioner.

As used herein, a "subject" can be a mammalian subject or non-mammalian subject, preferably a mammalian subject. A mammalian subject can be a human or non-human, preferably a human. The terms "subject", "individual", and "patient" are used herein interchangeably.

A "healthy" or "normal" subject or biological sample is a subject or biological sample in which the disease of interest is not detectable, as ascertained by using conventional diagnostic methods (such a biological sample can interchangeably be referred to as a "control" sample).

As used herein, "disease(s)" include cancer, particularly the cancers identified in Table 1 (as indicated for each peptide) and/or Table 3, and associated diseases and pathologies.

The terms "diagnose" (or "diagnosing", etc.) and "assess" (or "assessing", etc.) are used herein interchangeably. Diagnosing or assessing diseases can include, for example, initially detecting the presence of a disease; determining a specific stage, sub-type, or other classification or characteristic of a disease; prognosing the future course of a disease; monitoring disease progression (e.g., monitoring metastatic spread of a cancer) or remission; determining or predicting response to a treatment; determining or predicting recurrence of a disease; and/or determining the likelihood of developing a disease in the future.

"Treat", "treating", or "treatment" of a disease includes: (1) inhibiting the disease, i.e., arresting or reducing the development of the disease or its clinical symptoms, or (2) relieving the disease, i.e., causing regression of the disease or its clinical symptom(s).

The term "prophylaxis" is used to distinguish from "treatment," and to encompass both "preventing" and "suppressing." It is not always possible to distinguish between "preventing" and "suppressing," as the ultimate inductive event or events may be unknown, latent, or the patient is not ascertained until well after the occurrence of the event or events. Therefore, the term "protection", as used herein, is meant to include "prophylaxis."

A "therapeutically effective amount" means the amount of an agent that, when administered to a subject for treating a disease, is sufficient to effect such treatment for the disease. The "therapeutically effective amount" can vary depending on such factors as the agent, the disease and its severity, and the age, weight, etc., of the subject to be treated.

A "differential level" is a level of a target (e.g., CAT protein or nucleic acid) in a test sample (e.g., disease sample, or drug resistant cells) either above or below the level of the same target in a corresponding control or normal sample (e.g., a control cell line or a biological sample from a healthy individual, or cells responsive/sensitive to a drug).

Exemplary embodiments of the invention provide methods for treating diseases, especially cancer, particularly the cancers identified in Table 1 (as indicated for each peptide) and/or Table 3, comprising administering to a patient a therapeutically effective amount of an antagonist, agonist, or a pharmaceutical composition thereof. Exemplary embodiments of the invention further provide agonists and antagonists to CAT proteins, as well as pharmaceutical compositions that comprise an agonist or antagonist with a suitable carrier such as a pharmaceutically acceptable excipient.

Exemplary agonists or antagonists include antibodies that specifically bind to a CAT protein. Antibodies can be used alone or in combination with one or more other therapeutic agents (e.g., as an antibody-drug conjugate or a combination therapy). Further examples of molecules that can be used as antagonists include, but are not limited to, small molecules that inhibit the function or abundance level of CAT, and inhibitory nucleic acid molecules such as RNAi or antisense nucleic acid molecules that specifically hybridize to CAT nucleic acid.

Exemplary embodiments of the invention further encompass novel agents identified by screening assays using CAT, such as the screening assays described herein, as well as methods of using these agents, such as for treatment or diagnostic purposes. For example, an agent identified as described herein (e.g., a CAT-modulating agent, a CAT-specific nucleic acid molecule such as an RNAi or antisense molecule, a CAT-specific antibody, a CAT-specific antibody-drug conjugate, or a CAT-binding partner) can be used in an animal or other model, such as to determine efficacy, toxicity, or side effects of treatment with the agent.

Modulators of CAT protein activity, such as modulators identified according to the drug screening assays described herein, can be used to treat a subject with a disorder mediated by a CAT, e.g., by treating cells or tissues that express CAT at a differential level. Methods of treatment can include the step of administering a modulator of CAT activity in a pharmaceutical composition to a subject in need of such treatment.

In certain exemplary embodiments, if decreased expression or activity of a protein is desired, an antibody to the protein or an inhibitor/antagonist and the like, or a pharmaceutical agent containing one or more of these molecules, can be administered to an individual. In other exemplary embodiments, if increased expression or activity of a protein is desired, the protein itself or an agonist/enhancer and the like, or a pharmaceutical agent containing one or more of these molecules, can be administered. Administration can be effected by methods well known in the art and may include delivery by an antibody specifically targeted to the protein. Neutralizing antibodies, which inhibit dimer formation, can be used when decreased expression or activity of a protein is desired.

Although modulating agents can be administered in a pure or substantially pure form, modulating agents can also be administed as pharmaceutical compositions, formulations, or preparations with a carrier. Exemplary formulations of the invention, such as for human or veterinary use, comprise a suitable active CAT-modulating agent, together with one or more pharmaceutically acceptable carriers and, optionally, other therapeutic ingredients. The carrier(s) are "acceptable" in the sense of being compatible with other ingredients of a formulation and not deleterious to the recipient thereof. The formulations can be presented in unit dosage form and can be prepared by any method known to the skilled artisan.

Examples of suitable pharmaceutical carriers include proteins such as albumins (e.g., U.S. Pat. No. 4,507,234), peptides and polysaccharides such as aminodextran (e.g., U.S. Pat. No. 4,699,784), and water. A carrier can also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate can be formed from chelating compounds that include those containing nitrogen and sulfur atoms as the donor atoms for binding the metal, metal oxide, radionuclide. For example, U.S. Pat. No. 4,673,562 discloses representative chelating compounds and their synthesis.

Methods of preparing pharmaceutical formulations typically include the step of bringing into association the active ingredient with the carrier, which constitutes one or more accessory ingredients. Formulations can be prepared by uniformly and intimately bringing into association the active ingredient with liquid carriers or finely divided solid carriers, or both, and then, if necessary, shaping the product into the desired formulation.

Formulations suitable for intravenous, intramuscular, subcutaneous, or intraperitoneal administration can comprise sterile aqueous solutions of the active ingredient with solutions, which can be isotonic with the blood of the recipient. Such formulations can be prepared by dissolving solid active ingredient in water containing physiologically compatible substances such as sodium chloride (e.g., 0.1-2.0 M), glycine, and the like, and having a buffered pH compatible with physiological conditions to produce an aqueous solution, and rendering the solution sterile. These may be present in unit or multi-dose containers, for example, sealed ampoules or vials.

Exemplary formulations of the invention can incorporate a stabilizer. Exemplary stabilizers include polyethylene glycol, proteins, saccharides, amino acids, inorganic acids, detergents, and organic acids, which can be used either alone or as admixtures. These stabilizers can be incorporated in an amount of, for example, 0.11-10,000 parts by weight per part by weight of an agent. If two or more stabilizers are to be used, their total amount can be within the range specified above. These stabilizers can be used in aqueous solutions at an appropriate concentration and pH. The specific osmotic pressure of such aqueous solutions can be in the range of 0.1-3.0 osmoles, preferably in the range of 0.8-1.2. The pH of the aqueous solution can be adjusted to be within the range of 5.0-9.0, preferably within the range of 6-8. In formulating an antibody or antibody-drug conjugate, an anti-adsorption agent can be used.

Additional pharmaceutical methods can be employed to control duration of action. Controlled release can be achieved through the use of polymer to complex or absorb the proteins or their derivatives. Controlled delivery can be achieved by selecting appropriate macromolecules (e.g., polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate an anti-CAT antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions can be combined with typical carriers, such as lactose, sucrose, starch, talc magnesium stearate, crystalline cellulose, methyl cellulose, carboxymethyl cellulose, glycerin, sodium alginate or gum arabic, among others.

Any of the therapeutic agents provided herein may be administered in combination with other therapeutic agents. Selection of agents for use in combination therapy can be made by one of ordinary skill in the art according to conventional pharmaceutical principles. A combination of therapeutic agents may act synergistically to affect treatment of a particular disorder at a lower dosage of each agent.

7. Methods of Detection and Diagnosis Based on CAT Proteins

CAT proteins are useful for diagnosing a disease, or predisposition to a disease, particularly diseases in which the protein is over- or under-expressed, especially cancer, particularly the cancers identified in Table 1 (as indicated for each peptide) and/or Table 3. The diagnostic methods may be further suitable for monitoring disease progression in patients undergoing treatment, or for testing for reoccurrence of disease in patients who were previously treated for a disease, for example. Accordingly, exemplary embodiments of the invention provide methods for detecting the presence of, or abundance levels of, a CAT protein in a biological sample.

In vitro techniques for detection of proteins include, but are not limited to, enzyme linked immunosorbent assays (ELISAs), Western blots, immunoprecipitations, and immunofluorescence using a detection reagent, such as an antibody or protein binding agent. Alternatively, a protein can be detected in vivo in a subject by introducing into the subject a labeled antibody (or other types of detection agent) specific for the protein target. For example, an antibody can be labeled with a radioactive marker whose presence and location in a subject can be detected by standard imaging techniques. Particularly useful are methods that detect variants of a protein (e.g., allelic variants or mutations) and methods that detect fragments of a protein in a sample.

Proteins can be isolated from a biological sample (such as from a patient having a disease) and assayed for the presence of a mutation. A mutation can include, for example, one or more amino acid substitutions, deletions, insertions, rearrangements (such as from aberrant splicing events), or inappropriate post-translational modifications. Examples of analytic methods useful for detecting mutations in a protein include, but are not limited to, altered electrophoretic mobility, altered tryptic peptide digest, altered protein activity in cell-based or cell-free assays, alteration in substrate or antibody-binding patterns, altered isoelectric point, and direct amino acid sequencing.

Information obtained by detecting a protein can be used, for example, to determine prognosis and appropriate course of treatment for a disease. For example, individuals with a particular CAT expression level or stage of disease may respond differently to a given treatment that individuals lacking CAT expression, or individuals over- or under-expressing CAT. Information obtained from diagnostic methods of the invention can provide for the personalization of diagnosis and treatment.

In exemplary embodiments, the invention provides methods for diagnosing disease (including, for example, monitoring treatment response or recurrence of disease following treatment) in a subject comprising: determining the abundance level of CAT (e.g., CAT protein or nucleic acid, or protein or nucleic acid fragments thereof) in a test sample from the subject; wherein a difference in the abundance level of CAT relative to the abundance level of CAT in a test sample from a healthy subject, or the level established for a healthy subject, is indicative of disease.

Exemplary embodiments of the invention provide methods for diagnosing diseases having differential protein expression. For example, normal, control, or standard values (e.g., that represent typical expression levels of a protein in healthy subjects) can be established, such as by combining body fluids, tissues, or cell extracts taken from a normal healthy mammalian or human subject with specific antibodies to a protein under conditions for complex formation. Standard values for complex formation in normal and disease tissues can be established by various methods, such as photometric means. Complex formation, as it is expressed in a test sample, can be compared with the standard values. Deviation from a normal standard and toward a disease standard can provide parameters for disease diagnosis or prognosis while deviation away from a disease standard and toward a normal standard can be used to evaluate treatment efficacy, for example.

Immunological methods for detecting and measuring complex formation as a measure of protein expression using either specific polyclonal or monoclonal antibodies are known in the art. Examples of such techniques include ELISAs, radioimmunoassays (RIAs), flow cytometry (also referred to as fluorescence-activated cell sorting, or FACS), and antibody arrays. Such immunoassays typically involve the measurement of complex formation between a protein and its specific antibody. These assays and their quantitation against purified, labeled standards are well known in the art (Ausubel, supra, unit 10.1-10.6). For example, a two-site, monoclonal-based immunoassay utilizing antibodies reactive to two non-interfering epitopes can be utilized, and competitive binding assay can also be utilized (Pound (1998) Immunochemical Protocols, Humana Press, Totowa N.J.).

For diagnostic applications, an antibody can be labeled with a detectable moiety (interchangeably referred to as a "label" or "detectable substance"), such as to facilitate detection by various imaging methods. Methods for detection of labels include, but are not limited to, fluorescence, light, confocal, and electron microscopy; magnetic resonance imaging and spectroscopy; fluoroscopy, computed tomography and positron emission tomography. Examples of suitable labels include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, labels may be bi- or multi-functional and be detectable by more than one of the methods listed. Antibodies may be directly or indirectly labeled. Attachment of labels to antibodies includes covalent attachment of a label, incorporation of a label into an antibody, and covalent attachment of a chelating compound for binding of a label, among others well known in the art.

Numerous detectable moieties are available for labeling antibodies, including, but not limited to, those in the following categories:

(a) Radioisotopes, such as $^{36}$S, $^{14}$C, $^{125}$I, $^{3}$H, and $^{131}$I. An antibody can be labeled with a radioisotope using the techniques described in Current Protocols in Immunology, vol 1-2, Coligen et al., Ed., Wiley-Interscience, New York, Pubs. (1991-2006), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. Fluorescent labels can be conjugated to an antibody using the techniques disclosed in Current Protocols in Immunology, supra, for example. Fluorescence can be quantified using a fluorometer.

(c) Various enzyme-substrate labels are available (e.g., U.S. Pat. Nos. 4,275,149 and 4,318,980). An enzyme generally catalyzes a chemical alteration of a chromogenic substrate which can be measured using various techniques. For example, an enzyme may catalyze a color change in a substrate, which can be measured spectrophotometrically. Alternatively, an enzyme may alter the fluorescence or chemiluminescence of a substrate. Techniques for quantifying a change in fluorescence are described herein and well known in the art A chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzyme. (Ed. J. Langone & H. Van Vunakis), Academic press, New York, 73: 147-166 (1981).

A label can be indirectly conjugated with an antibody. The skilled artisan will be aware of various techniques for achieving this. For example, an antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of a label with an antibody, an antibody can be conjugated with a small hapten (e.g., digoxin) and one of the different types of labels mentioned above can be conjugated with an anti-hapten antibody (e.g., anti-digoxin antibody). Thus, indirect conjugation of a label with an antibody can be achieved.

Antibodies can be used to isolate CAT proteins by standard techniques, such as affinity chromatography or immunoprecipitation, and antibodies can facilitate the purification of the natural protein from cells and recombinantly-produced protein expressed in host cells. Biological samples can be tested directly for the presence of a CAT protein by assays (e.g., ELISA or radioimmunoassay) and format (e.g., microwells, dipstick, etc., as described in International Patent Publication WO 93/03367). Alternatively, proteins in a sample can be size separated (e.g., by polyacrylamide gel electrophoresis (PAGE)), in the presence or absence of sodium dodecyl sulfate (SDS), and the presence of a CAT detected by immunoblotting (e.g., Western blotting).

Antibody binding can also be detected by "sandwich" immunoassays, immunoradiometric assays, gel diffusion precipitation reactions, immunodiffusion assays, in situ immunoassays (e.g., using colloidal gold, enzyme or radioisotope labels, for example), precipitation reactions, agglutination assays (e.g., gel agglutination assays, hemagglutination assays, etc.), complement fixation assays, immunofluorescence assays, protein A assays, and immunoelectrophoresis assays, etc.

In certain exemplary embodiments, antibody binding can be detected by detecting a label on the primary antibody. In other exemplary embodiments, a primary antibody can be detected by detecting binding of a secondary antibody or reagent to the primary antibody. In further exemplary embodiments, the secondary antibody is labeled. Numerous means are known in the art for detecting binding in an immunoassay and are within the scope of the invention. In some embodiments, an automated detection assay is utilized. Methods for the automation of immunoassays are well known in the art (e.g., U.S. Pat. Nos. 5,885,530; 4,981,785; 6,159,750; and 5,358,691, each of which is herein incorporated by reference). In some embodiments, the analysis and presentation of results are also automated. For example, in some embodiments, software that generates a prognosis based on the presence or absence of one or more antigens can be implemented.

Competitive binding assays typically rely on the ability of a labeled standard to compete with a test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies can be separated from the standard and test sample that remain unbound.

Sandwich assays typically involve the use of two antibodies, each capable of binding to a different immunogenic portion, or epitope, of the protein to be detected. In typical sandwich assays, the test sample to be analyzed is bound by a first antibody, which is immobilized on a solid support, and thereafter a second antibody binds to the test sample, thus forming an insoluble three-part complex (e.g., U.S. Pat. No. 4,376,110). The second antibody can itself be labeled with a detectable moiety (direct sandwich assays) or can be measured using an anti-immunoglobulin antibody that is labeled with a detectable moiety (indirect sandwich assay). For example, one type of sandwich assay is an ELISA assay, in which case the detectable moiety is an enzyme.

Antibodies can also be used for in vivo diagnostic assays. Generally, an antibody can be labeled with a radionuclide (such as $^{111}$In, $^{99}$Tc, $^{14}$C, $^{131}$I, $^{3}$H, $^{32}$P or $^{35}$S) so that disease cells or tissues can be localized using immunoscintiography, for example. In certain embodiment, antibodies or fragments thereof bind to the extracellular domains of two or more CAT proteins and the affinity value (Kd) is less than $1 \times 10^{8}$ M.

For immunohistochemistry, a disease tissue sample may be, for example, fresh or frozen or may be embedded in paraffin and fixed with a preservative such as formalin. A fixed or embedded section can be contacted with a labeled primary antibody and secondary antibody, wherein the antibody is used to detect CAT protein expression in situ.

Antibodies can be used to detect a target protein in situ, in vitro, or in a cell lysate or supernatant in order to evaluate the abundance and pattern of expression. Also, antibodies can be used to assess abnormal tissue distribution or abnormal expression during development or progression of a biological condition. Antibodies against CAT proteins are useful for detecting the presence of the proteins in cells or tissues to determine the pattern of expression of the proteins among various tissues in an organism and over the course of the organism's development.

Further, antibodies can be used to assess expression in disease states such as in active stages of a disease or in an individual with a predisposition toward disease related to the protein's function. When a disorder is caused by inappropriate tissue distribution, developmental expression, or level of expression of a protein, or expressed/processed form, for example, an antibody can be prepared against the normal protein. If a disorder is characterized by a specific mutation in a protein, antibodies specific for the mutant protein can be used to assay for the presence of the specific mutant protein and to target the mutant protein for therapeutic purposes. Antibodies are also useful as diagnostic tools, as immunological markers for aberrant protein analyzed by electrophoretic mobility, isoelectric point, tryptic peptide digest, and other physical assays known in the art.

Certain exemplary diagnostic methods of the invention can also include monitoring a treatment modality. Accordingly, where treatment is ultimately aimed at correcting, for example, the function, activity, expression level, tissue distribution, or developmental expression of a protein, antibodies directed against the protein can be used to monitor therapeutic efficacy and to modify a treatment regimen as necessary.

Additionally, antibodies to a target protein are useful in pharmacogenomic analysis. For example, antibodies prepared against polymorphic proteins can be used to identify individuals that require modified treatment modalities. Moreover, the target proteins and antibodies thereto can be used for clinical trials, such as to identify individuals that should be included (e.g., individuals more likely to respond to a therapy) or excluded (e.g., individuals less likely to respond to a therapy, or individuals more likely to experience harmful side effects from a therapy) from a clinical trial.

The invention also encompasses kits for using antibodies to detect the presence of a target protein in a biological sample. An exemplary kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be configured to detect a single target protein or epitope or can be configured to detect one of a multitude of epitopes, such as in an antibody detection array.

LC/MS and ICAT

In certain exemplary embodiments, the invention provides detection or diagnostic methods of a CAT by using LC/MS. Proteins can be prepared from cells by methods known in the art (e.g., Zhang et al., *Nature Biotechnology* 21(6):660-666 (2003)). The differential expression of proteins in disease and healthy (or drug-resistant and drug-sensitive, for example) samples can be quantitated using mass spectrometry and ICAT (Isotope Coded Affinity Tag) labeling, which is known in the art. ICAT is an isotope label technique that allows for discrimination between two populations of proteins, such as a healthy and a disease sample. Over-expression or under-expression of a CAT protein, as measured by ICAT, can indicate, for example, the likelihood of having or developing a disease or an associated pathology.

LC/MS spectra can be collected for labeled samples and processed as follows. The raw scans from the LC/MS instrument can be subjected to peak detection and noise reduction software. Filtered peak lists can then be used to detect 'features' corresponding to specific peptides from the original sample(s). Features are characterized by their mass/charge ratio, charge, retention time, isotope pattern, and/or intensity, for example.

The intensity of a peptide present in both healthy and disease samples can be used to calculate the differential expression, or relative abundance, of the peptide. The intensity of a peptide found exclusively in one sample can be used to calculate a theoretical expression ratio for that peptide (singleton). Expression ratios can be calculated for each peptide in an assay or experiment.

Statistical tests can be performed to assess the robustness of the data and select statistically significant differentials. To ensure the accuracy of data, the following steps can be taken: a) ensure that similar features are detected in all replicates of an experiment; b) assess the distribution of the log ratios of all peptides (a Gaussian is expected); c) calculate the overall pair wise correlations between ICAT LC/MS maps to ensure that the expression ratios for peptides are reproducible across multiple replicates; and d) aggregate multiple experiments in order to compare the expression ratio of a peptide in multiple diseases or disease samples.

8. Methods of Treatment Based on CAT Proteins a. Antibody Therapy

Antibodies of the invention can be used for therapeutic purposes. It is contemplated that antibodies of the invention may be used to treat a mammal, preferably a human, with a disease, especially cancer, particularly the cancers identified in Table 1 (as indicated for each peptide) and/or Table 3. The antibodies can be delivered alone, in a pharmaceutical composition (such as with a carrier), or conjugated to one or more therapeutic agents, for example.

Antibodies can be useful for modulating (e.g., agonizing or antagonizing) protein function, such as for therapeutic purposes. Antibodies can also be useful for inhibiting protein function by, for example, blocking the binding of a CAT protein to a binding partner such as a substrate, which can be useful therapeutically. Antibodies can be prepared against, for example, specific portions of a protein that contain domains required for protein function, or against intact protein that is associated with a cell membrane.

Antibodies of the invention can also be used for enhancing the immune response. The antibodies can be administered in amounts similar to those used for other therapeutic administrations of antibodies. For example, pooled gamma globulin can be administered at a range of about 1 mg to about 100 mg per patient.

Antibodies reactive with CAT proteins can be administered alone or in conjunction with other therapies, such as anti-cancer therapies, to a mammal afflicted with cancer or other disease. Examples of anti-cancer therapies include, but are not limited to, chemotherapy, radiation therapy, and adoptive immunotherapy therapy with TIL (tumor infiltrating lymphocytes).

The selection of an antibody subclass for therapy may depend upon the nature of the antigen to be acted upon. For example, an IgM may be preferred in situations where the antigen is highly specific for the diseased target and rarely occurs on normal cells. However, where the disease-associated antigen is also expressed in normal tissues, although at lower levels, the IgG subclass may be preferred. The IgG subclass may be preferred in these instances because the binding of at least two IgG molecules in close proximity is typically required to activate complement, and therefore less complement-mediated damage may occur in normal tissues that express smaller amounts of the antigen and thus bind fewer IgG antibody molecules. Furthermore, IgG molecules, by being smaller, may be more able than IgM molecules to localize to a diseased tissue.

A mechanism for antibody therapy can be that a therapeutic antibody recognizes a cell surface, secreted, or cytosolic target protein that is expressed (preferably, over-expressed) in a disease cell. By NK cell or complement activation, or conjugation of the antibody with an immunotoxin or radiolabel, the interaction of the antibody with the target protein can abrogate ligand/receptor interaction or activation of apoptosis, for example.

Potential mechanisms of antibody-mediated cytotoxicity of diseased cells include phagocyte (antibody-dependent cellular cytotoxicity (ADCC)), complement (complement-dependent cytotoxicity (CDC)), naked antibody (receptor cross-linking apoptosis and growth factor inhibition), or targeted payload labeled with a therapeutic agent, such as a radionuclide, immunotoxin, or immunochemotherapeutic or other therapeutic agent.

In certain exemplary embodiments, an antibody is administered to a nonhuman mammal for the purposes of obtaining preclinical data, for example. Exemplary nonhuman mammals to be treated include nonhuman primates, dogs, cats, rodents, and other mammals in which preclinical studies are performed. Such mammals may be established animal models for a disease or may be used to study toxicity of an antibody of interest, for example. Dose escalation studies may be performed in the mammal, for example.

An antibody can be administered to an individual by any suitable means, including parenteral, subcutaneous, intraperitoneal, intrapulmonary, and intranasal, and, if desired for local immunomodulatory treatment, intralesional administration. Parenteral infusions include intramuscular, intravenous, intraarterial, intraperitoneal, or subcutaneous administration. In addition, an antibody can be administered by pulse infusion, particularly with declining doses of the antibody. The dosing can be given by injections, such as intravenous or subcutaneous injections, which may depend in part on whether the administration is brief or chronic.

For the prevention or treatment of a disease, the appropriate dosage of an antibody may depend on the type of disease to be treated, the severity and the course of the disease, whether the antibody is administered for preventive or therapeutic purposes, previous therapy, the patient's clinical history and response to the antibody, and the discretion of the attending physician.

Depending on the type and severity of disease, about 1 µg/kg to 150 mg/kg (e.g., 0.1-20 mg/kg) of antibody can be an initial candidate dosage for administration to a patient, whether, for example, by one or more separate administrations, or by continuous infusion. A typical daily dosage may range from about 1 µg/kg to 100 mg/kg or more, depending on such factors as those mentioned above. An antibody-drug conjugate can be administered from about 1 µg/kg to 50 mg/kg, typically from about 0.1-20 mg/kg, whether, for example, by one or more separate administrations, or by continuous infusion. A typical daily dosage may range from about 0.1 mg/kg to 10 mg/kg, or from about 0.3 mg/kg to about 7.5 mg/kg, depending on such factors as those mentioned above. For repeated administrations over several days or longer, depending on the condition, the treatment can be sustained until a desired suppression of disease symptoms occurs. However, other dosage regimens may be useful. Therapy progress can be monitored by conventional techniques and assays.

Antibody composition can be formulated, dosed, and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

An antibody may optionally be formulated with, or administered with, one or more therapeutic agents used to prevent or treat the disorder in question. For example, an antibody can be administered as a co-therapy with a standard of care therapeutic for the specific disease being treated.

b. Other Immunotherapy

An "immunogenic peptide" is a peptide that comprises an allele-specific motif such that the peptide typically will bind an MHC allele (HLA in human) and be capable of inducing a CTL (cytotoxic T-lymphocytes) response. Thus, immunogenic peptides typically are capable of binding to an appropriate class I or II MHC molecule and inducing a cytotoxic T cell or T helper cell response against the antigen from which the immunogenic peptide is derived.

Peptides derived from a CAT protein can be modified to increase their immunogenicity, such as by enhancing the binding of the peptide to the MHC molecules in which the peptide is presented. The peptide or modified peptide can be conjugated to a carrier molecule to enhance the antigenicity of the peptide. Examples of carrier molecules, include, but are not limited to, human albumin, bovine albumin, lipoprotein and keyhole limpet hemo-cyanin ("Basic and Clinical Immunology" (1991) Stites and Terr (eds) Appleton and Lange, Norwalk Conn., San Mateo, Calif.).

Further, amino acid sequence variants of a peptide can be prepared, such as by altering the nucleic acid sequence of the DNA which encodes the peptide, or by peptide synthesis. At the genetic level, these variants can be prepared by, for example, site-directed mutagenesis of nucleotides in the DNA encoding the peptide, thereby producing DNA encoding the variant, and thereafter expressing the DNA in recombinant cell culture. The variants can exhibit the same qualitative biological activity as the nonvariant peptide.

Exemplary embodiments of the invention provide peptides or modified peptides derived from a CAT protein that are differentially expressed in disease. Examples of peptide modifications include, but are not limited to, substitutions, deletions, or additions of one or more amino acids in a given immunogenic peptide sequence, or mutation of existing amino acids within a given immunogenic peptide sequence, or derivatization of existing amino acids within a given immunogenic peptide sequence. Any amino acid in an immunogenic peptide sequence may be modified. In some embodiments, at least one amino acid can be substituted or replaced within the given immunogenic peptide sequence. Any amino acid may be used to substitute or replace a given amino acid within the immunogenic peptide sequence. Modified peptides can include any immunogenic peptide obtained from differentially expressed proteins, which has been modified and exhibits enhanced binding to the MHC molecule with which it associates when presented to a T-cell. These modified peptides can be synthetically or recombinantly produced by conventional methods, for example.

In certain exemplary embodiments of the invention, the peptides comprise, or consist of, sequences of about 5-30 amino acids in length which are immunogenic (i.e., capable of inducing an immune response when injected into a subject).

In certain exemplary embodiments, the peptides may be used, for example, to treat T cell-mediated pathologies. The term "T cell-mediated pathologies" refers to any condition in which an inappropriate T cell response is a component of the pathology. The term is intended to encompass both T cell mediated diseases and diseases resulting from unregulated clonal T cell replication.

Modified (e.g., recombinant) or natural CAT proteins, or fragments thereof, can be used as a vaccine either prophylactically or therapeutically. When provided prophylactically, a vaccine can be provided in advance of any evidence of disease. The prophylactic administration of a disease vaccine may serve to prevent or attenuate a disease in a mammal such as a human.

An exemplary vaccine formulation can comprise an immunogen that induces an immune response directed against a disease-associated antigen such as a CAT protein. For example, a substantially or partially purified CAT protein or fragments thereof can be administered as a vaccine in a pharmaceutically acceptable carrier. An immunogen can be administered in a pure or substantially pure form, or can be administered as a pharmaceutical composition, formulation, or preparation. Exemplary doses of protein that can be administered are about 0.001 to about 100 mg per patient, or about 0.01 to about 100 mg per patient. Immunization can be repeated as necessary until a sufficient titer of anti-immunogen antibody or immune cells has been obtained.

Vaccine can be prepared using, for example, recombinant protein or expression vectors comprising a nucleic acid sequence encoding all or part of a CAT protein. Examples of vectors that can be used in vaccines include, but are not limited to, defective retroviral vectors, adenoviral vectors vaccinia viral vectors, fowl pox viral vectors, or other viral vectors (Mulligan, R. C., (1993) *Science* 260:926-932). The vectors can be introduced into a mammal (e.g., a human) either prior to any evidence of a disease or to mediate regression of a disease in a mammal afflicted with the disease. Examples of methods for administering a viral vector into mammals include, but are not limited to, exposure of cells to the virus ex vivo, or injection of the retrovirus or a producer cell line of the virus into the affected tissue, or intravenous administration of the virus. Alternatively, the vector can be administered locally by direct injection into a disease lesion or topical application in a pharmaceutically acceptable carrier. The quantity of viral vector to be administered can be based on the titer of virus particles. An exemplary range can be about $10^6$ to about $10^{11}$ virus particles per mammal.

After immunization, the efficacy of the vaccine can be assessed by, for example, the production of antibodies or immune cells that recognize the antigen, as assessed by specific lytic activity, specific cytokine production, or disease regression, which can be measured using conventional methods. If the mammal to be immunized is already afflicted with a disease, the vaccine can be administered in conjunction with other therapeutic treatments. Examples of other therapeutic treatments include, but are not limited to, adoptive T cell immunotherapy and coadministration of cytokines or other therapeutic drugs.

In certain embodiments, mammals, preferably humans, at high risk for disease, especially cancer, are prophylactically treated with vaccines of the invention. Examples include, but are not limited to, individuals with a family history of a disease, individuals who themselves have a history of disease (e.g., cancer that has been previously resected and at risk for reoccurrence), or individuals already afflicted with a disease. When provided therapeutically, a vaccine can be provided to enhance the patient's own immune response to a disease antigen. An exemplary vaccine, which acts as an immunogen, can be a cell, cell lysate from cells transfected with a recombinant expression vector, or a culture supernatant containing the expressed protein, for example. Alternatively, an immunogen can be, for example, a partially or substantially purified recombinant protein, peptide, or analog thereof, or a modified protein, peptide, or analog thereof. The proteins or peptides can be, for example, conjugated with lipoprotein or administered in liposomal form or with adjuvant.

Vaccination can be carried out using conventional methods. For example, an immunogen can be used in a suitable diluent such as saline or water, or complete or incomplete adjuvants. Further, an immunogen may or may not be bound to a carrier, including carriers to increase the immunogenicity of the immunogen. Examples of carrier molecules include, but are not limited to, bovine serum albumin (BSA), keyhole limpet hemocyanin (KLH), tetanus toxoid, and the like. An immunogen also may be coupled with lipoproteins or administered in liposomal form or with adjuvants. An immunogen can be administered by any route appropriate for antibody production such as intravenous, intraperitoneal, intramuscular, subcutaneous, and the like. An immunogen can be administered once or at periodic intervals until a significant titer of anti-CAT immune cells or anti-CAT antibody is produced. The presence of anti-CAT immune cells can be assessed by measuring the frequency of precursor CTL (cytotoxic T-lymphocytes) against CAT antigen prior to and after immunization by a CTL precursor analysis assay (Coulie et al., 1992, *International Journal Of Cancer* 50:289-297). An immunoassay can be used to detect antibody in serum.

The safety of a vaccine can be determined by examining the effect of immunization on the general health of an immunized animal (e.g., weight change, fever, change in appetite or behavior, etc.) and looking for pathological changes during autopsies. After initial testing in animals, a vaccine can be tested in patients having a disease of interest. Conventional methods can be used to evaluate the immune response of a patient to determine the efficiency of the vaccine.

In certain exemplary embodiments of the invention, a CAT protein or fragments thereof, or a modified CAT protein, can be exposed to dendritic cells cultured in vitro. The cultured dendritic cells provide a means of producing T-cell dependent antigens comprised of dendritic cell-modified antigen or dendritic cells pulsed with antigen, in which the antigen is processed and expressed on the antigen-activated dendritic cell. The antigen-activated dendritic cells or processed dendritic cell antigens can be used as immunogens for vaccines or for the treatment of diseases. The dendritic cells can be exposed to the antigen for sufficient time to allow the antigens to be internalized and presented on the surface of dendritic cells. The resulting dendritic cells or the dendritic cell-processed antigens can then be administered to an individual in need of therapy. Such methods are described in Steinman et al. (WO93/208185) and in Banchereau et al. (EPO Application 0563485A1).

In certain exemplary embodiments of the invention, T-cells isolated from individuals can be exposed to a CAT protein or fragment thereof, or a modified CAT protein, in vitro and then administered in a therapeutically effective amount to a patient in need of such treatment. Examples of where T-lymphocytes can be isolated include, but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami et al., 1989, *J. Immunol.* 142: 2453-3461). Lymphocytes can be cultured in media such as RPMI or RPMI 1640 or AIM V for 1-10 weeks. Viability can be assessed by trypan blue dye exclusion assay. Examples of how these sensitized T-cells can be administered to a mammal include, but are not limited to, intravenously, intraperitoneally, or intralesionally. Parameters that can be assessed to determine the efficacy of these sensitized T-lymphocytes include, but are not limited to, production of immune cells in the mammal being treated or tumor regression. Conventional methods can be used to assess these parameters. Such treatment can be given in conjunction with cytokines or gene-modified cells, for example (Rosenberg et al., 1992, *Human Gene Therapy*, 3: 75-90; Rosenberg et al., 1992, *Human Gene Therapy*, 3: 57-73).

9. Screening Methods Using CAT Proteins

Exemplary embodiments of the invention provide methods of screening for agents (interchangeably referred to by such terms as candidate agents, compounds, or candidate compounds) that modulate CAT protein activity (interchangeably referred to as protein function). Examples of candidate agents include, but are not limited to, proteins, peptides, antibodies, nucleic acids (such as antisense and RNAi nucleic acid molecules), and small molecules. Exemplary embodiments of the invention further provide agents identified by these screening methods, and methods of using these agents, such as for treating diseases, especially cancer, particularly the cancers identified in Table 1 (as indicated for each peptide) and/or Table 3.

Exemplary screening methods can typically comprise the steps of (i) contacting a CAT protein with a candidate agent, and (ii) assaying for CAT protein activity, wherein a change in protein activity in the presence of the agent relative to protein activity in the absence of the agent indicates that the agent modulates CAT protein activity.

Other exemplary screening methods can determine a candidate agent's ability to modulate CAT expression. Exemplary methods can typically comprise the steps of (i) contacting a candidate agent with a system that is capable of expressing CAT protein or CAT mRNA, and (ii) assaying for the level of CAT protein or CAT mRNA, wherein a change in the level in the presence of the agent relative to the level in the absence of the agent indicates that the agent modulates CAT expression levels.

Exemplary embodiments of the invention further provide methods to screen for agents that bind to CAT proteins. Exemplary methods can typically comprise the steps of contacting a CAT protein with a test agent and measuring the extent of binding of the agent to the CAT protein.

CAT proteins can be used to identify agents that modulate activity of a protein in its natural state or an altered form that causes a specific disease or pathology. CAT proteins and appropriate variants and fragments can be used in high-throughput screens to assay candidate compounds for their ability to bind to CAT. These compounds can be further screened against functional CAT proteins to determine the effect of the compound on the protein's activity. Further, these compounds can be tested in animal or invertebrate systems to determine activity/effectiveness. Compounds can be identified that activate (agonist) or inactivate (antagonist) CAT proteins to a desired degree.

CAT proteins can be used to screen agents for their ability to stimulate or inhibit interaction between a CAT protein and a target molecule that normally interacts with the CAT protein (e.g., a substrate, an extracellular binding ligand, or a component of a signal pathway that a CAT protein normally interacts with such as a cytosolic signal protein). Exemplary assays can include the steps of combining a CAT protein or fragment thereof with a candidate compound under conditions that allow the CAT protein (or fragment thereof) to interact with a target molecule, and detecting the formation of a complex between the CAT protein and the target molecule or detecting the biochemical consequence of the interaction between the CAT protein and the target molecule, such as any of the associated effects of signal transduction (e.g., protein phosphorylation, cAMP turnover, adenylate cyclase activation, etc.). Any of the biological or biochemical functions mediated by a CAT protein can be used as an endpoint assay to identify an agent that modulates CAT activity.

Candidate compounds or agents include, but are not limited to, 1) peptides such as soluble peptides, including Ig-tailed fusion peptides and members of random peptide libraries (see, e.g., Lam et al., *Nature* 354:82-84 (1991); Houghten et al., *Nature* 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767-778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

An exemplary candidate compound or agent is a soluble fragment of a CAT that competes for substrate binding. Other exemplary candidate compounds include mutant CAT proteins or appropriate fragments containing mutations that affect CAT function and thus compete for substrate. Accordingly, a fragment that competes for substrate, for example with a higher affinity, or a fragment that binds substrate but does not allow release, is encompassed by the invention.

Compounds can also be screened by using chimeric proteins in which any portion of a protein such as an amino terminal extracellular domain, a transmembrane domain (e.g., transmembrane segments or intracellular or extracellular loops), or a carboxy terminal intracellular domain can be replaced in whole or part by heterologous domains or subregions. For example, a substrate-binding region can be used that interacts with a different substrate than the substrate that is recognized by a native target protein. Accordingly, a different set of signal transduction components can be available as an end-point assay for activation, thereby allowing assays to be performed in other than the specific host cell from which a target is derived.

Competition binding assays can also be used to screen for compounds that interact with a target protein (e.g., binding partners and/or ligands). For example, a test compound can be exposed to a target protein under conditions that allow the test compound to bind or otherwise interact with the target protein. Soluble target protein can also be added to the mixture. If the test compound interacts with the soluble target protein, it can decrease the amount of complex formed or activity of the target protein. This type of assay is particularly useful in instances in which compounds are sought that interact with specific regions of a target protein. Thus, the soluble target protein that competes with the target protein can contain peptide sequences corresponding to the target region of interest.

To perform cell-free drug screening assays, it may be desirable to immobilize either a CAT protein (or fragment thereof) or a molecule that binds the CAT protein (referred to herein as a "binding partner") to facilitate separation of complexes from uncomplexed forms, as well as to facilitate automation of the assays.

Techniques for immobilizing proteins on matrices can be utilized in exemplary drug screening assays. In exemplary embodiments, a fusion protein can be provided which adds a domain that allows a protein to be bound to a matrix. For example, glutathione-S-transferase fusion proteins can be adsorbed onto glutathione SEPHAROSE beads (Sigma Chemical, St. Louis, Mo.) or glutathione derivatized microtitre plates, which are then combined with cell lysates (e.g., $^{35}$S-labeled) and a candidate compound, and the mixture incubated under conditions conducive to complex formation (e.g., at physiological conditions for salt and pH). Following incubation, the beads can be washed to remove any unbound label, and the matrix immobilized and radiolabel determined directly, or in the supernatant after the complexes are dissociated. Alternatively, the complexes can be dissociated from the matrix, separated by SDS-PAGE, and the level of a binding partner found in the bead fraction quantitated from the gel using standard electrophoretic techniques. For example, either a target protein or a binding partner can be immobilized by conjugation of biotin and streptavidin using techniques well known in the art. Alternatively, antibodies that are reactive with a target protein but do not interfere with binding of the target protein to its binding partner can be derivatized to the wells of a plate, and the target protein trapped in the wells by antibody conjugation. Preparations of a binding partner and a candidate compound can be incubated in target protein-presenting wells and the amount of complex trapped in the well can be quantitated. Methods for detecting such complexes, in addition to those described for GST-immobilized complexes, include immunodetection of complexes using antibodies reactive with a binding partner, or which are reactive with a target protein and compete with the binding partner, as well as target protein-linked assays which rely on detecting an enzymatic activity associated with a binding partner.

In exemplary embodiments of the invention, a CAT protein can be used as a "bait protein" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with a CAT protein and are involved in the protein's activity. The two-hybrid system is based on the modular nature of most transcription factors, which typically consist of separable DNA-binding and activation domains. In exemplary embodiments, the two-hybrid assay can utilize two different DNA constructs. In one construct, a gene that encodes a CAT protein can be fused to a gene encoding the DNA binding domain of a known transcription factor (e.g., GAL-4). In the other construct, a DNA sequence from a library of DNA sequences that encode an unidentified protein ("prey" or "sample") can be fused to a gene that encodes the activation domain of the known transcription factor. If the "bait" and the "prey" proteins are able to interact in vivo, forming a CAT-dependent complex, the DNA-binding and activation domains of the transcription factor are brought into close proximity. This proximity allows transcription of a reporter gene (e.g., LacZ), which can be operably linked to a transcriptional regulatory site responsive to the transcription factor. Expression of the reporter gene can be detected and cell colonies containing the functional transcription factor can be isolated and used to obtain the cloned gene that encodes the protein that interacts with the CAT protein.

Agents that modulate a CAT protein can be identified using one or more of the above assays, alone or in combination. For example, a cell-based or cell free system can be used for initial identification of agents, and then activity of the agents can be confirmed in an animal or other model system. Such model systems are well known in the art and can readily be employed in this context.

10. Diagnosis, Treatment, and Screening Methods Using CAT Nucleic Acid Molecules The nucleic acid molecules of the invention are useful, for example, as probes, primers, chemical intermediates, and in biological assays. The nucleic acid molecules are useful as hybridization probes for messenger RNA, transcript/cDNA, and genomic DNA to detect or isolate full-length cDNA and genomic clones encoding a CAT protein, or variants thereof. The nucleic acid molecules are also useful as primers for PCR to amplify any given region of a nucleic acid molecule and are useful to synthesize antisense molecules of desired length and sequence. The nucleic acid molecules are also useful for producing ribozymes corresponding to all, or a part, of the mRNA produced from the nucleic acid molecules described herein.

The nucleic acid molecules are also useful for constructing recombinant vectors. Exemplary vectors include expression vectors that express a portion of, or all of, a CAT protein. The nucleic acid molecules are also useful for expressing antigenic portions of the proteins. The nucleic acid molecules are also useful for constructing host cells expressing a part, or all, of the proteins. The nucleic acid molecules are also useful for constructing transgenic animals expressing all, or a part, of the proteins.

A primer or probe can correspond to any sequence along the entire length of a CAT-encoding nucleic acid molecule such as the nucleic acid molecules of SEQ ID NOS:723-1281, 1976, and 1978. Accordingly, a primer or probe can be derived from 5' noncoding regions, coding regions, or 3' noncoding regions, for example.

Exemplary in vitro techniques for detection of mRNA include Northern hybridizations and in situ hybridizations. Exemplary in vitro techniques for detecting DNA include Southern hybridizations and in situ hybridization. Reverse transcriptase PCR amplification (RT-PCR) and the like can also be used for detecting RNA expression. A specific exemplary method of detection comprises using TaqMan technology (Applied Biosystems, Foster City, Calif.).

a. Methods of Diagnosis Using Nucleic Acids

Nucleic acid molecules of the invention are useful, for example, as hybridization probes for determining the presence, level, form, and/or distribution of nucleic acid expression. Exemplary probes can be used to detect the presence of, or to determine levels of, a specific nucleic acid molecule in cells, tissues, and in organisms. Accordingly, probes corresponding to a CAT described herein can be used to assess expression and/or gene copy number in a given cell, tissue, or organism, which can be applied to, for example, diagnosis of disorders involving an increase or decrease in CAT protein expression relative to normal CAT protein expression levels.

Probes can be used as part of a diagnostic test kit for identifying cells or tissues that express CAT protein differentially, such as by measuring a level of a CAT-encoding nucleic acid (e.g., mRNA or genomic DNA) in a sample of cells from a subject, or determining if a CAT-encoding nucleic acid is mutated.

Exemplary embodiments of the invention encompass kits for detecting the presence of CAT-encoding nucleic acid (e.g., mRNA or genomic DNA) in a biological sample. For example, an exemplary kit can comprise reagents such as a labeled or labelable nucleic acid or agent capable of detecting CAT nucleic acid in a biological sample; means for determining the amount of CAT nucleic acid in the sample; and means for comparing the amount of CAT nucleic acid in the sample with a standard. The compound or agent can be packaged in a suitable container. The kit can further comprise instructions for using the kit to detect CAT nucleic acid.

The nucleic acid molecules are useful in diagnostic assays for qualitative changes in CAT nucleic acid expression, and particularly in qualitative changes that lead to pathology. The nucleic acid molecules can be used to detect mutations in CAT genes and gene expression products such as mRNA. The nucleic acid molecules can be used as hybridization probes to detect naturally occurring genetic mutations in a CAT gene and to determine whether a subject with the mutation is at risk for a disorder caused by the mutation. Examples of mutations include deletions, additions, or substitutions of one or more nucleotides in a gene, chromosomal rearrangements (such as inversions or transpositions), and modification of genomic DNA such as aberrant methylation patterns or changes in gene copy number (such as amplification). Detection of a mutated form of a CAT gene associated with a dysfunction can provide a diagnostic tool for an active disease or susceptibility to disease in instances in which the disease results from overexpression, underexpression, or altered expression of a CAT protein, for example.

Mutations in a CAT gene can be detected at the nucleic acid level by a variety of techniques. For example, genomic DNA, RNA, or cDNA can be analyzed directly or can be amplified (e.g., using PCR) prior to analysis. In certain exemplary embodiments, detection of a mutation involves the use of a probe/primer in a PCR reaction (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077-1080 (1988) and Nakazawa et al., *PNAS* 91:360-364 (1994)), the latter of which can be particularly useful for detecting point mutations in a gene (see Abravaya et al., *Nucleic Acids Res.* 23:675-682 (1995)). Exemplary methods such as these can include the steps of collecting a sample of cells from a patient, isolating nucleic acid (e.g., genomic, mRNA, or both) from the cells of the sample, contacting the nucleic acid with one or more primers which specifically hybridize to a target nucleic acid under conditions such that hybridization and amplification of the target nucleic acid (if present) occurs, and detecting the presence or absence of an amplification product, or detecting the size of the amplification product and comparing the length to a control sample. Deletions and insertions can be detected by a change in size of the amplified product compared to a normal genotype. Point mutations can be identified by hybridizing amplified DNA to normal RNA or antisense DNA sequences, for example.

Alternatively, mutations in a CAT gene can be identified, for example, by alterations in restriction enzyme digestion patterns as determined by gel electrophoresis. Further, sequence-specific ribozymes (U.S. Pat. No. 5,498,531) can be used to identify the presence of specific mutations by development or loss of a ribozyme cleavage site. Perfectly matched sequences can be distinguished from mismatched sequences by nuclease cleavage digestion assays or by differences in melting temperature.

Sequence changes at specific locations can be assessed by nuclease protection assays such as RNase and S1 protection, or chemical cleavage methods. Furthermore, sequence differences between a mutant CAT gene and a corresponding wild-type gene can be determined by direct DNA sequencing. A variety of automated sequencing procedures can be utilized when performing diagnostic assays (Naeve, C. W., (1995) *Biotechniques* 19:448), including sequencing by mass spectrometry (e.g., PCT International Publication No. WO 94/16101; Cohen et al., *Adv. Chromatogr.* 36:127-162 (1996); and Griffin et al., *Appl. Biochem. Biotechnol.* 38:147-159 (1993)).

Other methods for detecting mutations in a nucleic acid include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286-295 (1992)), electrophoretic mobility of mutant and wild type nucleic acid is compared (Orita et al., *PNAS* 86:2766 (1989); Cotton et al., *Mutat. Res.* 285:125-144 (1993); and Hayashi et al., *Genet. Anal. Tech. Appl.* 9:73-79 (1992)), and movement of mutant or wild-type fragments in polyacrylamide gels containing a gradient of denaturant is assayed using denaturing gradient gel electrophoresis (DGGE) (Myers et al., *Nature* 313:495 (1985)). Examples of other techniques for detecting point mutations include selective oligonucleotide hybridization, selective amplification, and selective primer extension.

b. Methods of Monitoring Treatment and Pharmacogenomic Methods Using Nucleic Acids Nucleic acid molecules of the invention are also useful for monitoring the effectiveness of modulating agents on the expression or activity of a CAT gene, such as in clinical trials or in a treatment regimen. For example, the gene expression pattern of a CAT gene can serve as a barometer for the continuing effectiveness of treatment with a compound, particularly with compounds to which a patient can develop resistance. The gene expression pattern can also serve as a marker indicative of a physiological response of the affected cells to the compound. For example, based on monitoring nucleic acid expression, the administration of a compound can be increased or alternative compounds to which the patient has not become resistant can be administered instead. Similarly, if the level of nucleic acid expression falls below a desirable level, administration of the compound can be commensurately decreased.

The nucleic acid molecules are also useful for testing an individual for a genotype that, while not necessarily causing a disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules provided herein can be used to assess the mutation content of a target gene in an individual in order to select an appropriate compound or dosage regimen for treatment. For example, target nucleic acid molecules having genetic variations that affect treatment can provide diagnostic targets that can be used to tailor treatment to an individual. Accordingly, the production of recombinant cells and animals having these genetic variations allows effective clinical design of treatment compounds and dosage regimens, for example.

c. Methods of Treatment Using Nucleic Acids

Nucleic acid molecules of the invention are useful to design antisense constructs to control CAT gene expression in cells, tissues, and organisms. An antisense nucleic acid molecule typically blocks translation of mRNA into CAT protein by hybridizing to target mRNA in a sequence-specific manner. Nucleic acid molecules of the invention can also be used to specifically suppress gene expression by methods such as RNA interference (RNAi). RNAi and antisense-based gene suppression are well known in the art (e.g., *Science* 288:1370-1372, 2000). RNAi typically operates on a post-transcriptional level and is sequence specific. RNAi and antisense nucleic acid molecules are useful for treating diseases, especially cancer. RNAi fragments, particularly double-stranded (ds) RNAi, as well as antisense nucleic acid molecules can also be used to generate loss-of-function phenotypes by suppressing gene expression. Accordingly, exemplary embodiments of the invention provide RNAi and antisense nucleic acid molecules, and methods of using these RNAi and antisense nucleic acid molecules, such as for therapy or for modulating cell function. Nucleic acid molecules may also be produced that are complementary to a region of a gene involved in transcription, such as to hybridize to the gene to prevent transcription.

Exemplary embodiments of the invention relate to isolated RNA molecules (double-stranded; single-stranded) that are about 17 to about 29 nucleotides (nt) in length, and more particularly about 21 to about 25 nt in length, which mediate RNAi (e.g., degradation of mRNA, and such mRNA may be referred to herein as mRNA to be degraded). With respect to RNAi, the terms RNA, RNA molecule(s), RNA segment(s), and RNA fragment(s) are used interchangeably to refer to RNA that mediates RNAi. These terms include double-stranded RNA, single-stranded RNA, isolated RNA (e.g., partially purified RNA, essentially pure RNA, synthetic RNA, recombinantly produced RNA), as well as altered RNA that differs from naturally occurring RNA by the addition, deletion, substitution, and/or alteration of one or more nucleotides. Such alterations can include, for example, addition of non-nucleotide material, such as to the end(s) of a 21-25 nt RNA or internally (at one or more nucleotides of the RNA). Nucleotides in exemplary RNA molecules of the invention can also comprise non-standard nucleotides, including non-naturally occurring nucleotides or deoxyribonucleotides. Collectively, all such altered RNAs are referred to as analogs or analogs of naturally-occurring RNA. RNA of 21-25 nt typically need only be sufficiently similar to natural RNA that it has the ability to mediate RNAi. As used herein, the phrase "mediates RNAi" refers to the ability to distinguish which RNAs are to be degraded by RNAi processes. RNA that mediates RNAi directs degradation of particular mRNAs by RNAi processes. Such RNA may include RNAs of various structures, including short hairpin RNA.

In certain exemplary embodiments, the invention relates to RNA molecules of about 21 to about 25 nt that direct cleavage of specific mRNA to which their sequence corresponds. It is not necessary that there be a perfect correspondence (i.e., match) of the sequences, but the correspondence must be sufficient to enable the RNA to direct RNAi cleavage of the target mRNA (Holen et al., *Nucleic Acids Res.* 33:4704-4710 (2005)). In an exemplary embodiment, the 21-25 nt RNA molecules of the invention comprise a 3' hydroxyl group.

Certain exemplary embodiments of the invention relate to 21-25 nt RNAs of specific genes, produced by chemical synthesis or recombinant DNA techniques, that mediate RNAi. As used herein, the term "isolated RNA" includes RNA obtained by any means, including processing or cleavage of dsRNA, production by chemical synthetic methods, and production by recombinant DNA techniques, for example. Exemplary embodiments of the invention further relate to uses of the 21-25 nt RNAs, such as for therapeutic or prophylactic treatment and compositions comprising 21-25 nt RNAs that mediate RNAi, such as pharmaceutical compositions comprising 21-25 nt RNAs and an appropriate carrier.

Further exemplary embodiments of the invention relate to methods of mediating RNAi of genes of a patient. For example, RNA of about 21 to about 25 nt which targets a specific mRNA to be degraded can be introduced into a patient's cells. The cells can be maintained under conditions allowing degradation of the mRNA, resulting in RNA-mediated interference of the mRNA of the gene in the cells of the patient. Treatment of cancer patients, for example, with RNAi may inhibit the growth and spread of the cancer and reduce tumor size. Treatment of patients using RNAi can also be in combination with other therapies. For example, RNAi can be used in combination with other treatment modalities, such as chemotherapy, radiation therapy, and other treatments. In an exemplary embodiment, a chemotherapy agent is used in combination with RNAi. In a further exemplary embodiment, GEMZAR (gemcitabine HCl) chemotherapy is used with RNAi.

Treatment of certain diseases by RNAi may require introduction of the RNA into the disease cells. RNA can be directly introduced into a cell, or introduced extracellularly into a cavity, interstitial space, into the circulation of a patient, or introduced orally, for example. Physical methods of introducing nucleic acids, such as injection directly into a cell or extracellular injection into a patient, may also be used. RNA may be introduced into vascular or extravascular circulation, the blood or lymph system, or the cerebrospinal fluid, for example. RNA may be introduced into an embryonic stem cell or another multipotent cell, which may be derived from a patient. Physical methods of introducing nucleic acids include injection of a solution containing the RNA, bombardment by particles covered by the RNA, soaking cells or tissue in a solution of the RNA, or electroporation of cell membranes in the presence of the RNA. A viral construct packaged into a viral particle may be used to introduce an expression construct into a cell, with the construct expressing the RNA. Other methods known in the art for introducing nucleic acids to cells may be used, such as lipid-mediated carrier transport, chemical-mediated transport, and the like. The RNA may be introduced along with components that perform one or more of the following activities: enhance RNA uptake by the cell, promote annealing of the duplex strands, stabilize the annealed strands, or otherwise increase inhibition of the target gene.

Exemplary RNA of the invention can be used alone or as a component of a kit having at least one reagent for carrying out in vitro or in vivo introduction of the RNA to a cell, tissue/fluid, or patient. Exemplary components of a kit include dsRNA and a vehicle that promotes introduction of the dsRNA. A kit may also include instructions for using the kit.

Certain exemplary embodiments of the invention provide compositions and methods for cleavage of mRNA by ribozymes having nucleotide sequences complementary to one or more regions in the mRNA, thereby attenuating the translation of the mRNA. Examples of regions in mRNA that can be targeted by ribozymes include coding regions, particularly coding regions corresponding to catalytic or other functional activities of a target protein, such as substrate binding. These compositions and methods may be used to treat a disorder characterized by abnormal or undesired target nucleic acid expression.

In certain exemplary embodiments, nucleic acid molecules of the invention may be used for gene therapy in individuals having cells that are aberrant in gene expression of a target. For example, recombinant cells that have been engineered ex vivo (which can include an individual's own cells) can be introduced into an individual where the cells produce the desired target protein to thereby treat the individual.

d. Methods of Screening Using Nucleic Acids

Nucleic acid expression assays are useful for drug screening to identify compounds that modulate CAT nucleic acid expression.

Exemplary embodiments of the invention thus provide methods for identifying a compound that can be used to treat a disease associated with differential expression of a CAT gene, especially cancer. Exemplary methods can typically include assaying the ability of a compound to modulate the expression of a target nucleic acid to thereby identify a compound that can be used to treat a disorder characterized by undesired target nucleic acid expression. The assays can be performed in cell-based or cell-free systems. Examples of cell-based assays include cells naturally expressing target nucleic acid or recombinant cells genetically engineered to express specific target nucleic acid sequences.

Assays for target nucleic acid expression can involve direct assay of target nucleic acid levels, such as mRNA levels, or on collateral compounds involved in a signal pathway. Further, the expression of genes that are up- or down-regulated in response to a signal pathway can also be assayed. In these embodiments, the regulatory regions of these genes can be operably linked to a reporter gene such as luciferase.

Thus, in exemplary embodiments, modulators of gene expression of a target can be identified in methods wherein a cell is contacted with a candidate agent and the expression of target mRNA determined. The level of expression of target mRNA in the presence of the candidate agent is compared to the level of expression of target mRNA in the absence of the candidate agent. The candidate agent can then be identified as a modulator of target nucleic acid expression based on this comparison and may be used, for example, to treat a disorder characterized by aberrant target nucleic acid expression. When expression of target mRNA is statistically significantly greater in the presence of the candidate agent than in its absence, the candidate agent is identified as a stimulator (agonist) of nucleic acid expression. When nucleic acid expression is statistically significantly less in the presence of the candidate agent than in its absence, the candidate compound is identified as an inhibitor (antagonist) of nucleic acid expression.

11. Arrays and Expression Analysis

"Array" (interchangeably referred to as "microarray") typically refers to an arrangement of at least one, but more typically at least two, nucleic acid molecules, proteins, or antibodies on a substrate. In certain exemplary arrangements, at least one of the nucleic acid molecules, proteins, or antibodies typically represents a control or standard, and other nucleic acid molecules, proteins, or antibodies are of diagnostic or therapeutic interest. In exemplary embodiments, the arrangement of nucleic acid molecules, proteins, or antibodies on the substrate is such that the size and signal intensity of each labeled complex (e.g., formed between each nucleic acid molecule and a complementary nucleic acid, or between each protein and a ligand or antibody, or between each antibody and a protein to which the antibody specifically binds) is individually distinguishable.

An "expression profile" is a representation of target expression in a sample. A nucleic acid expression profile can be produced using, for example, arrays, sequencing, hybridization, or amplification technologies for nucleic acids from a sample. A protein expression profile can be produced using, for example, arrays, gel electrophoresis, mass spectrometry, or antibodies (and, optionally, labeling moieties) which specifically bind proteins. Nucleic acids, proteins, or antibodies can be attached to a substrate or provided in solution, and their detection can be based on methods well known in the art.

A substrate includes, but is not limited to, glass, paper, nylon or other type of membrane, filter, chip, metal, or any other suitable solid or semi-solid (e.g., gel) support.

Exemplary arrays can be prepared and used according to the methods described in U.S. Pat. No. 5,837,832; PCT application WO95/11995; Lockhart et al., 1996, *Nat. Biotech.* 14: 1675-1680; Schena et al., 1996; *Proc. Natl. Acad. Sci.* 93: 10614-10619; and U.S. Pat. No. 5,807,522. Exemplary embodiments of the invention also provide antibody arrays (see, e.g., de Wildt et al. (2000) *Nat. Biotechnol.* 18:989-94).

Certain exemplary embodiments of the invention provide a nucleic acid array for assaying target expression, which can be composed of single-stranded nucleic acid molecules, usually either synthetic antisense oligonucleotides or fragments of cDNAs, fixed to a solid support. The oligonucleotides can be, for example, about 6-60 nucleotides in length, about 15-30 nucleotides in length, or about 20-25 nucleotides in length.

To produce oligonucleotides to a target nucleic acid molecule for an array, the target nucleic acid molecule of interest is typically examined using a computer algorithm to identify oligonucleotides of defined length that are unique to the nucleic acid molecule, have a GC content within a range suitable for hybridization, and lack predicted secondary structure that may interfere with hybridization. In certain instances, it may be desirable to use pairs of oligonucleotides on an array. In exemplary embodiments, the "pairs" can be identical, except for one nucleotide (which can be located in the center of the sequence, for example). The second oligonucleotide in the pair (mismatched by one) serves as a control. Any number of oligonucleotide pairs may be utilized.

Oligonucleotides can be synthesized on the surface of a substrate, such as by using a light-directed chemical process or by using a chemical coupling procedure and an ink jet application apparatus (e.g., PCT application WO95/251116).

In some exemplary embodiments, an array can be used to diagnose or monitor the progression of disease, for example, by assaying target expression.

For example, an oligonucleotide probe specific for a target can be labeled by standard methods and added to a biological sample from a patient under conditions that allow for the formation of hybridization complexes. After an incubation period, the sample can be washed and the amount of label (or signal) associated with hybridization complexes can be quantified and compared with a standard value. If complex formation in the patient sample is significantly altered (higher or lower) in comparison to a normal (e.g., healthy) standard, or is similar to a disease standard, this differential expression can be diagnostic of a disorder.

By analyzing changes in patterns of target expression, disease may be diagnosed at earlier stages before a patient is symptomatic. In exemplary embodiments of the invention, arrays or target expression analysis methods can be used to formulate a diagnosis or prognosis, to design a treatment regimen, and/or to monitor the efficacy of treatment. For example, a treatment dosage can be established that causes a change in target expression patterns indicative of successful treatment, and target expression patterns associated with the onset of undesirable side effects can be avoided. In further exemplary embodiments, assays of target expression can be repeated on a regular basis to determine if the level of target expression in a patient begins to approximate that which is observed in a normal subject. The results obtained from successive assays may be used to show the efficacy of treatment over a period ranging from several days to years, for example.

Exemplary arrays of the invention can also be used to screen candidate agents, such as to identify agents that produce a target expression profile similar to that caused by known therapeutic agents, with the expectation that agents that cause a similar expression profile of a target may have similar therapeutic effects and/or modes of action on the target.

EXAMPLES

Exemplary embodiments of the invention are further described in the following examples, which do not limit the scope of the invention.

1. Tissue Samples and Cell Lines

Tissue Processing and Preparation of Single Cell Suspensions from Tissue

Tissue samples (e.g., normal tissues or disease tissues such as surgically resected neoplastic or metastatic lesions) can be procured from clinical sites and transported in transport buffer. Tissues can be collected as remnant tissues following surgical resection of cancer (or other disease) tissues. Remnant tissues are supplied following processing for pathological diagnosis according to proper standards of patient care. Normal tissue specimens can be normal tissue adjacent to tumors (or other disease tissue) that is collected during tumor resection. Normal tissue from healthy patients not having cancer (or other disease of interest) can also be included, such as to reduce the contribution from pre-neoplastic changes that may exist in normal adjacent tissue. Procurement of tissue samples is carried out in an anonymous manner in compliance with federally mandated ethical and legal guidelines (HIPAA) and in accordance with clinical institution ethical review board and internal institutional review board guidelines.

Tissue can be crudely minced and incubated for 20-30 minutes with periodic agitation at 37° C. in Enzyme Combination #1 (200 units collagenase, cat #C5894 Sigma; 126 μg DNAse I, cat #D4513 Sigma (in 10 mM Tris/HCl pH7.5); 50 mM NaCl; 10 mM $MgCl_2$; 0.05% elastase, cat #E7885 Sigma) (additionally, hyaluronidase enzyme may also be utilized). D-PBS is added at 3× the volume of the enzyme combination, the tissue finely minced, and disassociated cells passed through a 200 μm filter. The cells are washed twice with D-PBS. Red blood cells are lysed with PharMLyse (BD Biosciences) when necessary. Cell number and viability are determined by PI exclusion (GUAVA). Cells at a total cell number greater than $20 \times 10^6$ are sorted using a high-speed sorter (MoFlo Cytomation) for epithelial cells (EpCAM positive).

The remaining undigested tissue is incubated for 20-30 minutes with periodic agitation at 37° C. in Enzyme Combination #2 (1× Liberase Blendzyme 1, cat #988-417 Roche; 1× Liberase Blendzyme 3, cat #814-184 Roche; 0.05% elastase, cat #E7885 Sigma). D-PBS is added at 3× the volume of the enzyme combination, and the tissue finely minced until tissue is completely disassociated. The cells are passed through a 200 μm filter, washed twice with D-PBS, and pooled with cells from the Enzyme Combination #1 digestion.

Cells are passed through a 70 μm filter for single cell suspension, and cell number and viability are determined by PI exclusion (GUAVA). When needed, red blood cells are lysed with PharMLyse (BD Biosciences). Cells are incubated in 20 ml of 1× PharMLyse in D-PBS for 30 seconds with gentle agitation and cells pelleted at 300× g for 5 minutes at 4° C. Cells are washed once in D-PBS and cell number and viability are recalculated by PI exclusion using the GUAVA. Cells at a total cell number greater than $20 \times 10^6$ are sorted using a high-speed sorter (MoFlo Cytomation) for epithelial cells (EpCAM positive).

Single cell suspensions can also be prepared from tissue samples as follows: specimens are washed in DTT for 15 min, digested with Dispase (30-60 min), then filtered twice (380 μm/74 μm) before red blood cells are removed through addition of ACK lysis buffer. Epithelial (EpCAM) and leukocyte (CD45) content and cellular viability (PI exclusion) can be determined through flow cytometry analysis (LSR I, BD Biosciences, San Jose, Calif.).

The epithelial content of both disease and normal specimens can be enriched through depletion of immune CD45- positive cells by flow cytometry or purification of Epithelial Cell Surface Antigen (ECSA/EpCam)-positive cells by bead capture.

Bead capture of epithelial cells can be performed using a Dynal CELLection Epithelial Enrich kit (Invitrogen, Carlsbad, Calif.) as follows. Dynal CELLection beads at a concentration of $2\times10^8$ beads are incubated with $1\times10^8$ cells in HBSS with 10% fetal calf serum for 30 minutes at 4° C. Cells and beads are placed in a magnet system Dynal MPC for 2 minutes. Bead/cell complexes are washed in RPMI 1640 media with 1% fetal calf serum. Cells are released from the bead complex with 15 minute incubation with DNase with agitation in RPMI with 1% fetal calf serum.

DynalBead cell depletion of CD45 cells can be carried out as follows. DynalBead M-450 CD45 beads and cells are incubated at a concentration of 250 µl beads per $2\times10^7$ cells for 30 minutes at 4° C. Bead/cell complexes are washed in DPBS buffer with 2% fetal bovine serum. Cells and beads are placed in a magnet system Dynal MPC for 2 minutes. The supernatant contains EpCAM enriched cells.

Cell Line Culture

Cell lines can be obtained from the American Type Culture Collection (ATCC, Manassas, Va.). Cell lines can be grown in a culturing medium that is supplemented as necessary with growth factors and serum, in accordance with the ATCC guidelines for each particular cell line. Cultures are established from frozen stocks in which the cells are suspended in a freezing medium (cell culture medium with 10% DMSO [v/v]) and flash frozen in liquid nitrogen. Frozen stocks prepared in this way are stored in liquid nitrogen vapor. Cell cultures are established by rapidly thawing frozen stocks at 37° C. Thawed stock cultures are slowly transferred to a culture vessel containing a large volume of supplemented culture medium. For maintenance of culture, cells are seeded at $1\times10^5$ cells/per ml in medium and incubated at 37° C. until confluence of cells in the culture vessel exceeds 50% by area. At this time, cells are harvested from the culture vessel using enzymes or EDTA where necessary. The density of harvested, viable cells is estimated by hemocytometry and the culture reseeded as above. A passage of this nature is repeated no more than 25 times, at which point the culture is destroyed and reestablished from frozen stocks as described above.

Alternatively, cells (e.g., adipocytes such as differentiated subcutaneous or visceral adipocytes) can be obtained from commercial sources, which may provide the cells seeded into T-75 tissue culture flasks. Upon arrival in the laboratory, the media is removed and replaced with DMEM/Ham's F-12 medium (1:1 v/v) supplemented with HEPES pH 7.4, FBS, biotin, pantothenate, human insulin, dexamethasone, penicillin-streptomycin, and Amphotercin B. The cells are cultured for two days and then harvested with versene before enrichment of proteins.

Alternatively, for secreted protein analysis, cells can be grown under routine tissue culture conditions in 490 $cm^2$ roller bottles at an initial seeding density of approximately 15 million cells per roller bottle. When the cells reach ~70-80% confluence, the culturing media is removed, the cells are washed 3 times with D-PBS and once with CD293 protein-free media (Invitrogen cat #11913-019), and the culturing media is replaced with CD293 for generating conditioned media. Cells are incubated for 72 hours in CD293 and the media is collected for analysis, such as mass spectrometry analysis of secreted proteins (30-300 ml). Cell debris is removed from the conditioned media by centrifugation at 300 g for 5 minutes and filtering through a 0.2 micron filter prior to analysis.

Alternatively, for secreted protein analysis, conditioned media collected from differentiated cells (e.g., visceral or subcutaneous adipocytes), can be obtained (e.g., from a commercial source). Conditioned medium is shipped on dry ice and maintained at −80° C. ahead of protein capture. Cells are isolated from tissue and expanded to passage 2 (P2) to passage 4 (P4) prior to differentiation. Media is changed and cells are grown in conditioned medium for three days prior to harvesting. Enriching for proteins such as secreted proteins can then be carried out.

2. Cloning and Expression of Target Proteins cDNA Retrieval

Peptide sequences can be searched using the BLAST algorithm against relevant protein sequence databases to identify the corresponding full-length protein (reference sequence). Each full-length protein sequence can then be searched using the BLAST algorithm against a human cDNA clone collection. For each sequence of interest, clones can be pulled and streaked onto LB/Ampicillin (100 µg/ml) plates. Plasmid DNA is isolated using Qiagen spin mini-prep kit and verified by restriction digest. Subsequently, the isolated plasmid DNA is sequence verified against the reference full-length protein sequence. Sequencing reactions are carried out using Applied Biosystems BigDye Terminator kit followed by ethanol precipitation. Sequence data is collected using the Applied Biosystems 3700 Genetic Analyzer and analyzed by alignment to the reference full-length protein sequence using the Clone Manager alignment tool.

PCR

PCR primers are designed to amplify the region encoding the full-length protein and/or any regions of the protein that are of interest for expression (e.g., antigenic or hydrophilic regions as determined by the Clone Manager sequence analysis tool). Primers also contain 5' and 3' overhangs to facilitate cloning (see below). PCR reactions contain 2.5 units Platinum Taq DNA Polymerase High Fidelity (Invitrogen), 50 ng cDNA plasmid template, 1 µM forward and reverse primers, 800 µM dNTP cocktail (Applied Biosystems), and 2 mM $MgSO_4$. After 20-30 cycles (94° C. for 30 seconds, 55° C. for 1 minute, and 73° C. for 2 minutes), the resulting product is verified by sequence analysis and quantitated by agarose gel electrophoresis.

Construction of Entry Clones

PCR products are cloned into an entry vector for use with the Gateway recombination based cloning system (Invitrogen). These vectors include pDonr221, pDonr201, pEntr/D-TOPO, or pEntr/SD/D-TOPO and are used as described in the cloning methods below.

TOPO Cloning into pEntr/D-TOPO or pEntr/SD/D-TOPO

For cloning using this method, the forward PCR primer contains a 5' overhang containing the sequence "CACC". PCR products are generated as described above and cloned into the entry vector using the Invitrogen TOPO® cloning kit. Reactions are typically carried out at room temperature for 10 minutes and subsequently transformed into TOP10 chemically competent cells (Invitrogen, CA). Candidate clones are picked, and plasmid DNA is prepared using a Qiagen spin mini-prep kit and screened by restriction enzyme digestion. Inserts are subsequently sequence-verified as described above.

Gateway Cloning into pDonr201 or pDonr221

For cloning using this method, PCR primers contain forward and reverse 5' overhangs. PCR products are generated as described above. Protein-encoding nucleic acid molecules are recombined into the entry vector using the Invitrogen Gateway BP Clonase enzyme mix. Reactions are typically carried out at 25° C. for 1 hour, treated with Proteinase K at 37° C. for 10 minutes, and transformed into Library Efficiency DH5α chemically competent cells (Invitrogen, CA). Candidate clones are picked, plasmid DNA is prepared using a Qiagen spin mini-prep kit, and screened by restriction enzyme digestion. Inserts are subsequently sequence-verified as described above.

Construction of Expression Clones

Protein-encoding nucleic acid molecules are transferred from the entry construct into a series of expression vectors using the Gateway LR Clonase enzyme mix. Reactions are typically carried out for 1 hour at 25° C., treated with Proteinase K at 37° C. for 10 minutes, and subsequently transformed into Library Efficiency DH5a chemically competent cells (Invitrogen). Candidate clones are picked, plasmid DNA is prepared using a Qiagen spin mini-prep kit, and screened by restriction enzyme digestion. Expression vectors include, but are not limited to, pDest14, pDest15, pDest17, pDest8, pDest10 and pDest20. These vectors allow expression in systems such as E. coli and recombinant baculovirus. Other vectors not listed here allow expression in yeast, mammalian cells, or in vitro.

Expression of Recombinant Proteins in E. coli

Constructs are transformed into one or more of the following host strains: BL21 SI, BL21 AI, (Invitrogen), Origami B (DE3), Origami B (DE3) pLysS, Rosetta (DE3), Rosetta (DE3) pLysS, Rosetta-Gami (DE3), Rosetta-Gami (DE3) pLysS, or Rosetta-Gami B (DE3) pLysS (Novagen). The transformants are grown in LB with or without NaCl and with appropriate antibiotics, at temperatures in the range of 20-37° C., with aeration. Expression is induced with the addition of IPTG (0.03-0.30 mM) or NaCl (75-300 mM) when the cells are in mid-log growth. Growth is continued for one to 24 hours post-induction. Cells are harvested by centrifugation in a Sorvall RC-3C centrifuge in a H6000A rotor for 10 minutes at 3000 rpm at 4° C. Cell pellets are stored at −80° C.

Expression of Recombinant Proteins Using Baculovirus

Recombinant proteins are expressed using baculovirus in Sf21 fall army worm ovarian cells. Recombinant baculoviruses are prepared using the Bac-to-Bac system (Invitrogen) per the manufacturer's instructions. Proteins are expressed on the large scale in Sf900II serum-free medium (Invitrogen) in a 10 L bioreactor tank (27° C., 130 rpm, 50% dissolved oxygen for 48 hours).

3. Recombinant Protein Purification

Recombinant proteins can be purified from E. coli and/or insect cells using a variety of standard chromatography methods. Briefly, cells are lysed using sonication or detergents. The insoluble material is pelleted by centrifugation at 10,000×g for 15 minutes. The supernatant is applied to an appropriate affinity column. For example, His-tagged proteins are separated using a pre-packed chelating sepharose column (Pharmacia) or GST-tagged proteins are separated using a glutathione sepharose column (Pharmacia). After using the affinity column, proteins are further separated using various techniques, such as ion exchange chromatography (columns from Pharmacia) to separate on the basis of electrical charge or size exclusion chromatography (columns from Tosohaas) to separate on the basis of molecular weight, size, and shape.

Expression and purification of the protein can also be achieved using either a mammalian cell expression system or an insect cell expression system. The pUB6/V5-His vector system (Invitrogen, CA) can be used to express cDNA in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6×His) sequence for rapid purification on PROBOND resin (Invitrogen, CA). Transformed cells are selected on media containing blasticidin.

Spodoptera frugiperda (Sf9) insect cells are infected with recombinant Autographica californica nuclear polyhedrosis virus (baculovirus). The polyhedrin gene is replaced with the cDNA by homologous recombination and the polyhedrin promoter drives cDNA transcription. The protein is synthesized as a fusion protein with 6×His which enables purification as described above. Purified proteins can be used to produce antibodies.

4. Chemical Synthesis of Proteins

Proteins or portions thereof can be produced not only by recombinant methods (such as described above), but also by using chemical methods well known in the art. Solid phase peptide synthesis can be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl) groups. The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full-length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20).

Automated synthesis can also be carried out on machines such as the 431A peptide synthesizer (Applied Bio systems, Foster City, Calif.). A protein or portion thereof can be purified by preparative high performance liquid chromatography and its composition confirmed by amino acid analysis or by sequencing (Creighton, 1984, Proteins, Structures and Molecular Properties, WH Freeman, New York N.Y.).

5. Antibody Production

Polyclonal Antibodies

Polyclonal antibodies against recombinant proteins can be raised in rabbits (Green Mountain Antibodies, Burlington, Vt.). Briefly, two New Zealand rabbits are immunized with 0.1 mg of antigen in complete Freund's adjuvant. Subsequent immunizations are carried out using 0.05 mg of antigen in incomplete Freund's adjuvant at days 14, 21, and 49. Bleeds are collected and screened for recognition of the antigen by solid phase ELISA and Western blot analysis. The IgG fraction is separated by centrifugation at 20,000×g for 20 minutes followed by a 50% ammonium sulfate cut. The pelleted protein is resuspended in 5 mM Tris and separated by ion exchange chromatography. Fractions are pooled based on IgG content. Antigen-specific antibody is affinity purified using Pierce AminoLink resin coupled to the appropriate antigen.

Isolation of Antibody Fragments Directed Against a Protein Target from a Library of scFvs Naturally occurring V-genes isolated from human PBLs can be constructed into a library of antibody fragments which contain reactivities against a target protein to which the donor may or may not have been exposed (see, for example, U.S. Pat. No. 5,885,793, incorporated herein by reference in its entirety).

Rescue of the library: A library of scFvs is constructed from the RNA of human PBLs, as described in PCT publication WO 92/01047. To rescue phage displaying antibody fragments, approximately $10^9$ E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, $2 \times 10^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 rpm. for 10 min. and the pellet resuspended in 2 liters of 2×TY containing 100 µg/ml ampicillin and 50 µg/ml kanamycin and grown overnight. Phage are prepared as described in PCT publication WO 92/01047.

Preparation of M13 delta gene III: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 rpm for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 2001, Molecular Cloning: A Laboratory Manual. 3rd. ed., Cold Spring Harbor Laboratory Press, Cold Spring Harbor, N.Y.), resuspended in 2 ml PBS and passed through a 0.45 µm filter (Minisart NML; Sartorius) to give a final concentration of approximately $10^{13}$ transducing units/ml (ampicillin-resistant clones).

Panning of the library: Immunotubes (Nunc) are coated overnight in PBS with 4 ml of either 100 µg/ml or 10 µg/ml of a protein target of interest. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over-and-under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under-and-over turntable after which the solution is immediately neutralized with 0.5 ml of 1.0 M Tris-HCl, pH 7.4. Phages are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of binders: Eluted phage from the 3rd and 4th rounds of selection are used to infect E. coli HB 2151 and soluble scFv is produced (Marks et al., 1991, J. Mol. Biol. 222: 581-597) from single colonies for assay. ELISAs are performed with microtitre plates coated with either 10 µg/ml of the protein target of interest in 50 mM bicarbonate pH 9.6. Clones positive in ELISA are further characterized by PCR fingerprinting (see, e.g., PCT publication WO 92/01047) and then by sequence analysis.

Monoclonal Antibodies a) Materials:

1. Complete Media No Sera (CMNS) for washing of the myeloma and spleen cells; Hybridoma medium CM-HAT (Cell Mab (BD), 10% FBS (or HS); 5% Origen HCF (hybridoma cloning factor) containing 4 mM L-glutamine and antibiotics) to be used for plating hybridomas after the fusion.

2. Hybridoma medium CM-HT (no aminopterin) (Cell Mab (BD), 10% FBS 5% Origen HCF containing 4 mM L-glutamine and antibiotics) to be used for fusion maintenance is stored in the refrigerator at 4-6° C. The fusions are fed on days 4, 8, and 12, and subsequent passages. Inactivated and pre-filtered commercial fetal bovine serum (FBS) or horse serum (HS) are thawed and stored in the refrigerator at 4° C. and is pretested for myeloma growth from single cells prior to use.

3. The L-glutamine (200 mM, 100× solution), which is stored at −20° C., is thawed and warmed until completely in solution. The L-glutamine is dispensed into media to supplement growth. L-glutamine is added to 2 mM for myelomas and 4 mM for hybridoma media. Further, the penicillin, streptomycin, amphotericin (antibacterial-antifungal stored at −20° C.) is thawed and added to Cell Mab Media to 1%.

4. Myeloma growth media is Cell Mab Media (Cell Mab Media, Quantum Yield, from BD, which is stored in the refrigerator at 4° C. in the dark), to which is added L-glutamine to 2 mM and antibiotic/antimycotic solution to 1% and is called CMNS.

5. One bottle of PEG 1500 in Hepes (Roche, N.J.) is prepared.

6. 8-Azaguanine is stored as the dried powder supplied by SIGMA at −700° C. until needed. One vial/500 ml of media is reconstituted and the entire contents are added to 500 ml media (e.g., 2 vials/liter).

7. Myeloma Media is CM which has 10% FBS (or HS) and 8-Aza (1×) stored in the refrigerator at 4° C.

8. Clonal cell medium D (Stemcell, Vancouver) contains HAT and methyl cellulose for semi-solid direct cloning from the fusion. This comes in 90 ml bottles with a CoA and is melted at 37° C. in a waterbath in the morning of the day of the fusion. The cap is loosened and the bottle is left in a $CO_2$ incubator to sufficiently gas the medium D and bring the pH down.

9. Hybridoma supplements HT [hypoxanthine, thymidine] to be used in medium for the section of hybridomas and maintenace of hybridomas through the cloning stages, respectively.

10. Origen HCF can be obtained directly from Igen and is a cell supernatant produced from a macrophage-like cell-line. It can be thawed and aliqouted to 15 ml tubes at 5 ml per tube and stored frozen at −20° C. Positive hybridomas are fed HCF through the first subcloning and are gradually weaned (individual hybridomas can continue to be supplemented, as needed). This and other additives are typically more effective in promoting new hybridoma growth than conventional feeder layers.

b) Procedure:

To generate monoclonal antibodies, mice are immunized with 5-50 µg of antigen, either intra-peritoneally (i.p.) or by intravenous injection in the tail vein (i.v.). The antigen used can be a recombinant target protein of interest, for example. The primary immunization takes place two months prior to the harvesting of splenocytes from the mouse, and the immunization is typically boosted by i.v. injection of 5-50 µg of antigen every two weeks. At least one week prior to the expected fusion date, a fresh vial of myeloma cells is thawed and cultured. Several flasks of different densities can be maintained so that a culture at the optimum density is ensured at the time of fusion. An optimum density can be $3-6\times10^5$ cells/ml, for example. 2-5 days before the scheduled fusion, a final immunization of approximately 5 µg of antigen in PBS is administered (either i.p. or i.v).

Myeloma cells are washed with 30 ml serum free media by centrifugation at 500 g at 4° C. for 5 minutes. Viable cell density is determined in resuspended cells using hemocytometry and vital stains. Cells resuspended in complete growth medium are stored at 37° C. during the preparation of splenocytes. Meanwhile, to test aminopterin sensitivity, $1\times10^6$ myeloma cells are transferred to a 15 ml conical tube and centrifuged at 500 g at 4° C. for 5 minutes. The resulting pellet is resuspended in 15 ml of HAT media and cells plated at 2 drops/well on a 96-well plate.

To prepare splenocytes from immunized mice, the animals are euthanised and submerged in 70% ethanol. Under sterile conditions, the spleen is surgically removed and placed in 10 ml of RPMI medium supplemented with 20% fetal calf serum in a petri dish. Cells are extricated from the spleen by infusing the organ with medium >50 times using a 21 g syringe.

Cells are harvested and washed by centrifugation (at 500 g at 4° C. for 5 minutes) with 30 ml of medium. Cells are resuspended in 10 ml of medium and the density of viable cells determined by hemocytometry using vital stains. The splenocytes are mixed with myeloma cells at a ratio of 5:1 (spleen cells: myeloma cells). Both the myeloma and spleen cells are washed twice more with 30 ml of RPMI-CMNS, and the cells are spun at 800 rpm for 12 minutes.

Supernatant is removed and cells are resuspended in 5 ml of RPMI-CMNS and are pooled to fill volume to 30 ml and spun down as before. Then, the pellet is broken up by gently tapping on the flow hood surface and resuspending in 1 ml of BMB REG1500 (prewarmed to 37° C.) dropwise with a 1 cc needle over 1 minute.

RPMI-CMNS to the PEG cells and RPMI-CMNS are added to slowly dilute out the PEG. Cells are centrifuged and diluted in 5 ml of Complete media and 95 ml of Clonacell Medium D (HAT) media (with 5 ml of HCF). The cells are plated out 10 ml per small petri plate.

Myeloma/HAT control is prepared as follows: dilute about 1000 P3X63 Ag8.653 myeloma cells into 1 ml of medium D and transfer into a single well of a 24-well plate. Plates are placed in an incubator, with two plates inside of a large petri plate, with an additional petri plate full of distilled water, for 10-18 days under 5% $CO_2$ overlay at 37° C. Clones are picked from semisolid agarose into 96-well plates containing 150-200 µl of CM-HT. Supernatants are screened 4 days later in ELISA, and positive clones are moved up to 24-well plates. Heavy growth requires changing of the media at day 8 (+/−150 ml). The HCF can be further decreased to 0.5% (gradually −2%, then 1%, then 0.5%) in the cloning plates.

6. Liquid Chromatography and Mass Spectrometry (LC/MS)

For LC/MS analysis, proteins are reduced in 2.5 mM DTT for 1 hour at 37° C., and alkylated with ICAT™ reagent according to the procedures recommended by the manufacturer (Applied Biosystems, Framingham, Mass.). The reaction is quenched by adding excess DTT. Proteins are digested using sequencing grade modified trypsin overnight at 37° C. followed by desalting using 3 cc Oasis HLB solid phase extraction columns (Waters, Milford, Mass.) and vacuum drying. Cysteine-containing peptides are purified by avidin column (Applied Biosystems, Framingham, Mass.). The peptides are reconstituted in buffer A (0.1% formic acid in water) and separated over a C18 monomeric column (150 mm, 150 µm i.d., Grace Vydac 238EV5, 5 µm) at a flow rate of 1.5 µl/min with a trap column. Peptides are eluted from the column using a gradient, 3%-30% buffer B (0.1% formic acid in 90% acetonitrile) in 215 mM, 30%-90% buffer B in 30 min. Eluted peptides are analyzed using an online QSTAR XL system (MDS/Sciex, Toronto, ON). Peptide ion peaks from the map are automatically detected with RESPEC™ (PPL Inc., UK).

The sequence-composition of peptides detected, for example, at higher levels in disease samples (or drug-resistant samples) relative to adjacent normal tissue (or drug-sensitive samples) can be resolved through tandem mass spectrometry and database analysis. For data analysis, peptide ion peaks of LC/MS maps from normal and disease samples can be aligned based on mass to charge ratio (m/z), retention time (Rt), and charge state (z). The list of aligned peptide ions is loaded into Spotfire™ (Spotfire Inc. Somerville, Mass.). Intensities can be normalized before further differential analysis between disease and normal samples. Differentially expressed ions are manually verified before LC-MS/MS-based peptide sequencing and database searching for protein/protein identification.

For intensity normalization and expression analysis, a heat map can be constructed by sorting the rows by the ratio of the mean intensity in the disease samples to the mean intensity of the normal samples. Rows are included if there is at least one MS/MS identification of an ion in the row. The display colors are determined for each row separately by assigning black to the median intensity in the row, green to the lowest intensity in the row, and red to the highest intensity.

Using a mass spectrometry procedure such as this, a comprehensive analysis of proteins differentially expressed by disease cells (or drug resistant cells, for example) compared with normal cells (or cells responsive/sensitive to a drug, for example) can be carried out.

7. mRNA Expression Analysis

Expression of target mRNA can be quantitated by RT-PCR using TaqMan® technology. The Taqman® system couples a 5' fluorogenic nuclease assay with PCR for real-time quantitation. A probe is used to monitor the formation of the amplification product.

Total RNA can be isolated from disease model cell lines using an RNEasy Kit® (Qiagen, Valencia, Calif.) with DNase treatment (per the manufacturer's instructions). Normal human tissue RNAs can be acquired from commercial vendors (e.g., Ambion, Austin, Tex.; Stratagene, La Jolla, Calif.; BioChain Institute, Newington, N.H.), as well as RNAs from matched disease/normal tissues.

Target transcript sequences can be identified for differentially expressed peptides by database searching using a search algorithm such as BLAST. TaqMan® assays (PCR primer/probe sets) specific for those transcripts can be obtained from Applied Biosystems (AB) as part of the Assays on Demand™ product line or by custom design through the AB Assays by Design$^{SM}$ service. If desired, the assays can be designed to span exon-exon borders so as not to amplify genomic DNA.

RT-PCR can be accomplished using AmpliTaq Gold® and MultiScribe™ reverse transcriptase in the One Step RT-PCR Master Mix reagent kit (AB) (according to the manufacturer's instructions). Probe and primer concentrations are 250 nM and 900 nM, respectively, in a 15 µl reaction. For each experiment, a master mix of the above components is made and aliquoted into each optical reaction well. Eight nanograms of total RNA is used as template. Quantitative RT-PCR can be performed using the ABI Prism® 7900HT Sequence Detection System (SDS). The following cycling parameters are used: 48° C. for 30 min. for one cycle; 95° C. for 10 min for one cycle; and 95° C. for 15 sec, 60° C. for 1 min. for 40 cycles.

SDS software can be utilized to calculate the threshold cycle ($C_T$) for each reaction, and $C_T$ values are used to quantitate the relative amount of starting template in the reaction. The $C_T$ values for each set of reactions can be averaged for all subsequent calculations Data can be analyzed to determine estimated copy number per cell. Gene expression can be quantitated relative to 18S rRNA expression and copy number estimated assuming $5 \times 10^6$ copies of 18S rRNA per cell. Alternatively, data can be analyzed for fold difference in expression using an endogenous control for normalization and expressed relative to a normal tissue or normal cell line reference. The choice of endogenous control can be determined empirically by testing various candidates against the cell line and tissue RNA panels and selecting the one with the least variation in expression. Relative changes in expression can be quantitated using the $2^{-\Delta\Delta C_T}$ method (Livak et al., 2001, Methods 25: 402-408; User bulletin #2: ABI Prism 7700 Sequence Detection System). Alternatively, total RNA can be quantitated using a RiboGreen RNA Quantitation Kit according to manufacturer's instructions and the percentage mRNA expression calculated using total RNA for normalization. Percentage knockdown can then be calculated relative to a no addition control.

8. Flow Cytometry (FACS) Analysis

Flow cytometry is interchangeably referred to as fluorescence-activated cell sorting (FACS). Quantitative flow cytometry can be used to compare the level of expression of a protein on disease cells to the level found on normal cells, for example.

Expression levels of a target protein on primary tissue samples can be quantified using the Quantum Simply Cellular System (Bangs Laboratories, Fishers, Ind.) and a target-specific antibody. Normal adjacent and disease tissues can be processed into single cell suspensions, as described above, which can be stained for various markers (e.g., the epithelial marker EpCam) and the target-specific antibody. At least $0.5 \times 10^6$ cells are typically used for each analysis. Cells are washed once with Flow Staining Buffer (0.5% BSA, 0.05% NaN3 in D-PBS). To the cells, 20 μl of each target-specific antibody are added. An additional 5 μl of anti-EpCam antibody conjugated to APC can be added when unsorted cells are used. Cells are incubated with antibodies for 30 minutes at 4° C. Cells are washed once with Flow Staining Buffer and either analyzed immediately on an LSR flow cytometry apparatus or fixed in 1% formaldehyde and stored at 4° C. until LSR analysis. Antibodies used to detect a target can be PE-conjugated. PE-conjugated mouse IgG1k can used as an isotype control antibody. Cells are analyzed by flow cytometry and epitope copy number and the percentage of viable epithelial cells positive for target expression can be measured. Cell numbers and viability can be determined by PI exclusion (GUAVA) for cells isolated from both normal and disease tissue. Standard curve and samples can be analyzed on a LSR I (BDBiosciences, San Jose Calif.) flow cytometer. Antibody binding capacity for each lineage population can be calculated using geometric means and linear regression.

Expression levels of a target protein can be quantified in cell lines with QIFIKIT flow cytometric indirect immunofluoresence assay (Dako A/S) using a primary antibody to the target. Briefly, cells are detached with versene or trypsin and washed once with complete media and then PBS. $5 \times 10^5$ cells/sample are incubated with saturating concentration (10 μg/ml) of primary antibody for 60 minutes at 4° C. After washes, a FITC-conjugated secondary antibody (1:50 dilution) is added for 45 minutes at 4° C. QIFIKIT standard beads are simultaneously labeled with the secondary antibody. Binding of antibodies is analyzed by flow cytometry and specific antigen density is calculated by subtracting background antibody equivalent from antibody-binding capacity based on a standard curve of log mean fluorescence intensity versus log antigen binding capacity.

Cells can also be prepared for flow cytometry analysis (as well as other types of analysis) as follows: cells are incubated with 1:100 dilution of BrdU in culturing media for 2-4 hours (BrdU Flow Kit, cat #559619 BD Biosciences). Cells are washed 3 times with D-PBS and disassociated from the flask with versene. Cell numbers and viability can be determined by PI exclusion (GUAVA). Cells are washed once with Flow Staining Buffer (0.5% BSA, 0.05% $NaN_3$ in D-PBS). Cells are incubated with 400 μl of Cytofix/Cytoperm Buffer (BrdU Flow Kit, BD Biosciences) for 15-30 minutes at 4° C. Cells are washed once with Flow Staining Buffer and resuspended in 400 μl Cytoperm Plus Buffer (BrdU Flow Kit BD Biosciences). Cells are incubated for 10 minutes at 4° C. and washed once with 1× Perm/Wash Buffer (BrdU Flow Kit, BD Biosciences). Cells are incubated for 1 hour at 37° C. protected from light in DNAse solution (BrdU Flow Kit, BD Biosciences). Cells are washed once with 1× Perm/Wash Buffer and incubated for 20 min at room temperature with anti-BrdU FITC-conjugated antibody (BrdU Flow Kit, BD Biosciences), PE-conjugated active caspase 3 (BD Biosciences cat #550821), and PE mouse IgG2B isotype control. Cells are washed once with 1× Perm/Wash Buffer and resuspended in DAPI for LSR flow cytometry analysis.

9. Immunohistochemistry (IHC)

IHC of Tissue Sections

Paraffin embedded, fixed tissue sections (e.g., from disease tissue samples such as solid tumors or other cancer tissues) can be obtained from a panel of normal tissues as well as tumor (or other disease) samples with matched normal adjacent tissues, along with replicate sections (if desired). For example, for an initial survey of target expression, a panel of common cancer formalin-fixed paraffin-embedded (FFPE) tissue microarrays (TMAs) can be used for analysis, and such TMAs can be obtained from commercial sources (TriStar, Rockville, Md.; USBiomax, Rockville, Md.; Imgenex, San Diego, Calif.; Petagen/Abxis, Seoul, Korea). Sections can be stained with hemotoxylin and eosin and histologically examined to ensure adequate representation of cell types in each tissue section.

An identical set of tissues can be obtained from frozen sections for use in those instances where it is not possible to generate antibodies that are suitable for fixed sections. Frozen tissues do not require an antigen retrieval step.

Paraffin Fixed Tissue Sections

An exemplary protocol for hemotoxylin and eosin staining of paraffin embedded, fixed tissue sections is as follows. Sections are deparaffinized in three changes of xylene or xylene substitute for 2-5 minutes each. Sections are rinsed in two changes of absolute alcohol for 1-2 minutes each, in 95% alcohol for 1 minute, followed by 80% alcohol for 1 minute. Slides are washed in running water and stained in Gill solution 3 hemotoxylin for 3-5 minutes. Following a vigorous wash in running water for 1 minute, sections are stained in Scott's solution for 2 minutes. Sections are washed for 1 minute in running water and then counterstained in eosin solution for 2-3 minutes, depending upon the desired staining intensity. Following a brief wash in 95% alcohol, sections are dehydrated in three changes of absolute alcohol for 1 minute each and three changes of xylene or xylene substitute for 1-2 minutes each. Slides are coverslipped and stored for analysis.

Optimization of Antibody Staining

For each antibody, a positive and negative control sample can be generated using data from ICAT analysis of disease cell lines or tissues. Cells can be selected that are known to express low levels of a particular target as determined from the ICAT data, and this cell line can be used as a reference normal control. Similarly, a disease cell line that is determined to over-express the target can also be selected.

Antigen Retrieval

Sections are deparaffinized and rehydrated by washing 3 times for 5 minutes in xylene, two times for 5 minutes in 100% ethanol, two times for 5 minutes in 95% ethanol, and once for 5 minutes in 80% ethanol. Sections are then placed in endogenous blocking solution (methanol+2% hydrogen peroxide) and incubated for 20 minutes at room temperature. Sections are rinsed twice for 5 minutes each in deionized water and twice for 5 minutes in phosphate buffered saline (PBS), pH 7.4.

Alternatively, where necessary, sections are de-parrafinized by High Energy Antigen Retrieval as follows: sections are washed three times for 5 minutes in xylene, two times for 5 minutes in 100% ethanol, two times for 5 minutes in 95% ethanol, and once for 5 minutes in 80% ethanol. Sections are placed in a Coplin jar with dilute antigen retrieval solution (10 mM citrate acid, pH 6). The Coplin jar containing slides is placed in a vessel filled with water and microwaved on high for 2-3 minutes (700 watt oven). Following cooling for 2-3 minutes, steps 3 and 4 are repeated four times (depending on the tissue), followed by cooling for 20 minutes at room temperature. Sections are then rinsed in deionized water (two times for 5 minutes), placed in modified endogenous oxidation blocking solution (PBS+2% hydrogen peroxide), and rinsed for 5 minutes in PBS.

Alternatively, formalin fixed paraffin embedded tissues can be deparaffinized and processed for antigen retrieval using the EZ-retriever system (BioGenex, San Ramon, Calif.). EZ-antigen Retrieval common solution is used for deparaffinization and EZ-retrieval citrate-based buffer used for antigen retrieval. Samples are pre-blocked with non-serum protein block (Dako A/S, Glostrup, Denmark) for 15 min. Primary antibodies (at 2.5-5.0 µg/ml, for example) are incubated overnight at room temperature. Envision Plus system HRP (Dako A/S) is used for detection with diaminobenzidine (DAB) as substrate for horseradish peroxidase.

Blocking and Staining

Sections are blocked with PBS/1% bovine serum albumin (PBA) for 1 hour at room temperature followed by incubation in normal serum diluted in PBA (2%) for 30 minutes at room temperature to reduce non-specific binding of antibody. Incubations are performed in a sealed humidity chamber to prevent air-drying of the tissue sections. The choice of blocking serum is typically the same as the species of the biotinylated secondary antibody. Excess antibody is gently removed by shaking and sections covered with primary antibody diluted in PBA and incubated either at room temperature for 1 hour or overnight at 4° C. (care is taken that the sections do not touch during incubation). Sections are rinsed twice for 5 minutes in PBS, shaking gently. Excess PBS is removed by gently shaking. The sections are covered with diluted biotinylated secondary antibody in PBA and incubated for 30 minutes to 1 hour at room temperature in the humidity chamber. If using a monoclonal primary antibody, addition of 2% rat serum can be used to decrease the background on rat tissue sections. Following incubation, sections are rinsed twice for 5 minutes in PBS, shaking gently. Excess PBS is removed and sections incubated for 1 hour at room temperature in Vectastain ABC reagent (as per kit instructions). The lid of the humidity chamber is secured during all incubations to ensure a moist environment. Sections are rinsed twice for 5 minutes in PBS, shaking gently.

Developing and Counterstaining

Sections are incubated for 2 minutes in peroxidase substrate solution that is made up immediately prior to use as follows: 10 mg diaminobenzidine (DAB) dissolved in 10 ml of 50 mM sodium phosphate buffer, pH 7.4; 12.5 microliters 3% $CoCl_2/NiCl_2$ in deionized water; and 1.25 microliters hydrogen peroxide.

Slides are rinsed well three times for 10 minutes in deionized water and counterstained with 0.01% Light Green acidified with 0.01% acetic acid for 1-2 minutes, depending on the desired intensity of counterstain.

Slides are rinsed three times for 5 minutes with deionized water and dehydrated two times for 2 minutes in 95% ethanol; two times for 2 minutes in 100% ethanol; and two times for 2 minutes in xylene. Stained slides are mounted for visualization by microscopy.

Slides are scored manually using a microscope such as the Zeiss Axiovert 200M microscope (Carl Zeiss Microimaging, Thornwood, N.Y.). Representative images are acquired using 40x objective (400x magnification).

IHC Staining of Frozen Tissue Sections

For IHC staining of frozen tissue sections, fresh tissues are embedded in OCT in plastic mold, without trapping air bubbles surrounding the tissue. Tissues are frozen by setting the mold on top of liquid nitrogen until 70-80% of the block turns white at which point the mold is placed on dry ice. The frozen blocks are stored at −80° C. Blocks are sectioned with a cryostat with care taken to avoid warming to greater than −10° C. Initially, the block is equilibrated in the cryostat for about 5 minutes and 6-10 mm sections are cut sequentially. Sections are allowed to dry for at least 30 minutes at room temperature. Following drying, tissues are stored at 4° C. for short term and −80° C. for long term storage.

Sections are fixed by immersing in an acetone jar for 1-2 minutes at room temperature, followed by drying at room temperature. Primary antibody is added (diluted in 0.05 M Tris-saline [0.05 M Tris, 0.15 M NaCl, pH 7.4], 2.5% serum) directly to the sections by covering the section dropwise to cover the tissue entirely. Binding is carried out by incubation in a chamber for 1 hour at room temperature. Without letting the sections dry out, the secondary antibody (diluted in Tris-saline/2.5% serum) is added in a similar manner to the primary antibody and incubated as before (at least 45 minutes).

Following incubation, the sections are washed gently in Tris-saline for 3-5 minutes and then in Tris-saline/2.5% serum for another 3-5 minutes. If a biotinylated primary antibody is used, in place of the secondary antibody incubation, slides are covered with 100 µl of diluted alkaline phosphatase conjugated streptavidin, incubated for 30 minutes at room temperature and washed as above. Sections are incubated with alkaline phosphatase substrate (1 mg/ml Fast Violet; 0.2 mg/ml Napthol AS-MX phosphate in Tris-Saline pH 8.5) for 10-20 minutes until the desired positive staining is achieved at which point the reaction is stopped by washing twice with Tris-saline. Slides are counter-stained with Mayer's hematoxylin for 30 seconds and washed with tap water for 2-5 minutes. Sections are mounted with Mount coverslips and mounting media.

10. RNAi Assays in Cell Lines

RNAi Transfections

Expression of a target can be knocked down by transfection with small interfering RNA (siRNA) to that target. Synthetic siRNA oligonucleotides can be obtained from Dharmacon (Lafayette, Colo.) or Qiagen (Valencia, Calif.). For siRNA transfection, cells (e.g., disease cells) can be seeded into 96 well tissue culture plates at a density of 2,500 cells per well 24 hours before transfection. Culture medium is removed and 50 µl of reaction mix containing siRNA (final concentration 1 to 100 nM) and 0.4 µl of DharmaFECT4 (Dharmacon, Lafayette, Colo.) diluted in Opti-MEM is added to each well. An equal volume of complete medium follows and the cells are then incubated at 5% $CO_2$ at 37° C. for 1 to 4 days.

Alternatively, in the initial screening phase, RNAi can be performed using 100 nM (final) of Smartpools (Dharmacon, Lafayette, Colo.), pool of 4- for Silencing siRNA duplexes (Qiagen, Valencia, Calif.), or non-targeting negative control siRNA (Dharmacon or Qiagen). In the breakout phase, each individual duplex is used at 100 nM (final). In the titration phase, individual duplex is used at 0.1-100 nM (final). Transient transfections are carried out using either Lipofectamine 2000 from Invitrogen (Carlsbad, Calif.) or GeneSilencer from Gene Therapy Systems (San Diego, Calif.) (see below). One day after transfections, total RNA is isolated using the RNeasy 96 Kit (Qiagen) according to manufacturer's instructions and expression of mRNA is quantitated using TaqMan technology. Apoptosis and cell proliferation assays can be performed daily using Apop-one homogeneous caspase-3/7 kit and Alamar Blue or CellTiter 96 AQueous One Solution Cell Proliferation Assays (see below).

RNAi Transfections—Lipofectamine 2000 and GeneSilencer

Transient RNAi transfections can be carried out using Lipofectamine 2000 (Invitrogen, Carlsbad, Calif.) or GeneSilencer (Gene Therapy Systems, San Diego, Calif.), such as on sub-confluent disease cell lines, as described elsewhere (Elbashir et al., 2001, *Nature* 411: 494-498; Caplen et al., 2001, *Proc Natl Acad Sci USA* 98: 9742-9747; Sharp, 2001, *Genes and Development* 15: 485-490). Synthetic RNA to a gene of interest or non-targeting negative control siRNA are transfected using Lipofectamine 2000 or GeneSilencer according to manufacturer's instructions. Cells are plated in 96-well plates in antibiotic-free medium. The next day, the transfection reagent and siRNA are prepared for transfections as follows.

0.1-100 nM siRNA is resuspended in 20-25 µl serum-free media in each well (with Plus for Lipofectamine 2000) and incubated at room temperature for 15 minutes. 0.1-1 µl of Lipofectamine 2000 or 1-1.5 µl of GeneSilencer is also resuspended in serum-free medium to a final volume of 20-25 µl per well. After incubation, the diluted siRNA and either the Lipofectamine 2000 or the GeneSilencer are combined and incubated for 15 minutes (Lipofectamine 2000) or 5-20 minutes (GeneSilencer) at room temperature. Media is then removed from the cells and the combined siRNA-Lipofectamine 2000 reagent or siRNA-GeneSilencer reagent is added to a final volume of 50 µl per well. After further incubation at 37° C. for 4 hours, 50 µl serum-containing medium is added back to the cells. 1-4 days after transfection, expression of mRNA can be quantitated by RT-PCR using TaqMan technology, and protein expression levels can be measured by flow cytometry. Apoptosis and proliferation assays can be performed daily using Apop-one homogeneous caspase-3/7 kit and Alamar Blue or CellTiter 96 AQueous One Solution Cell Proliferation Assays (see below).

mRNA and Protein Knockdowns

Knockdown of target mRNA levels can be monitored by Q-PCR one day after siRNA transfection by using a Taq-Man® assay (Applied Biosystems, Foster City, Calif.). RT-PCR is accomplished in a one-step reaction by using M-MLV reverse transcriptase (Promega, Madison, Wis.) and Ampli-Taq Gold® (ABI) and analyzed on the ABI Prism® 7900HT Sequence Detection System (ABI). Relative gene expression can be quantitated by the $\Delta\Delta Ct$ method (User Bulletin #2, ABI) with 18S rRNA serving as the endogenous control.

Protein knockdown can be monitored by FACS four days after transfection by using an antibody to the target. The samples can be run on a LSR flow cytometer (BD Biosciences, San Jose, Calif.) and live cells monitored by using PI exclusion (50 µg/ml PI, 2.5 units/ml RNase A, 0.1% Triton X-100 in D-PBS). The data can be analyzed using CellQuest software.

Cell Proliferation—Alamar Blue

Cell growth can be assessed four days after transfection by adding a 1:10 dilution of Alamar blue reagent (Invitrogen, Carlsbad, Calif. or Biosource, Camarillo, Calif.) and incubated for 2 hours at 37° C. Analysis can be performed on a Spectrafluor Plus (Tecan, Durham, N.C.) set at excitation wavelength of 530 nm and emission wavelength of 595 nm.

Cell Proliferation—MTS

Alternatively, cell proliferation assays can be performed using a CellTiter 96 AQueous One Solution Cell Proliferation Assay kit (Promega, Madison, Wis.). 200 of CellTiter 96 AQueous One Solution is added to 1000 of culture medium. The plates are then incubated for 1-4 hours at 37° C. in a humidified 5% $CO_2$ incubator. After incubation, the change in absorbance is read at 490 nm.

Apoptosis

Apoptosis assays can be performed using the Apop-one homogeneous caspase-3/7 kit (Promega, Madison, Wis.). Briefly, the caspase-3/7 substrate is thawed to room temperature and diluted 1:100 with buffer. The diluted substrate is then added 1:1 to cells, control, or blank. The plates are then placed on a plate shaker for 30 minutes to 18 hours at 300-500 rpm. The fluorescence of each well is then measured using an excitation wavelength of 485+/−20 nm and an emission wavelength of 530+/−25 nm.

11. Antibody Assays in Cell Lines

Cytotoxicity Assays

Cytotoxicity can be measured using a Resazurin (Sigma, Mo.) dye reduction assay (McMillian et al., 2002, *Cell Biol. Toxicol.* 18:157-173). Briefly, cells are plated at 1,000-5,500 cells/well in 96 well plates, allowed to attach to the plates for 18 hours before addition of fresh media with or without antibody. After 96-144 hours of exposure to antibody, resazurin is added to cells to a final concentration of 50 µM. Cells are incubated for 2-6 hours depending on dye conversion of cell lines, and dye reduction is measured on a Fusion HT fluorescent plate reader (Packard Instruments, Meridien, Conn.) with excitation and emission wavelengths of 530 nm and 590 nm, respectively. The $IC_{50}$ value is defined here as the drug concentration that results in 50% reduction in growth or viability as compared with untreated control cultures.

Assays for Antibody-Dependent Cellular Cytotoxicity

Antibody-dependent cellular cytotoxicity (ADCC) assays can be carried out as follows. Cultured disease cells (e.g., tumor cells) are labeled with 100 µCi $^{51}Cr$ for 1 hour (Livingston et al., 1997, *Cancer Immunol. Immunother.* 43, 324-330). After being washed three times with culture medium, cells are resuspended at $10^5$/ml, and 100 µl/well are plated onto 96-well round-bottom plates. A range of antibody concentrations are applied to the wells, including an isotype control together with donor peripheral blood mononuclear cells that are plated at a 100:1 and 50:1 ratio. After an 18 hour incubation at 37° C., supernatant (30 µl/well) is harvested and transferred onto Lumaplate 96 (Packard), dried, and read in a Packard Top-Count NXT γ counter. Spontaneous release is determined by cpm of disease cells incubated with medium and maximum release by cpm of disease cells plus 1% Triton X-100 (Sigma). Specific lysis is defined as: % specific lysis= [(experimental release−spontaneous release)/(maximum release−spontaneous release)]×100. The percent ADCC is expressed as peak specific lysis postimmune subtracted by preimmune percent specific lysis. A doubling of the ADCC to >20% can typically be considered significant.

Assays for Complement Dependent Cytotoxicity

Chromium release assays to assess complement dependent cytotoxicity (CDC) can be carried out as follows (Dickler et al., 1999, *Clin. Cancer Res.* 5, 2773-2779). Cultured disease cells (e.g., tumor cells) are washed in FCS-free media two times, resuspended in 500 µl of media, and incubated with 100 µCi $^{51}$Cr per 10 million cells for 2 hours at 37° C. The cells are then shaken every 15 min for 2 hours, washed 3 times in media to achieve a concentration of approximately 20,000 cells/well, and then plated in round-bottom plates. The plates contain either 50 µl cells plus 50 µl monoclonal antibody, 50 µl cells plus serum (pre- and post-therapy), or 50 µl cells plus mouse serum as a control. The plates are incubated in a cold room on a shaker for 45 min. Human complement of a 1:5 dilution (resuspended in 1 ml of ice-cold water and diluted with 3% human serum albumin) is added to each well at a volume of 100 µl. Control wells include those for maximum release of isotope in 10% Triton X-100 (Sigma) and for spontaneous release in the absence of complement with medium alone. The plates are incubated for 2 hours at 37° C., centrifuged for 3 min, and then 100 µl of supernatant is removed for radioactivity counting. The percentage of specific lysis is calculated as follows: % cytotoxicity=[(experimental release−spontaneous release)/(maximum release−spontaneous release)]×100. A doubling of the CDC to >20% can typically be considered significant.

Cell Proliferation Assays

To measure cell proliferation, cells can be plated, grown and treated as for the cytotoxicity assay (above) in 96 well plates. After 96-144 hours of treatment, 0.5 µCi/well $^3$H-Thymidine (PerkinElmer, 6.7 Ci/mmol) is added to cells and incubated for 4-6 hours at 37° C., 5% $CO_2$ in an incubator. To lyse cells, plates are frozen overnight at −20° C. and then cell lysates are harvested using FilterMate (Packard Instrument, Meridien, Conn.) into 96 well filter plates. Radioactivity associated with cells is measured on a TopCount (Packard) scintillation counter.

Other cell assays (e.g., proliferation assays such as Alamar blue and MTS, and apoptosis assays) can be carried out using antibodies, as described above for RNAi.

Testing of Function-Blocking Antibodies

For testing of function-blocking antibodies, sub-confluent disease cell lines are serum-starved overnight. The next day, serum-containing media is added back to the cells in the presence of 5-50 ng/ml of function-blocking antibodies. After 2 or 5 days incubation at 37° C. 5% $CO_2$, antibody binding is examined by flow cytometry, and apoptosis and proliferation are measured.

Cell Invasion

Cell invasion assays can be performed using a 96-well cell invasion assay kit (Chemicon). After the cell invasion chamber plates are adjusted to room temperature, 100 µl serum-free media is added to the interior of the inserts. 1-2 hours later, cell suspensions of 1×10$^6$ cells/ml are prepared. Media is then carefully removed from the inserts and 100 µl of prepared cells are added into the insert +/−0 to 50 ng function blocking antibodies. The cells are pre-incubated for 15 minutes at 37° C. before 150 µl of media containing 10% FBS is added to the lower chamber. The cells are then incubated for 48 hours at 37° C. After incubation, the cells from the top side of the insert are discarded and the invasion chamber plates are then placed on a new 96-well feeder tray containing 150 µl of pre-warmed cell detachment solution in the wells. The plates are incubated for 30 minutes at 37° C. and are periodically shaken. Lysis buffer/dye solution (4 µl CyQuant Dye/300 µl 4× lysis buffer) is prepared and added to each well of dissociation buffer/cells on feeder tray. The plates are incubated for 15 minutes at room temperature before 150 µl is transferred to a new 96-well plate. Fluorescence of invading cells is then read at 480 nm excitation and 520 nm emission.

Receptor Internalization

For quantification of receptor internalization, ELISA assays can be performed essentially as described by Daunt et al. (Daunt et al., 1997, *Mol. Pharmacol.* 51, 711-720). Cell lines are plated at 6×10$^5$ cells per in a 24-well tissue culture dishes that have previously been coated with 0.1 mg/ml poly-L-lysine. The next day, the cells are washed once with PBS and incubated in DMEM at 37° C. for several minutes. Agonist to the cell surface target of interest is then added to the wells at a pre-determined concentration in prewarmed DMEM. The cells are then incubated for various times at 37° C. and reactions are stopped by removing the media and fixing the cells in 3.7% formaldehyde/TBS for 5 min at room temperature. The cells are then washed three times with TBS and nonspecific binding blocked with TBS containing 1% BSA for 45 min at room temperature. The first antibody is added at a pre-determined dilution in TBS/BSA for 1 hr at room temperature. Three washes with TBS follow, and cells are briefly reblocked for 15 min at room temperature. Incubation with goat anti-mouse conjugated alkaline phosphatase (Bio-Rad) diluted 1:1000 in TBS/BSA is carried out for 1 hr at room temperature. The cells are washed three times with TBS and a colorimetric alkaline phosphatase substrate is added. When the adequate color change is reached, 100 µl samples are taken for colorimetric readings.

12. Treatment with Antibodies

Treatment of Disease Cells with Monoclonal Antibodies.

Disease cells (e.g., cancer cells), or cells such as NIH 3T3 cells that express a target of interest, are seeded at a density of 4×10$^4$ cells per well in 96-well microtiter plates and allowed to adhere for 2 hours. The cells are then treated with different concentrations of monoclonal antibody (Mab) specific for the protein target of interest, or irrelevant isotype matched (e.g., anti-rHuIFN-gamma) Mab, at 0.05, 0.5 or 5.0 µg/ml. After a 72 hour incubation, the cell monolayers are stained with crystal violet dye for determination of relative percent viability (RPV) compared to control (untreated) cells. Each treatment group can have replicates. Cell growth inhibition is monitored.

In Vivo Treatment with Monoclonal Antibodies.

NIH 3T3 cells transfected with either an expression plasmid that expresses the target of interest or a neo-DHFR vector are injected into nu/nu (athymic) mice subcutaneously at a dose of 10$^6$ cells in 0.1 ml of phosphate-buffered saline. On days 0, 1, 5, and every 4 days thereafter, 100 µg (0.1 ml in PBS) of a Mab specific for the protein target of interest, or an irrelevant Mab, of the IgA2 subclass is injected intraperitoneally. Disease progression (e.g., tumor occurrence and size) can be monitored for a one month period of treatment, for example.

13. Examples of Results from Experimental Validation

The Genbank protein accession numbers, and protein SEQ ID NOS corresponding to Table 1, for the four targets described below are as follows: Angiopoietin-like 4 (ANGPTL4)=Q9BY76 (protein SEQ ID NOS:476-478 in Table 1), Tweety Homolog 3 (TTYH3)=NP_079526 (exemplary TTYH3 protein and encoding transcript sequences are provided in the sequence listing as SEQ ID NOS:1977-1978), CEACAM6 (carcinoembryonic antigen-related cell adhesion molecule 6 precursor)=P40199 or NP_002474 (exemplary CEACAM6 protein and encoding transcript sequences are provided in the sequence listing as SEQ ID NOS:1975-1976), and protein FLJ11273=gi|20380426 (protein SEQ ID NOS: 713-714 in Table 1).

Angiopoietin-Like 4 (ANGPTL4)

ANGPTL4 peptides were identified by mass spec to be over-expressed by 36-fold in spheroid cells (i.e., cancer stem cells) compared with parental adherent cells from lung cancer cell line H1299.

See FIG. 1 for further results from experimental validation of ANGPTL4.

Tweety Homolog 3 (TTYH3)

A TTYH3 peptide was identified by mass spec as over-expressed by the following ratios: 6.8-fold in spheroid cells (i.e., cancer stem cells) compared with differentiated cells from a colon cancer cell line (referred to as CBT026T), 9.9-fold in a colon tumor tissue sample, and 6.5-fold in a liver cancer cell line.

Figure 2:
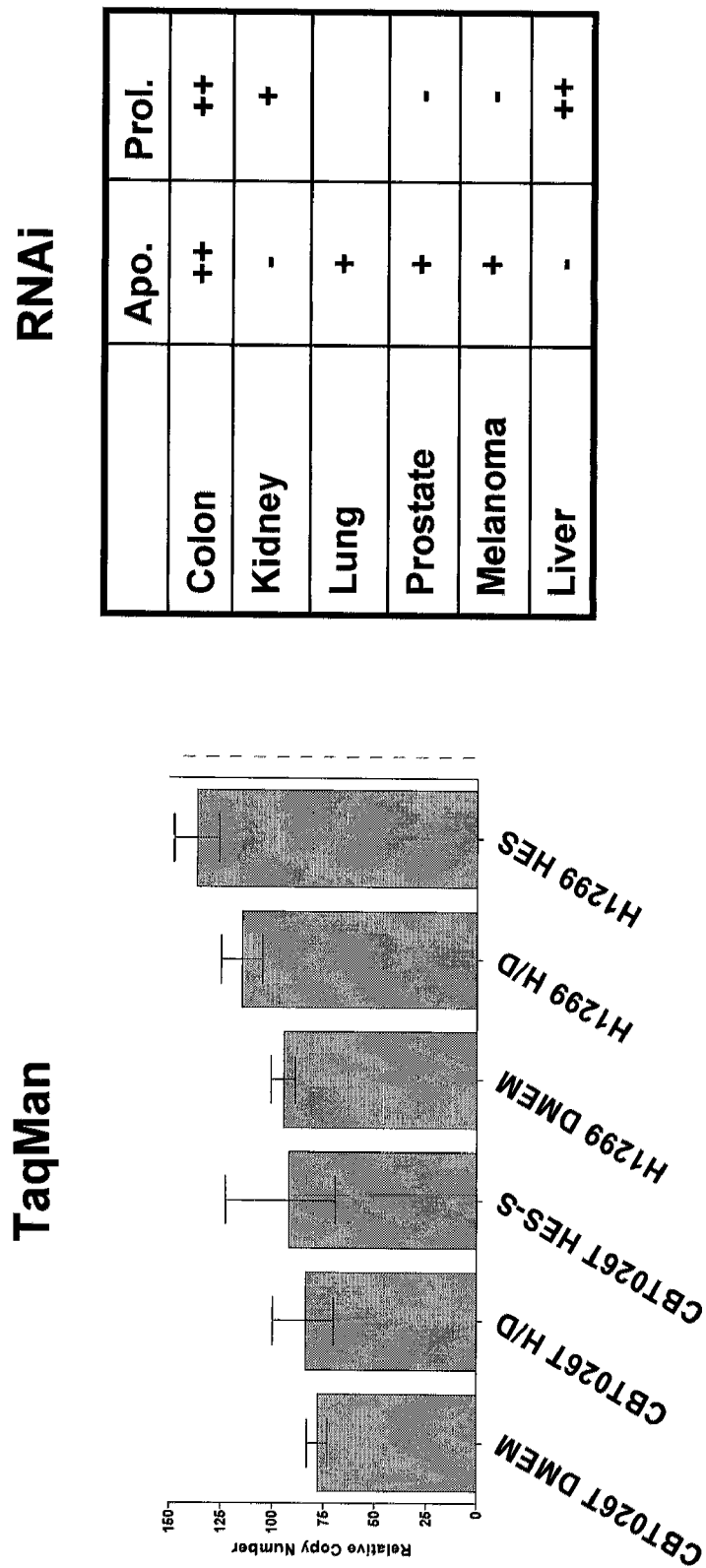

See FIG. 2 for further results from experimental validation of TTYH3.

CEACAM6 (carcinoembryonic antigen-related cell adhesion molecule 6 precursor)

CEACAM6 peptides were identified by mass spec as over-expressed by the following ratios: 5.5-fold in spheroid cells (i.e., cancer stem cells) compared with differentiated cells from a colon cancer cell line (referred to as CBT026T), 9.4-49.0 fold in a colon tumor tissue sample, 4.6-5.3 fold in a liver tumor tissue sample, and 9.1-24.0 fold in a pancreatic cancer cell line.

Figure 3:
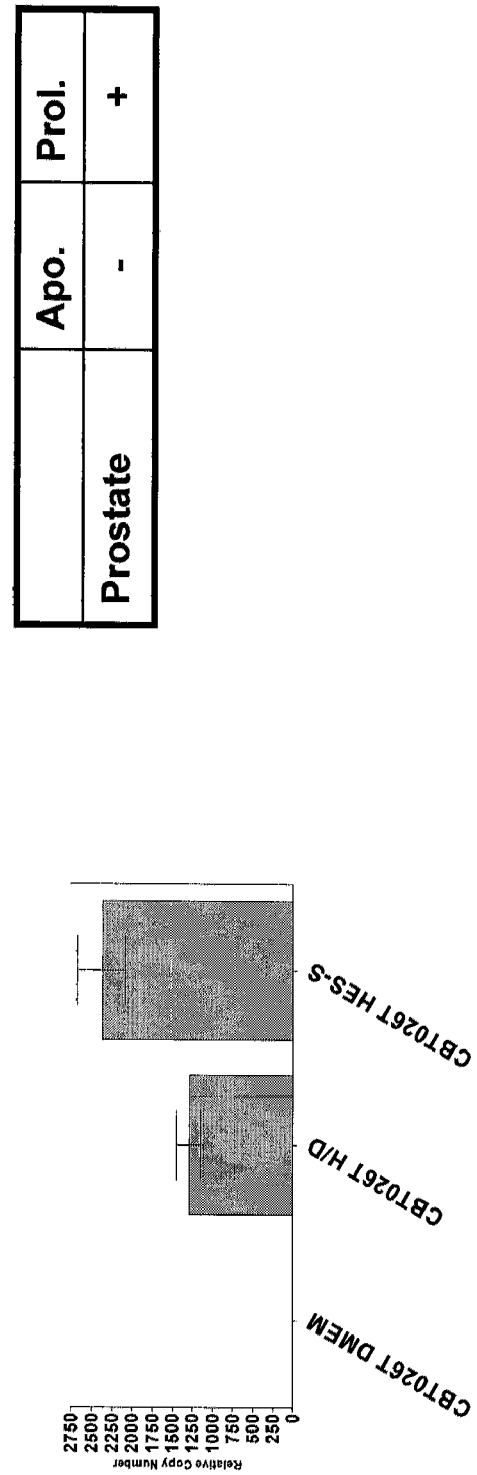

See FIG. 3 for further results from experimental validation of CEACAM6.

Protein FLJ11273

An FLJ11273 peptide was identified by mass spec as over-expressed by 5.5-fold in spheroid cells (i.e., cancer stem cells) compared with differentiated cells from a colon cancer cell line (referred to as CBT026T).

Figure 4:
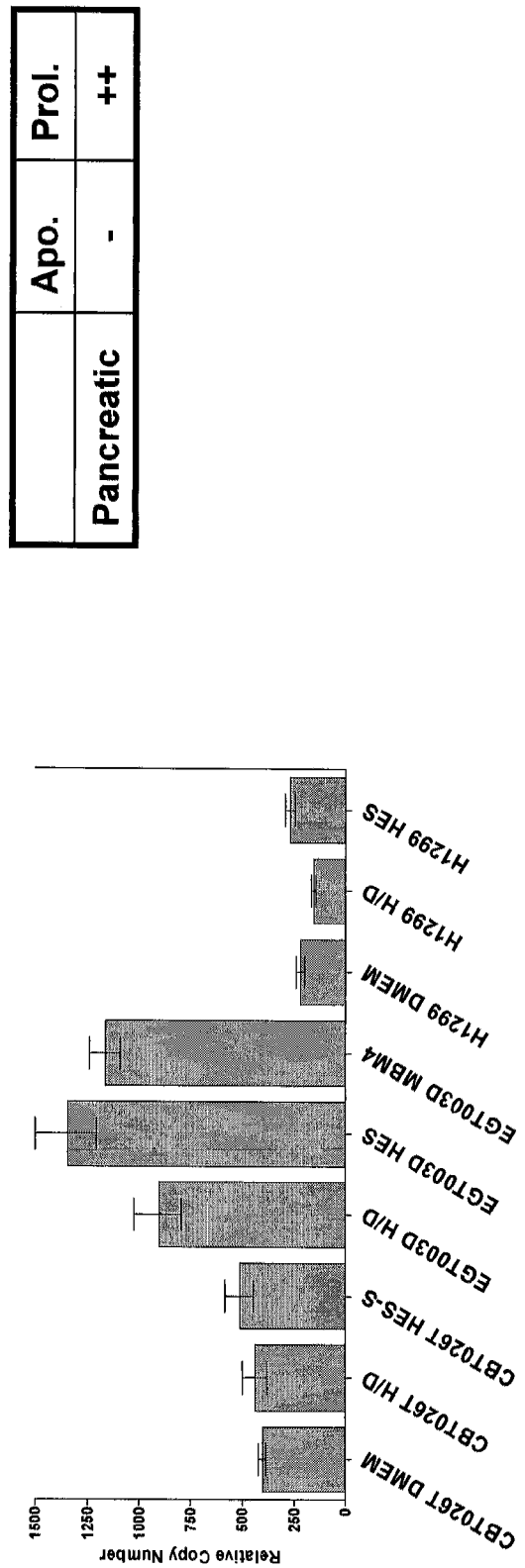

See FIG. 4 for further results from experimental validation of FLJ11273.

14. Examples of Results of RNAi Assays in Cancer Stem Cell Lines

RNAi knockdown of the prominin 1 (PROM1) target in colon cancer stem cell line CBT026T-HES induced apoptosis and inhibited cell proliferation in this cell line (prominin 1 is represented in Table 1 by protein SEQ ID NOS:411-413 and 700).

RNAi knockdown of the integrin beta-6 (ITGB6) target in the HT29 colon cancer stem cell line inhibited cell proliferation in this cell line (ITGB6 is represented in Table 1 by protein SEQ ID NOS:379-380).

All publications and patents mentioned in the above specification are herein incorporated by reference. Various modifications and variations of the described methods and compositions of the invention will be apparent to those skilled in the art without departing from the scope and spirit of the invention. Although the invention has been described in connection with specific exemplary embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

TABLE 3

| Target Symbol | IHC | Apoptosis | Proliferation | Matrix | Subcellular Location |
|---|---|---|---|---|---|
| ITAV_HUMAN | | | | H1299_StemCell_Cys_Only | Cell Surface |
| SLC1A5 | 30% Ovarian Tumors<br>40% Prostate Tumors<br>40% Met Panc Tumors<br>20% Panc Tumors | | Colon (++)<br>Pancreatic (++)<br>Prostate (++) | CBT026_HES_Primary | Cell Surface |
| ATP1B3 | 100% Glioblastoma<br>80% NSC Lung Tumors<br>71% Panc Tumors<br>70% Breast<br>70% Melanoma<br>70% Melanoma Node<br>67% Met Panc Tumors<br>70% Squ Lung<br>50% Colon<br>50% Ovary<br>38% Liver Tumors<br>30% Gastric Tumors | Kidney (++)<br>Melanoma (++)<br>Pancreatic (++)<br>Gastric (+) | Pancreatic (+++)<br>Gastric (++)<br>Kidney (++)<br>Lung (++)<br>Melanoma (++) | HT29_Stemcell<br>CBT026_HES_Primary | Cell Surface |
| TSN1_HUMAN | 50% Liver Tumors<br>40% Melanoma Node<br>100% Pancreas Tumors<br>100% Met Pancreas Tumors | | Colon (++)<br>Gastric (++)<br>Melanoma (++)<br>Pancreatic (+)<br>Prostate (+) | CBT026_T<br>CBT026_HES_Primary | Cell Surface |
| TFR1_HUMAN | | | | CBT026_N<br>CBT026_HES_Primary | Cell Surface |
| T4S3_HUMAN | | | Pancreatic (++) | CBT026_N<br>CBT026_T | Cell Surface |
| M6PR | | | Lung (++)<br>Pancreatic (++)<br>Gastric (+) | HT29_Stemcell<br>CBT026_N<br>CBT026_HES_Primary | Cell Surface |
| BST2 | | Colon (++)<br>Liver (++)<br>Lung (++)<br>Melanoma (++)<br>Ovary (+) | Colon (++)<br>Liver (++)<br>Lung (++)<br>Melanoma (++) | CBT026_N<br>RKO Sphere vs<br>Adherent PNGF | Cell Surface |

TABLE 3-continued

| Target Symbol | IHC | Apoptosis | Proliferation | Matrix | Subcellular Location |
|---|---|---|---|---|---|
| CEACAM5 | | | | CBT026_N<br>CBT026_T<br>CBT026_HES_Primary | Cell Surface |
| ITGA6 | 100% Kidney Tumors<br>80% NSC Lung Tumors<br>70% Squ Lung Tumors<br>67% Met Panc Tumors<br>60% Melanoma Node<br>50% Melanoma<br>50% Glioblastoma<br>40% Gastric Tumors<br>63% Liver Tumors<br>25% Panc Tumors<br>20% Ovary Tumors<br>20% Colon Tumors | Colon (++) | Lung (+++)<br>Colon (++)<br>Gastric (++) | CBT026_N<br>CBT026_T<br>CBT026_HES_Primary | Cell Surface |
| ITGB4 | 40% Breast Tumors | | Colon (++) | CBT026_N<br>CBT026_T<br>CBT026_HES_Primary | Cell Surface |
| C20orf3 | 80% Melanoma<br>70% Melanoma Node<br>50% NHL, Lymph Node<br>50% Colon Tumors<br>50% Kidney Tumors<br>83% Glioblastoma<br>33% Met Panc Tumors<br>29% Panc Tumors<br>20% Prostate Tumors<br>25% Liver Tumors | | Colon (++)<br>Liver (++)<br>Lung (++) | CBT026_N<br>CBT026_T<br>CBT026_HES_Primary<br>RKO Sphere vs<br>Adherent PNGF | Cell Surface |
| TACSTD1 | | | | CBT026_N<br>CBT026_T<br>CBT026_HES_Primary | Cell Surface |
| TM9SF3 | 90% Melanoma<br>50% Glioblastoma<br>40% Colon Tumors<br>60% Melanoma Node<br>33% NHL Node<br>20% Prostate Tumors | | Pancreatic (++) | HT29_Stemcell<br>CBT026_N<br>CNT026_HES_Primary | Cell Surface |
| ECE1 | | | | H1299_StemCell_Glyco | Cell Surface |
| CALR | | | | CBT026_N | Cell Surface |
| ICAM1 | | | | RKO Sphere vs<br>Adherent PNGF | Cell Surface |
| ADAM10 | | | | CBT026_N<br>CBT026_HES_Primary | Cell Surface |
| SYPL | | | | CBT026_T<br>Melanoma<br>Stemcell_EGT003D | Cell Surface |
| LMAN2 | | | | HT29_StemCell<br>CBT026_N<br>H1299_StemCell_Glyco | Cell Surface |
| ITM1 | | Colon (++) | Colon (++) | HT29_StemCell<br>CBT026_N<br>CBT026_T | Cell Surface |
| MUC13 | 100% Glioblastoma<br>100% Colon Tumors<br>30% Esoph Tumors<br>100% Liver Tumors<br>30% Melanoma Node<br>70% Pancreas Tumors<br>70% Melanoma<br>30% Gastric Tumors | Pancreatic (++)<br>Colon (+) | Gastric (++) | CBT026_N<br>CBT026_HES_Primary | Cell Surface |
| LTF | | | | Melanoma<br>StemCell_EGT003D | Secreted |
| SLC5A1 | 33% Glioblastoma<br>100% Colon Tumors<br>90% Kidney Tumors<br>88% Liver Tumors<br>70% NSC Lung Tumors<br>20% Squ Lung Tumors<br>50% Melanoma Node<br>50% NHL Node<br>86% Panc Tumors<br>100% Met Panc Tumors<br>50% Melanoma | Colon (++) | Colon (++)<br>Gastric (++)<br>Pancreatic (++) | CBT026_N | Cell Surface |
| PROM1 | 60% Colon | Lung (++) | Colon (++)<br>Lung (++) | CBT026_N<br>CBT026_T<br>CBT026_HES_Primary | Cell Surface |

TABLE 3-continued

| Target Symbol | IHC | Apoptosis | Proliferation | Matrix | Subcellular Location |
|---|---|---|---|---|---|
| NPC2 | 70% Breast Tumors<br>50% Colon Tumors<br>70% NSC Lung Tumors<br>43% Panc Tumors<br>66% Met Panc Tumors<br>20% Prostate Tumors | | Colon (++) | Melanoma Stemcell_EGT003D | Secreted |
| CD68 | | Kidney (++) | Liver (++)<br>Gastric (+) | CSC Overlap<br>CBT026_N | Cell Surface |
| CTSB | | | | Melanoma Stemcell_EGT003D | Secreted |
| CTSD | | | Gastric (++)<br>Liver (++) | CBT026_N<br>Melanoma Stemcell_EGT003D | Secreted |
| OLFM4 | 70% Bladder Tumors<br>20% Colon Tumors<br>100% Kidney Tumors<br>38% Liver Tumors<br>40% Melanoma Node<br>33% NHL Node<br>50% Gastric Tumors | | | CBT026_N | Secreted |
| CDH17 | | | | CBT026_N<br>CBT026_T<br>CBT026_HES_Primary | Cell Surface |
| ITGB6 | | Colon (++)<br>Kidney (++)<br>Lung (++)<br>Pancreatic (++)<br>Gastric (+)<br>Liver (+) | Colon (++)<br>Gastric (++)<br>Lung (++)<br>Pancreatic (++)<br>Liver (+) | HT29_StemCell | Cell Surface |
| ST14 | 70% Colon Tumors<br>20% Squ Lung Tumors<br>80% NHL Node<br>60% Ovary Tumors<br>38% Panc Tumors | | Colon (++)<br>Lung (++)<br>Pancreatic (++)<br>Gastric (+) | CBT026_T<br>CBT026_HES_Primary | Cell Surface |
| XP_114346 | | Colon (++)<br>Lung (++) | Colon (++)<br>Lung (++) | HT29_StemCell<br>CBT026_N<br>CBT026_T<br>CBT026_HES_Primary | Cell Surface |
| FLJ14681 | | | | H1299_StemCell_Glyco | Cell Surface |
| SERPINF2 | | | | Melanoma Stemcell_EGT003D | Secreted |
| DPEP1 | 38% Liver<br>20% Colon<br>20% Prostate<br>10% Gastric | Colon (++) | Colon (+++) | CBT026_N | Cell Surface |
| GP25L2 | | | | CBT026_N | Cell Surface |
| GPC1 | | | Gastric (++)<br>Liver (++)<br>Breast (+)<br>Lung (+) | RKO Sphere vs Adherent PNGF | Cell Surface |
| gi|23268459 | | | | Melanoma Stemcell_EGT003D | Secreted |
| NCSTN | | | | CBT026_N<br>CBT026_T<br>CBT026_HES_Primary | Cell Surface |
| CD97 | | | | CBT026_N | Cell Surface |
| LY75 | | Colon (++)<br>Kidney (++) | Kidney (++) | HT29_Stemcell | Cell Surface |
| SLC11A2 | | | | HT29_StemCell | Cell Surface |
| ANPEP | | | | H1299_StemCell_Glyco | Secreted |
| GGT1 | | | | CBT026_N | Cell Surface |
| CEACAM1 | | | | HT29_StemCell<br>CBT026_N<br>CBT026_T<br>CBT026_HES_Primary | Cell Surface |
| PGLYRP2 | | | | Melanoma Stemcell_EGT003D | Secreted |
| PZP | | | | LS123_StemCell | Secreted |
| Q9Y3B3 | | | | Melanoma Stemcell_EGT003D | Cell Surface |
| BGN | | | | CBT026_2Maps<br>CBT026_N<br>CBT026_T<br>CBT026_HES_Primary<br>HT29_StemCell<br>RKO Sphere vs Adherent PNGF | Secreted |

TABLE 3-continued

| Target Symbol | IHC | Apoptosis | Proliferation | Matrix | Subcellular Location |
|---|---|---|---|---|---|
| PIGR | | | Colon (++)<br>Lung (++) | H1299_Stemcell_Glyco<br>Melanoma<br>Stemcell_EGT003D<br>HT29_Stemcell | Cell Surface |
| DSG2 | | Kidney (++) | Kidney (++)<br>Pancreatic (+) | HT29_Stemcell | Cell Surface |
| gi\|22859168 | | | Colon (++)<br>Pancreatic (++)<br>Gastric (+)<br>Kidney (+)<br>Melanoma (+) | HT29_Stemcell | Cell Surface |
| PTGFRN | | | | CBT026_N<br>CBT026_HES_Primary | Cell Surface |
| IGSF8 | 66% NHL Node<br>20% Ovary Tumors<br>30% Melanoma | | Colon (++)<br>Gastric (++)<br>Lung (++) | CBT026_HES_Primary | Cell Surface |
| gi\|41352831 | | | | Melanoma<br>StemCell_EGT003D | Cell Surface |
| CDCP1 | | | Breast (+++)<br>Colon (+++)<br>Lung (+++)<br>Gastric (++)<br>Liver (++)<br>Melanoma (++)<br>Pancreatic (++) | CBT026_N | Cell Surface |
| ATP1B1 | 70% Melanoma node<br>70% Breast Tumors<br>67% Glioblastoma<br>50% Melanoma<br>20% Esoph Tumors | Lung (++)<br>Melanoma (++) | Breast (++)<br>Colon (++)<br>Melanoma (++) | CBT026_N<br>CBT026_T<br>CBT026_HES_Primary<br>HT29_Stemcell | Cell Surface |
| CLIC1 | | Melanoma (++) | Gastric (++)<br>Melanoma (++) | H1299_Stemcell_Cys_Only<br>CBT026_N | Cell Surface |
| CLU | 30% Breast Tumors<br>60% Ovary Tumors<br>30% Prostate Tumors | | Colon (++)<br>Melanoma (+) | CBT026_T<br>CBT026_HES_Primary<br>H1299_Stemcell_Glyco | Secreted |
| TIMP1 | | | | RKO Sphere vs<br>Adherent PNGF | Secreted |
| TM9SF1 | 50% Panc Tumors<br>20% Prostate Tumors | | Kidney (++)<br>Lung (++) | HT29_Stemcell | Cell Surface |
| LGALS3BP | | | | Melanoma<br>Stemcell_EGT003D<br>CBT026_T<br>CBT026_N<br>CBT026_HES_Primary<br>H1299_Stem cell_Glyco | Secreted |
| FAT | | Gastric (++) | Colon (++)<br>Gastric (++)<br>Liver (+) | CBT026_N | Cell Surface |
| HLA-C | | | | CBT026_N | Cell Surface |
| ENPP1 | | | Colon (+) | H1299_Stemcell_Cys_Only | Secreted |
| HSPG2 | | | | H1299_Stemcell_Glyco<br>HT29_StemCell<br>H1299_StemCell_Glyco<br>CBT026_N | Secreted |
| PLTP | | Lung (+) | Colon (++)<br>Gastric (+)<br>Melanoma (+) | CBT026_12Maps | Secreted |
| PON1 | | | | RKO Sphere vs<br>Adherent PNGF | Secreted |
| HLA-C | | | | CBT026_N | Cell Surface |
| MUCDHL | | | Colon (++) | CBT026_N<br>CBT026_T | Cell Surface |
| SLC7A1 | | | Colon (++)<br>Liver (++)<br>Pancreatic (++)<br>Gastric (+) | CSC Overlap<br>CBT026_HES_Primary | Cell Surface |
| GPR56 | | | | CBT026_N | Cell Surface |
| P2RX4 | | Kidney (++) | Colon (++)<br>Kidney (++)<br>Gastric (+)<br>Lung (+) | CBT026_N | Cell Surface |
| gi\|21361918 | | | Melanoma (++)<br>Colon (+)<br>Gastric (+) | Melanoma<br>StemCell_EGT003D | Secreted |

TABLE 3-continued

| Target Symbol | IHC | Apoptosis | Proliferation | Matrix | Subcellular Location |
|---|---|---|---|---|---|
| HLA-A | | | | CBT026_12Maps | Cell Surface |
| ATP6V0A1 | | | | CBT026_T | Cell Surface |
| | | | | CBT026_HES_Primary | Cell Surface |
| TM9SF4 | 40% Colon Tumors | | Colon (++) | Melanoma Stemcell_EGT003D | Cell Surface |
| | 100% Liver Tumors | | | | |
| | 56% NSC Lung Tumors | | | | |
| | 64% Squ Lung Tumors | | | | |
| | 80% Melanoma Node | | | | |
| | 50% NHL Node | | | | |
| | 88% Panc Tumors | | | | |
| | 50% Met Panc Tumors | | | | |
| | 70% Melanoma | | | | |
| TMED7 | | | | Melanoma Stemcell_EGT003D | Cell Surface |
| KIAA1815 | 33% Glioblastoma | | Breast (++) | CBT026_N | Cell Surface |
| | 38% Liver Tumors | | Lung (++) | HT29_Stemcell | |
| | 73% Squ Lung Tumors | | | | |
| | 50% Panc Tumors | | | | |
| | 30% Prostate Tumors | | | | |
| CD82 | | Lung (+) | Colon (++) | CBT026_HES_Primary | Cell Surface |
| | | Ovary (+) | Pancreatic (++) | | |
| LAMA4 | | | | CBT026_12Maps | Secreted |
| SERPINE2 | | Kidney (++) | Lung (++) | H1299_Stemcell_Glyco | |
| | | Lung (++) | | | |
| | | Ovary (+) | | | |
| GOLPH2 | | | | HT29_StemCell | Secreted |
| | | | | CBT026_N | |
| BMP1 | | | | H1299_Stemcell_Glyco | Secreted |
| EVA1 | | | | HT29_Stem cell | Cell Surface |
| SERPINF1 | | | | CBT026_12 maps | Secreted |
| | | | | HT29_Stemcell | |
| | | | | CBT026_HES_ Primary | |
| GREM2 | | | | HT29_Stemcell | Secreted |
| FAM38A | | | | HT29_Stemcell | Cell Surface |
| LIPG | | | | HT29_stem cell | Secreted |
| ST3GAL1 | | | Melanoma (++) | CBT026_N | Secreted |
| LNPEP | | | | CBT026_N | Cell Surface |
| MFAP4 | | | | CBT026_HES_Primary | Secreted |
| | | | | CBT026_N | |
| | | | | CBT026_T | |
| DKFZP564G2022 | | | | CBT026_N | Cell Surface |
| CEACAM6 | | Gastric (+) | Prostate (+) | CBT026_N | Cell Surface |
| | | | | CBT026_T | |
| | | | | CBT026_HES_primary | |
| FLJ11273 | | Colon (+) | Pancreatic (++) | CBT026_T | Cell Surface |
| | | | Colon (+) | CBT026_N | |
| | | | | CBT026_HES_Primary | |
| CEACAM7 | | | | CBT026_N | Cell Surface |
| CANT1 | | | | CBT026_N | Secreted |
| SSR1 | | Ovary (+) | Ovary (+) | CBT026_N | Cell Surface |
| | | | Pancreatic (+) | CBT026_T | |
| | | | | CBT026_HES_Primary | |
| TTYH3 | | Colon (++) | Colon (++) | CBT026_N | Cell Surface |
| | | Lung (++) | Gastric (++) | CBT026_T | |
| | | Melanoma (++) | Liver (++) | CBT026_HES_Primary | |
| | | Ovary (+) | Lung (++) | | |
| | | Prostate (+) | Melanoma (++) | | |
| | | | Kidney (+) | | |
| | | | Pancreatic (+) | | |
| CLPTM1 | | | | CBT026_N | Cell Surface |
| | | | | CBT026_HES_Primary | |
| FAM3D | | | Colon (++) | CBT026_N | Secreted |
| LOC284361 | | Colon (++) | Colon (++) | CBT026_N | Cell Surface |
| | | Lung (++) | Lung (++) | | |
| | | Kidney (+) | Pancreatic (+) | | |
| | | Liver (+) | | | |
| KIAA0090 | | Colon (++) | Colon (++) | CBT026_N | Secreted |
| | | Breast (+) | Lung (++) | CBT026_T | |
| | | | Pancreatic (+) | CBT026_HES_Primary | |
| LAMA5 | | | | H1299_StemCell_Glyco | Secreted |
| ATP6AP1 | | | | CBT026_HES_Primary | Cell Surface |
| PTPRK | | Lung (+) | Colon (++) | CBT026_HES_Primary | Cell Surface |
| | | Ovary (+) | Pancreatic (++) | | |
| | | | Prostate (+) | | |
| NCLN | | | | H1299_Stem Cell_Glyco | Cell Surface |

TABLE 3-continued

| Target Symbol | IHC | Apoptosis | Proliferation | Matrix | Subcellular Location |
|---|---|---|---|---|---|
| ANGPTL4 | | Colon (++)<br>Kidney (++)<br>Pancreatic (++) | Colon (++)<br>Kidney (++) | H1299_StemCell_Glyco | Secreted |
| MFGE8 | | | | H1299_StemCell_Glyco | Cell Surface |
| COMT | 100% Kidney Tumors<br>100% Ovary Tumors<br>60% Melanoma Node<br>50% Melanoma<br>43% Panc Tumors<br>50% Colon Tumors<br>30% Bladder Tumors<br>50% Glioblastoma<br>30% Squ Lung Tumors<br>30% Prostate Tumors<br>25% Liver Tumors | Breast (++)<br>Colon (++)<br>Gastric (++) | Colon (+++)<br>Lung (+++)<br>Melanoma (+++)<br>Breast (++)<br>Gastric (++)<br>Kidney (++)<br>Liver (++)<br>Prostate (++) | LS123_Stemcell | Cell Surface |
| GLG1 | 30% Squ Lung Tumors<br>50% Melanoma Node<br>43% Panc Tumors<br>80% Melanoma | | Liver (++)<br>Breast (+) | H1299_Stemcell_Glyco<br>Melanoma<br>Stemcell_EGT003D | Cell Surface |
| CD44 | | | | CBT026_HES_Primary | Cell Surface |
| LAMP1 | | | Prostate (++) | CBT026_N<br>CBT026_T<br>CBT026_HES_Primary | Cell Surface |
| SLC3A2 | 100% NSC Lung Tumors<br>100% Squ Lung Tumors<br>90% Melanoma<br>83% Glioblastoma<br>80% Colon Tumors<br>50% Breast Tumors | Pancreatic (++) | Lung (+++)<br>Colon (++)<br>Gastric (++)<br>Pancreatic (++)<br>Prostate (++) | CBT026_HES_Primary | Cell Surface |
| SCARB2 | | | | HT29_StemCell<br>CBT026_N<br>CBT026_T<br>CBT026_HES_Primary | Cell Surface |
| ITGA3 | | Pancreatic (++) | Pancreatic (++) | CBT026_N<br>CBT026_HES_Primary | Cell Surface |
| PLXNB2 | | | | CBT026_N<br>CBT026_HES_Primary | Cell Surface |
| LAMP2 | | Lung (++)<br>Melanoma (++)<br>Pancreatic (++)<br>Colon (+) | Liver (++)<br>Lung (++)<br>Colon (+) | CBT026_N<br>CBT026_T<br>CBT026_HES_Primary | Cell Surface |
| AADACL1 | 60% Colon Tumors<br>80% Melanoma Node<br>33% NHL Node<br>100% Panc Tumors<br>75% Met Panc Tumors<br>80% Melanoma | | | CBT026_N<br>CBT026_T<br>CBT026_HES_Primary | Cell Surface |
| ALCAM | 40% Breast Tumors<br>30% Bladder Tumors<br>20% Colon Tumors | Colon (++)<br>Gastric (++)<br>Kidney (++)<br>Liver (++)<br>Melanoma (+) | Breast (++)<br>Colon (++)<br>Gastric (++)<br>Kidney (++)<br>Liver (++)<br>Pancreatic (++)<br>Melanoma (+) | CBT026_five sets with<br>N primary | Cell Surface |
| SLC2A1 | | Colon (-)<br>Pancreatic (-)<br>Lung (-)<br>Breast (-)<br>Kidney (-)<br>Gastric (-)<br>Prostate (-)<br>Melanoma (-)<br>Liver (-) | Breast (-)<br>Colon (-)<br>Gastric (-)<br>Kidney (-)<br>Liver (-)<br>Lung (+)<br>Melanoma (-)<br>Pancreatic (-)<br>Prostate (-) | CBT026_T<br>CBT026_N<br>CBT026_HES_Primary | Cell Surface |
| ITGB1 | | | | CBT026_HES_Primary | Cell Surface |
| BSG | | Lung (-) | Lung (-) | CBT026_HES_Primary | Cell Surface |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08168586B1). An electronic copy of the "Sequence Listing" will also be available from the USPTO upon request and payment of the fee set forth in 37 CFR 1.19(b)(3).

That which is claimed is:

1. A method of inhibiting proliferation of pancreatic cancer cells in vitro, the method comprising contacting the pancreatic cancer cells in vitro with an isolated antibody that selectively binds to a SLC5A1 protein to thereby inhibit proliferation of the pancreatic cancer cells in vitro.

2. The method of claim 1, wherein the amino acid sequence of the SLC5A1 protein comprises SEQ ID NO:191.

3. The method of claim 1, wherein the antibody is coupled to at least one agent selected from the group consisting of drugs, toxins, differentiation inducers, and radionuclides.

4. The method of claim 2, wherein the antibody is coupled to at least one agent selected from the group consisting of drugs, toxins, differentiation inducers, and radionuclides.

* * * * *